(12) United States Patent
Gait et al.

(10) Patent No.: US 8,575,305 B2
(45) Date of Patent: Nov. 5, 2013

(54) CELL PENETRATING PEPTIDES

(75) Inventors: Michael John Gait, Cambridge (GB); Andrey Alexandrovich Arzumanov, Fulbourn (GB); Gabriela Dimitroval Ivanova, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 12/996,307

(22) PCT Filed: May 15, 2009

(86) PCT No.: PCT/GB2009/001261
§ 371 (c)(1), (2), (4) Date: Dec. 3, 2010

(87) PCT Pub. No.: WO2009/147368
PCT Pub. Date: Dec. 10, 2009

(65) Prior Publication Data
US 2011/0105403 A1 May 5, 2011

Related U.S. Application Data
(60) Provisional application No. 61/058,722, filed on Jun. 4, 2008.

(51) Int. Cl.
*C07K 9/00* (2006.01)
(52) U.S. Cl.
USPC .......................... 530/325; 514/21.3; 514/21.4
(58) Field of Classification Search
None
See application file for complete search history.

(56) References Cited

U.S. PATENT DOCUMENTS 7,153,931 B1    12/2006  Fischer et al. ................ 530/326

FOREIGN PATENT DOCUMENTS

WO    WO 03/106491      12/2003
WO    WO 2009/005793     1/2009

OTHER PUBLICATIONS

Abes, S., et al., "Vectorization of morpholino oligomers by the (R-Ahx-R)₄ peptide allows efficient splicing correction in the absence of endosomolytic agents"; *Journal of Controlled Release* 116: 304-313 (2006).
Abes, S., et al., "Peptide-based delivery of nucleic acids: design, mechanism of uptake and applications to splice-correcting oligonucleotides"; *Biochemical Society Transactions* 35(1): 53-55 (2007).
Abes, S., et al., "Efficient splicing correction by PNA conjugation to an R₆-Penetratin delivery peptide"; *Nucleic Acids Research* 35(13): 4495-4502 (2007).

Alter, J., et al., "Systemic delivery of morpholino oligonucleotide restores dystrophin expression bodywide and improves dystrophic pathology"; *Nature Medicine* 12(2):175-177 (2006).
Arechavala-Gomeza, V., et al., "Comparative analysis of antisense oligonucleotide sequences for targeted skipping of exon 51 during dystrophin pre-mRNA splicing in human muscle"; *Human Gene Therapy* 18: 798-810 (2007).
Bendifallah, N., et al., "Evaluation of cell-penetrating peptides (CPPs) as vehicles for intracellular delivery of antisense peptide nucleic acid (PNA)"; *Bioconjugate Chem*. 17: 750-758 (2006).
Cossu, G., et al., "New therapies for Duchenne muscular dystrophy: challenges, prospects and clinical trials"; *Trends in Molecular Medicine* 13(12): 520-526 (2007).
Du, L., et al., "Correction of prototypic ATM splicing mutations and aberrant ATM function with antisense morpholino oligonucleotides"; *Proc. Natl. Acad. Sci*. 104(14): 6007-6012 (2007).
Eckstein, F., "The versatility of oligonucleotides as potential therapeutics"; *Expert Opin. Biol. Ter*. 7(7): 1021-1034 (2007).
Egholm, M., et al., "Peptide nucleic acids (PNA). Oligonucleotide analogues with an achiral peptide backbone[1]"; *J. Am. Chem. Soc*. 114: 1895-1897 (1992).
El-Andaloussi, S., et al., "Induction of splice correction by cell-penetrating peptide nucleic acids"; *The Journal of Gene Medicine* 8: 1262-1273 (2006).
El-Andaloussi, S., et al., "A novel cell-penetrating peptide, M918, for efficient delivery of proteins and peptide nucleic acids"; *Mol. Ther*. 15(10): 1820-1826 (2007).
Esau, C., et al., "miR-122 regulation of lipid metabolism revealed by in vivo antisense targeting"; *Cell Metabolism* 3: 87-98 (2006).
Fabani, M., et al., "miR-122 targeting with LNA/2'-O-methyl oligonucleotide mixmers, peptide nucleic acids (PNA) and PNA-peptide conjugates"; *RNA* 14: 336-346 (2008).
Fletcher, S., et al., "Dystrophin expression in the *mdx* mouse after localised and systemic administration of a morpholino antisense oligonucleotide"; *J. Gene Med*. 8: 207-216 (2006).
Fletcher, S., et al., "Morpholino oligomer-mediated exon skipping averts the onset of dystrophic pathology in the *mdx* mouse"; *Mol. Ther*. 15(9): 1587-1592 (2007).
Ivanova, G., et al., "PNA-peptide conjugates as intracellular gene control agents"; *Nucleic Acids Symposium Series* 52: 31-32 (2008).
Ivanova, G., et al., "Improved cell-penetrating peptide—PNA conjugates for splicing redirection in HeLa cells and exon skipping in *mdx* mouse muscle"; *Nucleic Acids Research* 36(20): 6418-6428 (2008).
Jearawiriyapaisarn, N., et al., "Sustained dystrophin expression induced by peptide-conjugated morpholino oligomers in the muscles of *mdx* mice"; *Mol. Ther*. 16(9): 1624-1629 (2008).
Jopling, C.L., et al., "Modulation of Hepatitis C virus RNA abundance by a liver-specific microRNA"; *Science* 309: 1577-1581 (2006).
Kang, S.H., et al., "Up-regulation of Luciferase gene expression with antisense oligonucleotides: implications and applications in functional assay development"; *Biochemistry* 37: 6235-6239 (1998).
Kichler, A., et al., "Histidine-rich amphipathic peptide antibiotics promote efficient delivery of DNA into mammalian cells"; *Proc. Natl. Acad. Sci*. 100(4): 1564-1568 (2003).
Kole, R., et al., "Modification of alternative splicing by antisense therapeutics"; *Oligonucleotides* 14: 65-74 (2004).

(Continued)

*Primary Examiner* — John Ulm
(74) *Attorney, Agent, or Firm* — J. Peter Paredes; Rosenbaum IP

(57) ABSTRACT

The present invention discloses cell penetrating peptides and conjugates of a cell penetrating peptide and a cargo molecule.

21 Claims, 24 Drawing Sheets

(56) References Cited

OTHER PUBLICATIONS

Krutzfeldt, J., et al., "Silencing of microRNAs in vivo with 'antagomirs'"; *Nature* 438: 685-689 (2005).

Kurreck, J., "Antisense technologies. Improvement through novel chemical modifications"; *Eur. J. Biochem.* 270: 1628-1644 (2003).

Lebleu, B., et al., "Cell penetrating peptide conjugates of steric block oligonucleotides"; *Advanced Drug Delivery Reviews* 60: 517-529 (2008).

Lu, Q.L., et al., "Systemic delivery of antisense oligoribonucleotide restores dystrophin expression in body-wide skeletal muscles"; *Proc. Natl. Acad. Sci.* 102(1): 198-203 (2005).

Madsen, E., et al., "In vivo correction of a Menkes disease model using antisense oligonucleotides"; *Proc. Natl. Acad. Sci.* 105(10): 3909-3914 (2008).

Moulton, H.M., et al., "Cellular uptake of antisense morpholino oligomers conjugated to Arginine-rich peptides"; *Bioconjugate Chem.* 15: 290-299 (2004).

Rompp Online database, "Norleucin" (2009).

Rothbard, J., et al., "Arginine-rich molecular transporters for drug delivery: Role of backbone spacing in cellular uptake"; *J. Med. Chem.* 45: 3612-3618 (2002).

Scaffidi, P., et al., "Lamin A-dependent nuclear defects in human aging"; *Science* 312(5776): 1059-1063 (2006).

Seabra, L., et al., "Proteomic co-expression of cyclin-dependent kinases 1 and 4 in human cancer cells"; *Euro. J. of Cancer* 43:1483-1492 (2007).

Soifer, H.S., et al., "MicroRNAs in disease and potential therapeutic applications"; *Mol. Ther.* 15(12): 2070-2079 (2007).

Summerton, J., et al., "Morpholino antisense oligomers: Design, preparation and properties"; *Antisense & Nucleic Acid Drug Development* 7: 187-195 (1997).

Turner, J., et al., "Synthesis, cellular uptake and HIV-1 Tat-dependent trans-activation inhibition activity of oligonucleotide analogues disulphide-conjugated to cell-penetrating peptides"; *Nucleic Acids Research* 33(1): 27-42 (2005).

Turner, J., et al., "Cell-penetrating peptide conjugates of peptide nucleic acids (PNA) as inhibitors of HIV-1 Tat dependent trans-activation cells"; *Nucleic Acids Research* 33(21): 6837-6849 (2005).

Turner, J., et al., "Peptide conjugates of oligonucleotide analogs and siRNA for gene expression modulation"; in *Penetrating Peptides, 2nd Edition* (U. Langel Ed.), *CRC Press*, Boca Raton, pp. 313-328 (2006).

Turner, J., et al., "RNA targeting with peptide conjugates of oligonucleotides, siRNA and PNA"; *Blood Cells, Molecules and Diseases* 38: 1-7 (2007).

van Deutekom, J., et al., "Local dystrophin restoration with antisense oligonucleotide PRO051"; *N. Engl. J. Med.* 357(26): 2677-2686 (2007).

Wu, B., et al., "Effective rescue of dystrophin improves cardiac function in dystrophin-deficient mice by a modified morpholino oligomer"; *Proc. Natl. Acad. Sci.* 105(39): 14814-14819 (2008).

Yin, H., et al., "Effective exon skipping and restoration of dystrophin expression by peptide nucleic acid antisense oligonucleotides in *mdx* mice"; *Mol. Ther.* 16(1): 38-45 (2008).

Yin, H., et al., "Cell-penetrating peptide-conjugated antisense oligonucleotides restore systemic muscle and cardiac dystrophin expression and function"; *Human Molecular Genetics* 17(24): 3909-3918 (2008).

Zatsepin, T.S., et al., "Conjugates of oligonucleotides and analogues with cell penetrating peptides as gene silencing agents"; *Current Pharmaceutical Design* 11: 3639-3654 (2005).

Nomenclature, sequences and MALDI-TOF mass spectral data of CPP-PNA conjugates

| Name | Peptide sequence | Peptide length | Found (expected) m/z |
|---|---|---|---|
| Disulfide conjugates of CKPNA705K$_3$[1] | | | |
| 1a[2] | R$_6$-RQIKIWFQN-RRMKWKK-GG-C | 25 | 8778.5 (8780.5) |
| 1b | R$_6$-RQIKIWFQN-RRMKWKK-C | 23 | 8661.6 (8666.4) |
| 1c | (R-Ahx-R)$_3$-RQIKIWFQN-RRMKWKK-GG-C | 28 | 9118.6 (9120.0) |
| 1d[3] | R$_6$-RQIKILFQN-PKKKRKV-GG-C | 25 | 8558.9 (8557.3) |
| 1e[3] | R$_6$-RQIKILFQN-(R-Ahx)$_4$-C | 24 | 8657.4 (8655.4) |
| Disulfide conjugates of CKPNA705K[1] | | | |
| 2a | R$_6$-RQIKIWFQN-RRMKWKK-GG-C | 25 | 8525.0 (8524.1) |
| 2b | HHFFRRRRRRRRRFFC | 16 | 7513.8 (7510.9) |
| 2c | HHHHHHRRRRRRRRRFFC | 18 | 7767.9 (7765.1) |
| 2d | HHHHHHFFRRRRRRRRRFFC | 20 | 8054.0 (8059.5) |
| 2e | HHHHHHAhxAhxRRRRRRRRRFFC | 20 | 7985.9 (7991.4) |
| 2f | HHHHHHHAhxAhxFFRRRRRRRRRFFC | 22 | 8282.1 (8285.8) |
| 2g | HHHAhxRRRRRRRRRFFAhxHHHC | 20 | 8001.2 (8005.4) |

[1] PNA705 = cct ctt acc tca gtt aca
[2] The synthesis of 1a conjugate (R6Pen-S-S-KPNA705K$_3$) is published previously[19]
[3] W$_{13}$ is replaced by L, previously shown to slightly enhance activity[19]

Figure 3

| SEQ ID NO. | Domain 1 | Domain 2 | Domain 3 | Domain 4 (linker) | PNA Cargo | Name | Peptide-Cargo Linkage | EC$_{50}$ (μM) | Stable for 1h? |
|---|---|---|---|---|---|---|---|---|---|
| 1 | RRRRRR | RQIKIWFQN | RRMKWKK | GGCys | Cys-K-PNA705-K3 | R6Pen | disulfide linked | 0.7 ±0.3 | no |
| 2 | RRRRRR | RQIKIWFQN | RRMKWKK | GGCys | CH2-CO-K-PNA705-K3 | | thioether linked | 1.0 ±0.3 | no |
| 3 | | RQIKIWFQN | RRMKWKK | GGCys | Cys-K-PNA705-K3 | Pen | | > 4 | |
| 4 | RRRRRR | RQIKIWFQN | RRMKWKK | Cys | Cys-K-PNA705-K3 | | same as R6Pen | | |
| 5 | RXRRXRRXR | RQIKIWFQN | RRMKWKK | GGCys | Cys-K-PNA705-K3 | RXR3Pen | better than R6Pen | | |
| 6 | RRRRRR | RQIKILFQN | RXRXRXR | XCys | Cys-K-PNA705-K3 | | same as R6Pen | | |
| 7 | RXRRXRRXRRRXR | | | Cys | Cys-K-PNA-705-K | RXR4 | disulfide linked | 3.3 ± | |
| 8 | RXRRXRRXRRRXR | | | XCys | Cys-K-PNA-705-K | RXR4X | disulfide linked | 3.0 ± | |
| 9 | RXRRXRRXR | IKILFQN | RRMKWKK | GGCys | Cys-K-PNA-705-K | | disulfide linked | | |
| 10 | RXRRXRRXR | IKILFQN | RRMKWKK | Cys | Cys-K-PNA705-K | Pip-1 | disulfide linked | 0.50±0.05 | no |
| 11 | RXRRXRRXR | IKILFQN | RMKWKK | Cys | Cys-K-PNA705-K | | disulfide linked | 0.71±0.04 | |
| 12 | RXRRXRRXR | IKILFQN | XRMKWKK | Cys | Cys-K-PNA705-K | | disulfide linked | 0.70±0.10 | no |

Figure 15

| | | | | | | | |
|---|---|---|---|---|---|---|---|
| 13 | RXRRXRRXR | IKILFQN | HRMKWKK | Cys | Cys-K-PNA705-K | | disulfide linked | 0.65±0.10 | no |
| 14 | RXRRXRRXR | IKILFQN | dRRMKWKK | Cys | Cys-K-PNA705-K | | disulfide linked | 0.50±0.02 | better |
| 15 | RXRRXRRXR | IKILFQN | hRRMKWKK | Cys | Cys-K-PNA705-K | | disulfide linked | 0.57±0.07 | |
| 16 | RXRRXRRXR | IKILFQN | dRRMKWK | BCys | Cys-K-PNA705-K | | disulfide linked | 0.55±0.04 | |
| 17 | RXRRXRRXR | IKILFQN | dRRMKWHK | BCys | Cys-K-PNA705-K | | disulfide linked | 0.58±0.12 | better |
| 18 | RXRRXRRXR | IKILFQN | dRRMKWHR | Cys | Cys-K-PNA705-K | | disulfide linked | 0.54±0.08 | |
| 19 | RXRXRXRXR | IKILFQN | RRMKWKK | Cys | Cys-K-PNA705-K | | disulfide linked | 0.72±0.05 | |
| 20 | RBRBRBRBR | IKILFQN | RRMKWHK | Cys | Cys-K-PNA705-K | | disulfide linked | 0.94±0.10 | |
| 21 | RXRRXRRXR | IdKILFQN | dRRMKWHK | BCys | Cys-K-PNA705-K | Pip-2a | disulfide linked | 0.79±0.13 | yes |
| 22 | RXRRXRRXR | IHILFQN | dRRMKWHK | BCys | Cys-K-PNA705-K | Pip-2b | disulfide linked | 0.64±0.07 | yes |
| 23 | RXRRXRRXR | IRILFQN | dRRMKWHK | BCys | Cys-K-PNA705-K | Pip-2c | disulfide linked | 0.51±0.12 | no |
| 24 | RXRRXRRXR | IdKILFQY | dRRMKWHK | BCys | Cys-K-PNA705-K | Pip-3a | disulfide linked | 0.59±0.05 | yes |
| 25 | RXRRXRRXR | LYSPLSFQ | dRRMKWHK | BCys | Cys-K-PNA705-K | Pip-3b | disulfide linked | 0.87±0.10 | yes |
| 26 | RXRRXRRXR | ISILFQY | dRRMKWHK | BCys | Cys-K- | Pip-4a | disulfide | 1.7±0.4 | |

Figure 15 (cont)

| | | | | | | | |
|---|---|---|---|---|---|---|---|
| 27 | RXRRXRRXR | ILFQY | dRRMKWHK | BCys | PNA705-K | Pip-4b | linked | 0.62±0.08 |
| 28 | RXRRXRIdR | ILFQY | dRRMKWHK | BCys | Cys-K-PNA705-K | Pip-4c | disulfide linked | 0.73±0.03 |
| 29 | RXRRBRRXR | IHILFQY | dRRMKWHK | BCys | Cys-K-PNA705-K | Pip-4f | disulfide linked | |
| 30 | RBRRXRRBR | IHILFQY | dRRMKWHK | BCys | Cys-K-PNA705-K | Pip-4e | disulfide linked | |
| 31 | RXRRXRRXR | IHILFQY | dRHMKWHK | BCys | Cys-K-PNA705-K | Pip-4d | disulfide linked | >2 |
| 208 | RXRRBRRXR | ILFQY | dRHMKWHK | BCys | Cys-K-PNA705-K | Pip-5a | | 0.91±0.05 |
| 209 | RXRRBRRXR | ILFQY | dKRMKWHK | BCys | Cys-K-PNA705-K | Pip-5b | | 0.63±0.01 |
| 210 | RXRRBRRXR | ILFQY | dRRWKWHK | BCys | Cys-K-PNA705-K | Pip-5c | | 0.54±0.06 |
| 32 | RXRRXRRXR | IdKILFQN | dRRMKWHK | BCys | CH2-CO-K-PNADMD-K | Pip-2a | thioether linked DMD studies | |
| 33 | RXRRXRRXR | IHILFQN | dRRMKWHK | BCys | CH2-CO-K-PNADMD-K | Pip-2b | thioether linked DMD studies | |

Figure 15 (cont)

Natural amino acids:
G = Glycine (Gly)
R = Arginine (Arg)
K = Lysine (Lys)
Q = Glutamine (Gln)
I = Isoleucine (Ile)
W = Tryptophan (Trp)
F = Phenylalanine (Phe)
N = Asparagine (Asn)
H = Histidine (His)
Y = Tyrosine (Tyr)
S = Serine (Ser)
L = Leucine (Leu)
Cys= Cysteine PNA705 18-mer
PNADMD 20-mer Notes:
Non-natural amino acids:
X=aminohexanoyl
B=betaAla
hR=homoArg
d = D-aminoacid

Figure 15 (cont)

|  | SEQ ID NO |  | SEQ ID NO |
|---|---|---|---|
| RXRRXRRXRIKILFQNRRMKWHK | 34 | RXRRXRRXRIKILFQNdRRMKWHK | 35 |
| RXRRXRRXRIdKILFQNRRMKWHK | 36 | RXRRXRRXRIdKILFQNdRRMKWHK | 37 |
| RXRRXRRXRIHILFQNRRMKWHK | 38 | RXRRXRRXRIHILFQNdRRMKWHK | 39 |
| RXRRXRRXRIRILFQNRRMKWHK | 40 | RXRRXRRXRIRILFQNdRRMKWHK | 41 |
| RXRRXRRXRIILFQNRRMKWHK | 42 | RXRRXRRXRIILFQNdRRMKWHK | 43 |
| RXRRXRRXRKILFQNRRMKWHK | 44 | RXRRXRRXRKILFQNdRRMKWHK | 45 |
| RXRRXRRXRdKILFQNRRMKWHK | 46 | RXRRXRRXRdKILFQNdRRMKWHK | 47 |
| RXRRXRRXRHILFQNRRMKWHK | 48 | RXRRXRRXRHILFQNdRRMKWHK | 49 |
| RXRRXRRXRRILFQNRRMKWHK | 50 | RXRRXRRXRRILFQNdRRMKWHK | 51 |
| RXRRXRRXRILFQNRRMKWHK | 52 | RXRRXRRXRILFQNdRRMKWHK | 53 |
| RXRRXRRXRIKILFQYRRMKWHK | 54 | RXRRXRRXRIKILFQYdRRMKWHK | 55 |
| RXRRXRRXRIdKILFQYRRMKWHK | 56 | RXRRXRRXRIdKILFQYdRRMKWHK | 57 |
| RXRRXRRXRIHILFQYRRMKWHK | 58 | RXRRXRRXRIHILFQYdRRMKWHK | 59 |
| RXRRXRRXRIRILFQYRRMKWHK | 60 | RXRRXRRXRIRILFQYdRRMKWHK | 61 |
| RXRRXRRXRIILFQYRRMKWHK | 62 | RXRRXRRXRIILFQYdRRMKWHK | 63 |
| RXRRXRRXRKILFQYRRMKWHK | 64 | RXRRXRRXRKILFQYdRRMKWHK | 65 |
| RXRRXRRXRdKILFQYRRMKWHK | 66 | RXRRXRRXRdKILFQYdRRMKWHK | 67 |
| RXRRXRRXRHILFQYRRMKWHK | 68 | RXRRXRRXRHILFQYdRRMKWHK | 69 |
| RXRRXRRXRRILFQYRRMKWHK | 70 | RXRRXRRXRRILFQYdRRMKWHK | 71 |
| RXRRXRRXRILFQYRRMKWHK | 72 | RXRRXRRXRILFQYdRRMKWHK | 73 |

X=aminohexanoyl
B=betaAla
hR=homoArg
d = D-aminoacid

Figure 16

| SEQ ID NO. | Domain 1 | Domain 2 | Domain 3 | Domain 4 (linker) | PNA Cargo | Name | Exon Skipping Activity | |
|---|---|---|---|---|---|---|---|---|
| | | | | | | | 1µM | 2µM |
| 211 | RXRRXRXRRXR | | | Cys | CH₂-CO-K-PNADMD-K | (RXR)₄ | 0 | 13±1 |
| 212 | RXRRXRRRXR | IdKILFQN | dRRMKWHK | BCys | CH₂-CO-K-PNADMD-K | Pip-2a | 23±5 | 36±3 |
| 213 | RXRRXRRRXR | IHILFQN | dRRMKWHK | BCys | CH₂-CO-K-PNADMD-K | Pip-2b | 17±2 | 34±1 |
| 214 | RXRRXRRRXR | IdKILFQY | dRRMKWHK | BCys | CH₂-CO-K-PNADMD-K | Pip-3a | 17±1 | 28±2 |
| 215 | RXRRXRRRXR | LYSPLSFQ | dRRMKWHK | BCys | CH₂-CO-K-PNADMD-K | Pip-3b | 12±2 | 25±5 |
| 216 | RXRRXRRRXR | ILFQY | dRRMKWHK | BCys | CH₂-CO-K-PNADMD-K | Pip-4b | 20±5 | 34±3 |
| 217 | RXRRXRIdR | ILFQY | dRRMKWHK | BCys | CH₂-CO-K-PNADMD-K | Pip-4c | 18±4 | 34±3 |
| 218 | RBRRXRRBR | ILFQY | dRRMKWHK | BCys | CH₂-CO-K-PNADMD-K | Pip-4e | 22±6 | 34±2 |
| 219 | RXRRBRRXR | ILFQY | dRRMKWHK | BCys | CH₂-CO-K-PNADMD-K | Pip-4f | 23±3 | 30±3 |
| 220 | RBRRXRRBR | ILFQY | dRRMKWHK | BCys | CH₂-CO-K-PNADMD-K | Pip-4g | 16±6 | 34±4 |
| 221 | RXRRBRRXR | ILFQY | dRRMKWHK | BCys | CH₂-CO-K-PNADMD-K | Pip-4h | 22±4 | 32±3 |
| 222 | RXRRBRRXR | ILFQY | dRHMKWHK | BCys | CH₂-CO-K-PNADMD-K | Pip-5a | 9±3 | 33±3 |

Figure 17

| | | | | | | | |
|---|---|---|---|---|---|---|---|
| 223 | RXRRBRXR | ILFQY | dRAMKWHK | BCys | CH₂-CO-K-PNADMD-K | Pip-5b | 9±4 | 36±1 |
| 224 | RXRRBRAXR | ILFQY | dRPWKWHK | BCys | CH₂-CO-K-PNADMD-K | Pip-5c | 15±1 | 29±3 |
| 225 | RXRRBRAXR | ILFQY | dKHWKWHK | BCys | CH₂-CO-K-PNADMD-K | Pip-5d | 11±1 | 23±2 |
| 226 | RXRRBRAXR | ILFQY | RXRBRXR | BCys | CH₂-CO-K-PNADMD-K | Pip-5e | 13±4 | 35 |
| 227 | RXRRBRAXR | ILFQY | RXRXRXR | BCys | CH₂-CO-K-PNADMD-K | Pip-5f | 11±3 | 31±4 |
| 228 | RXRRBRAXR | ILQY | dRAMKWHK | BCys | CH₂-CO-K-PNADMD-K | Pip-5g | 12±4 | 32±4 |
| 229 | RXARXR | ILFQY | RXPRXR | Cys | CH₂-CO-K-PNADMD-K | Pip-5h | 8±1 | 22±4 |

PNADMD 20-mer

Notes:
Non-natural amino acids:
X=aminohexanoyl
B=betaAla
hR=homoArg
d = D-aminoacid Natural amino acids:
G = Glycine (Gly)
R = Arginine (Arg)
K = Lysine (Lys)
Q = Glutamine (Gln)
I = Isoleucine (Ile)
W = Tryptophan (Trp)
F = Phenylalanine (Phe)
N = Asparagine (Asn)
H = Histidine (His)
Y = Tyrosine (Tyr)
S = Serine (Ser)
L = Leucine (Leu)
Cys= Cysteine

Figure 17 (cont)

| SEQ ID NO. | Domain 1 | Domain 2 | Domain 3 | Domain 4 (linker) | PMO Cargo | Name | Exon Skipping Activity | | |
|---|---|---|---|---|---|---|---|---|---|
| | | | | | | | 0.5μM | 1μM | 2μM |
| 230 | RXRRBRXR | ILFQY | RXRBRXR | BCys | PMODMD | Pip-5e | 43±8 | 64±3 | 69±4 |
| 231 | RXRRBRRXR | ILFQY | RXRXRXR | BCys | PMOMD | Pip-5f | 24±2 | 37±1 | 66±5 |
| 232 | RXRRBRRXR | ILIQY | dRRMKWHK | BCys | PMODMD | Pip-5g | 24±1 | 62±4 | 70±4 |
| 233 | RXRXR | ILFQY | RXRRXR | Cys | PMODMD | Pip-5h | 4±1 | 4±1 | 11±2 |
| 234 | RBRXRRBR | ILFQY | RBRXRBR | BCys | PMODMD | Pip-5j | 40±5 | 58±5 | 68±4 |
| 235 | RBRXRRBR | ILFQY | RXRBRXR | BCys | PMODMD | Pip-5i | 35±2 | 64±3 | 69±4 |
| 236 | RBRXRRBR | ILFQY | RXRXR | BCys | PMODMD | Pip-5k | 37±3 | 46±3 | 59±4 |
| 237 | RBRXRRBR | ILFQY | RXRBRX | BCys | PMODMD | Pip-5m | 23±1 | 33±3 | 48±2 |
| 238 | RXRRBRRXR | ILFQY | RXRXR | BCys | PMODMD | Pip-5n | 17±2 | 52±3 | 73±3 |
| 239 | RXRBRRXR | ILFQY | RXRBRX | BCys | PMODMD | Pip-5o | 15±3 | 32±5 | 63±1 |
| 240 | RXRRBRXR | IHILFQN | dRRMKWHK | BCys | PMODMD | Pip-2b | 25±4 | 37±2 | 58±4 |
| 241 | RXRRBR | | RXRRBRX | BCys | PMODMD | B | 36±11 | 45±3 | 57±1 |

Notes:
Non-natural amino acids:
X=aminohexanoyl
B=betaAla
hR=homoArg
d = D-aminoacid Natural amino acids:
G = Glycine (Gly)
R = Arginine (Arg)
K = Lysine (Lys)
Q = Glutamine (Gln)
I = Isoleucine (Ile)
W = Tryptophan (Trp)
F = Phenylalanine (Phe)
N = Asparagine (Asn)
H = Histidine (His)
Y = Tyrosine (Tyr)
S = Serine (Ser)
L = Leucine (Leu)
Cys= Cysteine

Figure 18

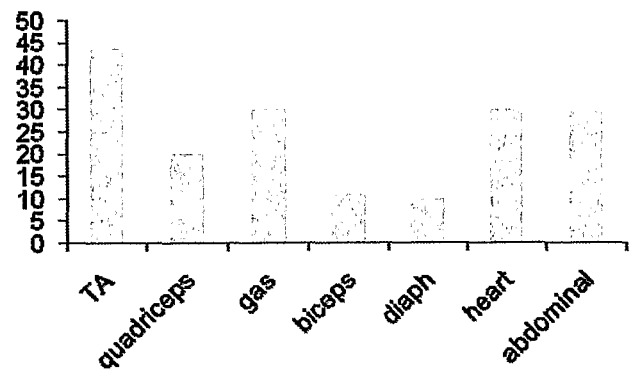
Pip2b-PNA-20
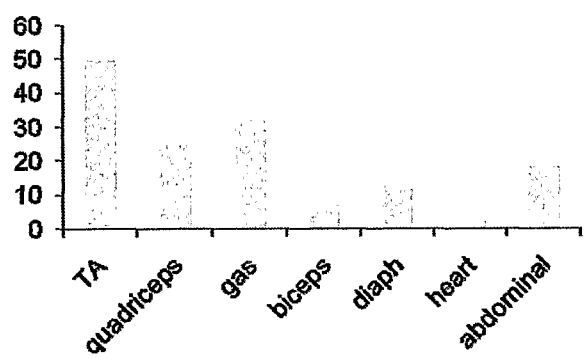
RXR4-PNA-20
Figure 19

| Sequence | SEQ ID NO | Sequence | SEQ ID NO | Sequence | SEQ ID NO |
|---|---|---|---|---|---|
| RXRRBRXRILFQYdRHMKWHK | 242 | RBRRXRRBRILFQYdRHMKWHK | 260 | RXRRXRILFQYdRHMKWHK | 278 |
| RBRRBRXRILFQYdRKMKWHK | 243 | RBRRXRRBRILFQYdKRMKWHK | 261 | RXRRXRILFQYdkRMKWHK | 279 |
| RXRBRXRILFQYdRMKWHK | 244 | RBRRXRRBRILFQYdRMKWHK | 262 | RXRRXRILFQYdRMKWHK | 280 |
| RXRBRXRILFQYdRMKWHK | 245 | RBRRXRRBRILFQYdRMKWHK | 263 | RXRRXRILFQYdRMKWHK | 281 |
| RXRBRXRILFQYXRBRXR | 246 | RBRRXRRBRILFQYXRBRXR | 264 | RXRRXRILFQYXRBRXR | 282 |
| RXRBRXRILFQYXRXRXR | 247 | RBRRXRRBRILFQYXRXRXR | 265 | RXRRXRILFQYXRXRXR | 283 |
| RXRBRXRILFQYXRXRXR | 248 | RBRRXRRBRILFQYXRXRXR | 266 | RXRRXRILFQYXRXRXR | 284 |
| RXRBRXRILFQYXRBRXR | 249 | RBRRXRRBRILFQYRBRXRBR | 267 | RXRRXRILFQYRBRXRBR | 285 |
| RXRBRXRILFQYXRBRX | 250 | RBRRXRRBRILFQYXRBRX | 268 | RXRRXRILFQYXRBRX | 286 |
| RXRRBRXRILQYdRHMKWHK | 251 | RBRRXRRBRILQYdRHMKWHK | 269 | RXRRXRILQYdRHMKWHK | 287 |
| RXRBRXRILQYdKRMKWHK | 252 | RBRRXRRBRILQYdKRMKWHK | 270 | RXRRXRILQYdKRMKWHK | 288 |
| RXRBRXRILQYdRMKWHK | 253 | RBRRXRRBRILQYdRMKWHK | 271 | RXRRXRILQYdRMKWHK | 289 |
| RXRBRXRILQYdRMKWHK | 254 | RBRRXRRBRILQYdRMKWHK | 272 | RXRRXRILQYdRMKWHK | 290 |
| RXRBRXRILQYXRBRXR | 255 | RBRRXRRBRILQYXRBRXR | 273 | RXRRXRILQYXRBRXR | 291 |
| RXRBRXRILQYXRXRXR | 256 | RBRRXRRBRILQYXRXRXR | 274 | RXRRXRILQYXRXRXR | 292 |
| RXRBRXRILQYXRXRXR | 257 | RBRRXRRBRILQYXRXRXA | 275 | RXRRXRILQYXRXRXR | 293 |
| RXRBRXRILQYRBRXR | 258 | RBRRXRRBRILQYRBRXRBR | 276 | RXRRXRILQYRBRXRBR | 294 |
| RXRBRXRILQYXRBRX | 259 | RBRRXRRBRILQYXRBRX | 277 | RXRRXRILQYXRBRX | 295 |

Notes:
X = aminohexanoyl
B = betaAla
hR = homoArg
d = D-aminoacid

Figure 25

CELL PENETRATING PEPTIDES

FIELD OF THE INVENTION

The present invention relates to peptides particularly, although not exclusively, to cell penetrating peptides and to conjugates of a cell penetrating peptide and a cargo molecule.

BACKGROUND TO THE INVENTION

Oligonucleotides (ONs) that target essential RNA sequences have found numerous recent applications in the modulation of gene expression in cells and as potential therapeutics[1,2]. A mechanistic advantage of steric blocking ONs over RNase H-inducing antisense ONs and RISC-inducing siRNA reagents is greater specificity, since binding of an ON to an incorrect RNA is unlikely to trigger an undesired off-target biological effect. Secondly, a much wider range of synthetic ON analogues may be used, since there is no requirement for molecular recognition by a host RNA-cleaving enzyme.

Foremost amongst ON analogues useful as steric blocking agents are those with uncharged backbones, such as peptide nucleic acids (PNA)[3] and phosphorodiamidate morpholino oligonucleotides (PMO)[4]. Both PNA and PMO ONs have been used in vivo for RNA targeting applications towards the development of therapeutics[5]. In cell culture, both PNA and PMO are observed to enter cells only rather poorly and therefore much effort has been expended to develop methods of enhancing cell delivery. Particularly useful has been the attachment of cell penetrating peptides (CPP), such as Penetratin, Tat (48-60), Transportan, and (R-AhX-R)$_4$ (Ahx=aminohexanoyl) in the hope that their observed cell translocating power as peptides can be utilized when conjugated to PNA or PMO[6,9]

A valuable assay for assessing the activity of steric blocking ONs is that established by Kole and colleagues which involves splice correction of an aberrant thalassemia β-globin intron by a 18-mer synthetic ON (705 site) in the nucleus of HeLa pLuc705 cells and subsequent up-regulation of reporter firefly luciferase[10]. This assay has a very high dynamic range, such that even very low activity levels can be measured as a positive luminescence read-out. CPP-PNA conjugates targeted to the 705 splice site have been tested in this assay and moderate activity levels have been reported for several different CPPs when the CPP-PNA conjugate is incubated with HeLa pLuc705 cells in the absence of an added transfection agent, whereas PNA alone is inactive[11-13]. In our laboratories, we found that whereas Tat-PNA or (Lys)$_8$-PNA conjugates required co-incubation with 100 μM chloroquine, an endosomolytic agent, in order to see significant activity in the assay[14,15], activity in the μM range for the (R-Ahx-R)$_4$-PNA and (R-Ahx-R)$_4$-PMO constructs could be obtained in the absence of chloroquine[7,16].

We have also reported a new CPP in which six Arg residues were added to the N-terminus of the known CPP Penetratin[17, 18]. R$_8$-Penetratin (R6Pen) disulfide-conjugated to a PNA complementary to the trans-activation responsive element RNA of HIV-1 showed significant activity in a HeLa cell luciferase reporter assay of inhibition of Tat-dependent trans-activation that required nuclear delivery and binding to TAR RNA in order to inhibit luciferase expression[18].

Duchenne muscular dystrophy (DMD) is an X-linked muscle disorder caused mainly by nonsense or frame-shift mutations in the dystrophin gene, occurring with a frequency of about 1 in 3500 live male births and potential therapies are badly needed[29]. DMD patients suffer from severe, progressive muscle wasting, whereas the milder Becker muscular dystrophy is caused by in-frame deletions resulting in expression of a shortened but partially functional protein. Sequence-specific antisense oligonucleotides (ON) have been shown to induce targeted exon skipping to correct the reading frame of mutated dystrophin mRNA such that shorter dystrophin forms are produced with activity similar to that of Becker muscular dystrophy[30,31]. Studies have been carried out in cell models, in an mdx dystrophic mouse model containing a nonsense mutation in exon 23[31-33], and in a dog model that have shown outstanding promise for the exon skipping approach. Biological activity is achieved as a result of binding of the ON to the dystrophin pre-mRNA in the muscle cell nuclei to cause alteration of splicing patterns by a "steric block" mechanism.

One of the most important factors determining the efficiency of exon skipping is the ON chemistry. The most widely used has been 2'-O-methyl phosphorothioate (2'OMePS). This backbone is being used in a Phase I clinical trial targeting exon 51 of dystrophin pre-mRNA in DMD patients involving intramuscular injection[34]. A similar Phase I trial is being carried out using a phosphorodiamidate morpholino oligonucleotide (PMO)[35]. Studies in vivo have suggested higher levels of exon skipping and restoration of dystrophin expression using PMO compared to 2'OmePS[35]. PMOs are non-ionic molecules and are considered less likely to form unwanted interactions with the intracellular molecules of target cells.

Yin and Wood have examined another non-ionic analogue called peptide nucleic acids (PNA) by intramuscular injection into mdx mice and found significant induction of exon skipping and dystrophin production[23]. Both PMO and PNA are considered non-toxic ON analogues with high sequence specificity that have significant potential for pharmaceutical development. So far only PMO has been produced in form licensed for clinical trial use and therapeutic development of PNA has lagged behind.

Several research groups have been working on the design of CPPs (sometimes called membrane translocating peptides) that when conjugated to non-ionic ONs (such as PNA or PMO) aid their delivery into cells (but not ionic types) and hence boost biological activity of the ON. In the case of PMO, a peptide has been disclosed containing both natural and non-natural amino acids (R-Ahx-R)$_4$-Ahx-B that when conjugated to PMO results in higher levels of steric block activity in a number of cell and in vivo models[36]. This has been investigated in mouse mdx DMD studies[37].

In order to be useful for in vivo applications, it is preferred that CPPs demonstrate effective penetration of the cell and nuclear membranes, particularly when attached to a cargo such as PNA or PMO, in order to enable efficacious splice correction, e.g. EC$_{50}$ about 0.90 μM or less as measured by the splice correction luciferase assay of Kole et al. Furthermore, the CPP should have good serum stability in order to resist degradation prior to cell penetration. For therapeutic applications CPPs should also have low toxicity.

SUMMARY OF THE INVENTION

The inventors have identified a series of promising cell penetrating peptides. The peptides may act as carrier moieties to facilitate movement of a cargo across cell and nuclear membranes. Peptide-cargo conjugates are also provided.

Five novel peptide series have been prepared and have been tested as peptide-PNA and peptide-PMO cargo conjugates. The peptides and attached cargoes are shown in FIGS. 15, 16, 17, 18 and 25 and are summarised below:

Pip-1 [SEQ ID NOs: 10-20];
Pip-2a, Pip-2b, Pip-2c [SEQ ID NOs: 21-23];
Pip-3a, Pip-3b [SEQ ID NOs: 24-25];
Pip-4a, Pip-4b, Pip-4c, Pip-4d, Pip-4e, Pip-4f, Pip 4g, Pip-4h [SEQ ID NOs: 26-31 and 216-221];
Pip-5a, Pip-5b, Pip-5c, Pip-5d, Pip-5e, Pip-5f, Pip-5g, Pip-5h, Pip5j, Pip-5k, Pip-5l, Pip-5m, Pip-5n, Pip-5o [SEQ ID Nos: 222-229 and 230-239]

Pip-2a [SEQ ID NO: 21], Pip-2b [SEQ ID NO: 22], Pip-3a [SEQ ID NO: 24], Pip-4b [SEQ ID NO: 27] Pip-4c [SEQ ID NO: 28], Pip-5a [SEQ ID NO: 222], Pip-5b [SEQ ID NO: 223], and Pip-5c [SEQ ID NO: 224] all show high levels of splice correction in a HeLa cell luciferase splice correction assay (FIG. 15) indicating nuclear penetration of the peptide-PNA conjugate and functionality of the PNA molecule.

Pip-2a [SEQ ID NO: 21], Pip-2b [SEQ ID NO: 22] and Pip-3a [SEQ ID NO:24] demonstrate high serum stability (resistance to proteolysis when incubated with serum).

The Pip-5 series (a-o) showed high exon skipping activity in mouse mdx myotubes using both PNADMD and PMODMD (FIGS. 17 and 18).

Accordingly, the cell penetrating peptide component of the CPP-PNA or CPP-PMO conjugate and peptides having substantially similar sequence identity and structure are expected to be useful in facilitating cell and nuclear penetration of cargo such as antisense oligonucleotides including PNA, PMO, siRNA, peptides and proteins, as well as small molecules Accordingly, the present invention provides peptides that are useful in facilitating the uptake of such cargoes across cell membranes, such as the plasma membrane of a mammalian cell and/or the nuclear membrane of a mammalian cell. The peptides may be referred to as "cell penetrating peptides" and may be conjugated to a cargo to facilitate transport of the cargo across the membrane.

Peptides according to the invention have a sequence that is a chemically contiguous single molecule. The peptide sequence may be comprised of amino acids and optional non-amino acids, e.g. aminohexanoyl spacers. For example, in some parts of the peptide an aminohexanoyl spacer may be chemically bonded to the C-terminal end of a first amino acid and to the N-terminal end of a second amino acid, thereby chemically linking the two amino acids.

The peptides may include modified and non-naturally occurring amino acids.

Each peptide comprises or consists of 4 domains in the following linear arrangement:

N-terminus [Domain 1]-[Domain 2]-[Domain 3]-[Domain 4] C-terminus

Each domain has common sequence characteristics but the exact sequence of each domain is capable of variation and modification. Thus a range of sequences is possible for each domain. The combination of each possible domain sequence yields a range of peptide sequences which form part of the present invention.

The core peptide sequence is represented by the contiguous amino acid (and optional spacer) sequence of Domains 1-3. Domain 4 is an optional linker sequence arranged to allow linkage to the cargo. In some embodiments Domain 4 may be absent, e.g. have no sequence.

In the following description the standard one letter amino acid code is used. Non-natural amino acids and spacer molecules are referred to using the following one letter code:
X=aminohexanoyl
B=betaAlanine
hR=homoArginine
d=D-amino acid (D-amino acids may be replaced by L-amino acids)

Domain 1 is an arginine rich sequence and may be 4, 5, 6, 7, 8 or more amino acids in length. Preferably Domain 1 has 6 amino acids. Preferably these are spaced by spacer groups (e.g. aminohexanoyl). Optionally, these spacers are not counted in the number of amino acids present in the domain. Spacer groups may include non-natural methylene rich spacers such as aminohexanoyl, β-alanyl, p-aminobenzoyl, isonipecotyl and 4-aminobutyryl.

Preferably Domain 1 has two or more cationic amino acids with hydrophobic amino acids or spacer groups separating some of the cationic amino acids. In preferred embodiments the cationic amino acid is Arginine (R). Preferably Domain 1 has at least 3 Arginine residues, more preferably at least 4 Arginine residues. In some embodiments Domain 1 contains 5, 6 or more Arginine residues.

Domain 1 preferably has a maximum length of less than 12 residues, more preferably less than 10 residues and a minimum length of 6 residues (the respective lengths may optionally include spacer groups, e.g. X, and non-natural amino acids). Preferred Domain 1 sequences are chosen from the group of:

| | |
|---|---|
| $(RXR)_n$ where n = 2, 3 or 4; | [SEQ ID NOs: 74-76] |
| $(RBR)_n$ where n = 2, 3 or 4; | [SEQ ID NOs: 77-79] |
| RXRRXRIdR; | [SEQ ID NO: 80] |
| RXRRBRRXR; | [SEQ ID NO: 81] |
| RBRRXRRBR; or | [SEQ ID NO: 82] |
| $(R)_m$ where m = 5, 6, 7 or 8; | [SEQ ID NOs: 83-85 and 301] |

Domain 2 contains the amino acid sequence ILFQ [SEQ ID NO: 86], or ILIQ [SEQ ID NO:202]. More preferably Domain 2 contains the amino acid sequence ILFQN [SEQ ID NO: 87] or ILFQY [SEQ ID NO: 88], ILIQN [SEQ ID NO:304] or ILIQY [SEQ ID NO:296]. The ILFQ or ILIQ sequence may contain 1, 2, 3, 4 or 5 additional amino acids at one or both of the N- or C-terminal ends of the sequence. Preferably there are none, one or two amino acids at the N-terminal end and none, one or two amino acids at the C-terminal end. As such, Domain 2 may be 4, 5, 6, 7, 8, 9 or 10 amino acids in length. Domain 2 is preferably a hydrophobic domain.

Domain 2 preferably has a maximum length of less than 10 residues, more preferably less than 7 residues and a minimum length of 3 residues, more preferably 4 residues (the respective lengths may optionally include spacer groups, e.g. X, and non-natural amino acids).

The additional amino acids may be of any type. At the N-terminal end of Domain 2 preferred sequences include IdK, IH, IR, IdR, e.g. one hydrophobic and one cationic amino acid. At the C-terminal end of the Domain 2 sequence preferred amino acids include N and Y, e.g. not cationic or hydrophilic.

Generic sequence representations for domain 2 are given below:

```
Domain 2 = Z₂Z₃ILFQZ₄        [SEQ ID NO: 89]

Domain 2 = Z₂Z₃ILIQZ₄        [SEQ ID NO: 297]
```

$Z_2$=I or no amino acid
$Z_3$=K, dK, H, R or no amino acid
$Z_4$=N, Y

Accordingly, preferred Domain 2 sequences are chosen from the group of:

| | SEQ ID NO: | | SEQ ID NO: |
|---|---|---|---|
| IKILFQN | 90 | IKILFQY | 91 |
| IdKILFQN | 92 | IdKILFQY | 93 |
| IHILFQN | 94 | IHILFQY | 95 |
| IRILFQN | 96 | IRILFQY | 97 |
| IILFQN | 98 | IILFQY | 99 |
| KILFQN | 100 | KILFQY | 101 |
| dKILFQN | 102 | dKILFQY | 103 |
| HILFQN | 104 | HILFQY | 105 |
| RILFQN | 106 | RILFQY | 107 |
| ILFQN | 108 | ILFQY | 109 | or the group of:

| | SEQ ID NO: | | SEQ ID NO: |
|---|---|---|---|
| IKILIQN | 135 | IKILIQY | 136 |
| IdKILIQN | 137 | IdKILIQY | 138 |
| IHILIQN | 139 | IHILIQY | 140 |
| IRILIQN | 141 | IRILIQY | 142 |
| IILIQN | 143 | IILIQY | 144 |
| KILIQN | 145 | KILIQY | 146 |
| dKILIQN | 147 | dKILIQY | 148 |
| HILIQN | 149 | HILIQY | 150 |
| RILIQN | 151 | RILIQY | 152 |
| ILIQN | 153 | ILIQY | 154 |

Domain 3 is a cationic domain and preferably has a sequence chosen from:

```
RRMKWHK           [SEQ ID NO: 110]

dRRMKWHK          [SEQ ID NO: 111]

dRHMKWHK,         [SEQ ID NO: 155]

dKRMKWHK,         [SEQ ID NO: 156]

dRRWKWHK,         [SEQ ID NO: 157]

dKHWKWHK,         [SEQ ID NO: 158]

RXRBRXR,          [SEQ ID NO: 159]

RXRXRXR,          [SEQ ID NO: 160]

RXRRXR,           [SEQ ID NO: 161]

RBRXRBR,          [SEQ ID NO: 162]

RXRBRX,           [SEQ ID NO: 163]
or
(RXR)ₙ where n = 2,   [SEQ ID NOs: 74-76]
3 or 4;.
```

Preferably Domain 3 has two or more cationic amino acids with hydrophobic amino acids or spacer groups separating some of the cationic amino acids. In preferred embodiments the cationic amino acid is Arginine (R). Preferably Domain 3 has at least 3 Arginine residues, more preferably at least 4 Arginine Residues. In some embodiments Domain 3 contains 4, 5, 6 or more Arginine residues.

In some embodiments Domain 3 has a minimum length of 4 amino acids and a maximum length of 15 amino acids (optionally excluding spacer groups, e.g. X, and and non-natural amino acids). In some embodiments the minimum length, including spacer groups, is 5 or more and the maximum length, including spacer groups, is 9 or less.

The use of aminohexanoyl and betaAlanine in Domains 1 and 3 is advantageous in that it helps minimise the immunogenicity of the peptide.

Domain 4 is a linker sequence arranged to allow chemical linkage of the peptide to the cargo. The Domain 4 sequence may also act as a spacer to separate the Domain 1-3 part of the peptide from the cargo. A range of linker sequences are possible, including sequences having a C-terminal Cysteine residue that permits formation of a disulphide, thioether or thiol-maleimide linkage. Other ways of linking the peptide to the cargo include use of a C-terminal aldehyde to form an oxime, use of a click reaction or formation of a morpholino linkage with a basic amino acid on the peptide which may be followed by a spacer sequence before Domain 3 comprising: X or B or XB or BX.

The Domain 4 linker sequence may be 1, 2, 3, 4 or 5 or more amino acids in length (including spacer groups). The Domain 4 linker sequence may be chosen from the group of: BCys, XCys, Cys, GGCys, BXCys, BXCys, XBCys, X,XX,B,BB, BX or XB. Any B or X may be replaced by another spacer, which, for example, may be chosen from 4-aminobutyryl (Aib) and isonicopecotyl.

The linker sequence of Domain 4 may form part of the cargo to which the peptide is to be attached. In some embodiments attachment of the cargo is directly to the C-terminus of the Domain 3 sequence. As such, in some embodiments no Domain 4 sequence is required, or it is provided by linkage of the cargo and Domain 3 sequence.

In accordance with the above, peptides according to the invention may be represented as follows:

$Z_1Z_2Z_3$ILFQ$Z_4Z_5$RMKWHK$Z_6$ [SEQ ID NO: 112]

$Z_1Z_2Z_3$ILFQ$Z_4Z_5$HMKWHK$Z_6$ [SEQ ID NO: 164]

$Z_1Z_2Z_3$ILFQ$Z_4Z_5$RWKWHK$Z_6$ [SEQ ID NO: 165]

$Z_1Z_2Z_3$ILFQ$Z_4Z_5$HWKWHK$Z_6$ [SEQ ID NO: 166]

-continued

| | |
|---|---|
| $Z_1Z_2Z_3$ILFQ$Z_4$RXRBRX$RZ_6$ | [SEQ ID NO: 167] |
| $Z_1Z_2Z_3$ILFQ$Z_4$RXRXRX$RZ_6$ | [SEQ ID NO: 168] |
| $Z_1Z_2Z_3$ILFQ$Z_4$RXRRX$RZ_6$ | [SEQ ID NO: 169] |
| $Z_1Z_2Z_3$ILFQ$Z_4$RBRXRB$RZ_6$ | [SEQ ID NO: 170] |
| $Z_1Z_2Z_3$ILFQ$Z_4$RXRBRX$RZ_6$ | [SEQ ID NO: 171] |
| $Z_1Z_2Z_3$ILFQ$Z_4$RXRBRX$Z_6$ | [SEQ ID NO: 172] |
| $Z_1Z_2Z_3$ILIQ$Z_4Z_5$RMKWHK$Z_6$ | [SEQ ID NO: 173] |
| $Z_1Z_2Z_3$ILIQ$Z_4Z_5$HMKWHK$Z_6$ | [SEQ ID NO: 174] |
| $Z_1Z_2Z_3$ILIQ$Z_4Z_5$RWKWHK$Z_6$ | [SEQ ID NO: 175] |
| $Z_1Z_2Z_3$ILIQ$Z_4Z_5$HWKWHK$Z_6$ | [SEQ ID NO: 176] |
| $Z_1Z_2Z_3$ILIQ$Z_4$RXRBRX$RZ_6$ | [SEQ ID NO: 177] |
| $Z_1Z_2Z_3$ILIQ$Z_4$RXRXRX$RZ_6$ | [SEQ ID NO: 178] |
| $Z_1Z_2Z_3$ILIQ$Z_4$RXRRX$RZ_6$ | [SEQ ID NO: 179] |
| $Z_1Z_2Z_3$ILIQ$Z_4$RBRXRB$RZ_6$ | [SEQ ID NO: 180] |
| $Z_1Z_2Z_3$ILIQ$Z_4$RXRBRX$RZ_6$ | [SEQ ID NO: 181] |
| $Z_1Z_2Z_3$ILIQ$Z_4$RXRBRX$Z_6$ | [SEQ ID NO: 182] | and preferred peptides have the sequence:

| | |
|---|---|
| $Z_1Z_2Z_3$ILFQ$Z_4Z_5$RMKWHK | [SEQ ID NO: 113] |
| $Z_1Z_2Z_3$ILFQ$Z_4Z_5$HMKWHK | [SEQ ID NO: 183] |
| $Z_1Z_2Z_3$ILFQ$Z_4Z_5$RWKWHK | [SEQ ID NO: 184] |
| $Z_1Z_2Z_3$ILFQ$Z_4Z_5$HWKWHK | [SEQ ID NO: 185] |
| $Z_1Z_2Z_3$ILFQ$Z_4$RXRBRXR | [SEQ ID NO: 186] |
| $Z_1Z_2Z_3$ILFQ$Z_4$RXRXRXR | [SEQ ID NO: 187] |
| $Z_1Z_2Z_3$ILFQ$Z_4$RXRRXR | [SEQ ID NO: 188] |
| $Z_1Z_2Z_3$ILFQ$Z_4$RBRXRBR | [SEQ ID NO: 189] |
| $Z_1Z_2Z_3$ILFQ$Z_4$RXRBRXR | [SEQ ID NO: 190] |
| $Z_1Z_2Z_3$ILFQ$Z_4$RXRBRX | [SEQ ID NO: 191] |
| $Z_1Z_2Z_3$ILIQ$Z_4Z_5$RMKWHK | [SEQ ID NO: 192] |
| $Z_1Z_2Z_3$ILIQ$Z_4Z_5$HMKWHK | [SEQ ID NO: 193] |
| $Z_1Z_2Z_3$ILIQ$Z_4Z_5$RWKWHK | [SEQ ID NO: 194] |
| $Z_1Z_2Z_3$ILIQ$Z_4Z_5$HWKWHK | [SEQ ID NO: 195] |
| $Z_1Z_2Z_3$ILIQ$Z_4$RXRBRXR | [SEQ ID NO: 196] |
| $Z_1Z_2Z_3$ILIQ$Z_4$RXRXRXR | [SEQ ID NO: 197] |
| $Z_1Z_2Z_3$ILIQ$Z_4$RXRRXR | [SEQ ID NO: 198] |
| $Z_1Z_2Z_3$ILIQ$Z_4$RBRXRBR | [SEQ ID NO: 199] |
| $Z_1Z_2Z_3$ILIQ$Z_4$RXRBRXR | [SEQ ID NO: 200] |
| $Z_1Z_2Z_3$ILIQ$Z_4$RXRBRX | [SEQ ID NO: 201] |

Wherein:
$Z_1$=(RXR)$_n$ where n=2, 3, or 4; (RBRX, where n=2, 3, or 4; (R)$_m$ where m=5, 6, 7 or 8; RXRRXRIdR [SEQ ID NO: 80]; RXRRBRRXR [SEQ ID NO: 81]; or RBRRXRRBR [SEQ ID NO: 82];
$Z_2$=I or no amino acid
$Z_3$=K, dK, H, R or no amino acid
$Z_4$=N, Y
$Z_5$=R or dR, K or dK
$Z_6$=linker Preferred peptides may comprise, or consist of, a sequence chosen from one of SEQ ID NOs 10-33 or SEQ ID NOs: 208-210 (FIG. 15), SEQ ID NOs: 34-73 (FIG. 16) or SEQ ID NOs:242-295 (FIG. 25), SEQ ID NOs: 112 or 113 or SEQ ID NOs:164-201. Preferred peptides may have a Domain 4 linker sequence at the C-terminal end of one of BCys, XCys, Cys, GGCys, BBCys, BXCys or XBCys, X, XX, B, BB, BX or XB.

Peptides according to the present invention may be chosen from any one of SEQ ID NOs: 34-73 or SEQ ID NOs:242-295.

Excluding the cargo molecule, peptides according to the present invention may have a maximum length of 30 amino acids, more preferably one of 15, 16, 17, 18, 19, 20, 21, 22, 23, 24, 25, 26, 27, 28, 29, 30 amino acids and a minimum length of 10 amino acids, more preferably one of 10, 11, 12, 13, 14, 15, 16, 17, 18, 19, 20 amino acids (the maximum and minimum length optionally excludes any spacer molecules, e.g. aminohexanoyl groups, but includes non-natural or modified amino acids).

Peptides according to the present invention may be provided as peptide-cargo conjugates where the peptide further comprises a cargo molecule chemically linked (preferably covalently linked) to the peptide at either the N-terminal or C-terminal end of the peptide, preferably at the C-terminal end. Chemical linkage may be via a disulphide bond, thioether or thiol-maleimide linkage.

The cargo molecule may be any small molecule, e.g. small molecule drug, peptide, cyclic peptide, protein, pharmaceutical or therapeutic (e.g. molecular weight less than 5,000 Da, preferably less than 3000 Da or less than 1000 Da). The cargo molecule may be a nucleic acid, antisense oligonucleotide (such as PNA, PMO, LNA), or siRNA. Preferred cargo molecules are electrically neutral oligonucleotide analogues such as PNA or PMO.

In one embodiment the cargo is PNA705 (SEQ ID NO: 114). In another embodiment the cargo is PNADMD (SEQ ID NO: 115). In another embodiment the cargo is PMODMD [SEQ ID NO:206]. The cargo molecule may have at least 80%, preferably at least 90%, sequence identity to one of PNADMD [SEQ ID NO:115] or PMODMD [SEQ ID NO:206]. Lysine residues may be added to one or both ends of these PNA or PMO molecules to improve water solubility. Cysteine may be added at the N-terminus to allow for disulphide bond formation or bromoacetylation for thioether conjugation Peptides according to the present invention may be provided in isolated or purified form, with or without a cargo molecule.

Derivatives of the peptides also form part of the present invention. Peptide derivatives include variants of a given peptide sequence (e.g. one of SEQ ID NOs: 10-33 or SEQ ID NOs:208-210 or SEQ ID NOs:34-73 or SEQ ID NOs:242-295) which have substantial amino acid sequence identity (e.g. 90%, 91%, 92%, 93%, 94%, 95%, 96%, 97%, 98%, 99% or 100%) to the full length peptide and preferably have the same or better splice correction activity and/or serum stability. Peptide derivatives may have 1, 2 or 3 amino acids or spacer molecules more or less than one of SEQ ID NOs: 10-33 or SEQ ID NOs:208-210 or SEQ ID NOs:34-73 or SEQ ID NOs:242-295.

Percentage (%) sequence identity is defined as the percentage of amino acid residues (optionally including spacer groups) in a candidate sequence that are identical with residues in the given listed sequence (referred to by the SEQ ID NO.) after aligning the sequences and introducing gaps if necessary, to achieve the maximum sequence identity, and not considering any conservative substitutions as part of the sequence identity. Sequence identity is preferably calculated over the entire length of the respective sequences.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

Peptide derivatives may also comprise conservative amino acid replacements which, for example, may be between amino acids within the following groups:
(i) glycine, alanine, serine, threonine;
(ii) glutamic acid and aspartic acid;
(iii) arginine, histidine and lysine;
(iv) asparagine and glutamine;
(v) isoleucine, leucine and valine;
(vi) phenylalanine, tyrosine and tryptophan.

Peptides according to the present invention preferably show high activity in the HeLa cell splicing correction model of Kole et al[10]. Preferably the $EC_{50}$ established in this assay is less than 1 µM, more preferably less than 0.9 µM, more preferably less than 0.8 µM, still more preferably less than 0.7 µM, still more preferably less than 0.6 µM. Peptides according to the present invention preferably exhibit higher or the same activity (i.e. they have a lower or same $EC_{50}$) in the HeLa cell splicing correction model as one of R6Pen or (R-Ahx-R)$_4$.

Peptides according to the present invention preferably exhibit increased serum stability after one hour in serum (e.g. mouse or human serum) compared to R6Pen and preferably equivalent or better serum stability than (R-Ahx-R)$_4$. Serum stability may be measured in PBS containing 20% mouse serum at 37° C. with 10 µL aliquots taken at 0, 15, 30, 60 and 120 min, and diluted with 50 µL 10% DCA in $H_2O/CH_3CN$ (50/50). Samples are mixed and kept at −20° C., the precipitated serum proteins separated by centrifugation (13000 rpm, 5 min) and the supernatant analysed for peptide degradation by MALDI-TOF mass spectrometry.

In the peptides and peptide conjugates of the present invention, amino acids, amino acid spacers and cargo molecules are all preferably chemically linked by covalent bonds.

Peptides and peptide-cargo conjugates according to the present invention may be provided for use in a method of medical treatment. The medical treatment may preferably require delivery of the cargo molecule into a cell and optionally the nucleus of the cell.

Peptides and/or peptide-cargo conjugates are accordingly provided for use in treatment of disease. The use of a peptide and/or a peptide-cargo conjugate in the manufacture of a medicament for the treatment of disease is also provided. A method of treatment of a patient or subject in need of treatment for a disease condition is also provided comprising the step of administering a therapeutically effective amount of a peptide and/or a peptide-cargo conjugate to the patient or subject. Preferably, the cargo component of a peptide-cargo conjugate comprises an active agent (e.g. pharmaceutical agent) capable of treating, preventing or ameliorating the disease.

Diseases to be treated may include any disease where improved penetration of the cell and/or nuclear membrane by a pharmaceutical or therapeutic molecule may lead to an improved therapeutic effect. Diseases to be treated may include disease conditions caused by (in whole or in part) splicing deficiencies, e.g. Duchenne Muscular Dystrophy (DMD), Menkes Disease[38], β-thalassemia[39], splice correction of tau protein to relieve frontotemporal dementia, parkinsonism and spinal muscular atrophy[39], Hutchinson-Gilford Progeria Syndrome[40], Ataxia-telangiectasia mutated (ATM)[41], or cancer. In such cases the peptide cargo may comprise an oligonucleotide, PNA, PMO or LNA capable of preventing or correcting the splicing defect and/or increasing the production of (e.g. number of) correctly spliced mRNA molecules.

Peptides according to the present invention conjugated to either PNADMD or PMODMD have shown superb efficacy in splice correction in heart and abdominal muscle leading to production of dystrophin fibres. As heart failure and lung failure are major causes of death in patients suffering from DMD, peptides according to the present invention are particularly useful in the treatment of DMD by conjugation to an oligonucleotide (e.g. PNA or PMO) capable of inducing exon skipping leading to production of normal dystrophin. Moreover, as PMODMD showed a uniformly higher activity in exon skipping assays to PNADMD, peptide-PMODMD conjugates are considered especially useful in the treatment of DMD.

The patient or subject to be treated may be any animal or human. The patient or subject may be a non-human mammal, but is more preferably a human patient. The patient or subject may be male or female.

Medicaments and pharmaceutical compositions according to aspects of the present invention may be formulated for administration by a number of routes, including but not limited to, parenteral, intravenous, intra-arterial, intramuscular, intratumoural, oral and nasal. The medicaments and compositions may be formulated in fluid or solid form. Fluid formulations may be formulated for administration by injection to a selected region of the human or animal body.

Administration is preferably in a "therapeutically effective amount", this being sufficient to show benefit to the individual. The actual amount administered, and rate and timecourse of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The peptides and peptide-cargo conjugates are also provided for use in in vitro methods. For example, the use of a peptide and/or peptide-cargo conjugate in a splice correction assay or serum stability assay is provided.

The term "in vitro" is intended to encompass experiments with cells in culture whereas the term "in vivo" is intended to encompass experiments with intact multi-cellular organisms.

A nucleic acid encoding a peptide according to the present invention is also provided. A nucleic acid vector, e.g. plasmid, having a regulatory sequence, e.g. promoter, operably linked to a nucleic acid encoding a peptide according to the present invention is also provided. The vector is preferably capable of expressing the peptide when transfected into a suitable cell, e.g. mammalian, bacterial or fungal cell. The nucleic acids may be provided in isolated or purified form.

In this specification the term "operably linked" may include the situation where a selected nucleotide sequence and regulatory nucleotide sequence are covalently linked in such a way as to place the expression of a nucleotide coding sequence under the influence or control of the regulatory sequence. Thus a regulatory sequence is operably linked to a selected nucleotide sequence if the regulatory sequence is capable of effecting transcription of a nucleotide coding sequence which forms part or all of the selected nucleotide sequence. Where appropriate, the resulting transcript may then be translated into a desired peptide.

In accordance with the above, the following aspects and embodiments of the present invention are provided.

In one aspect of the present invention a peptide is provided having an amino acid sequence comprised of at least three domains, having the arrangement:

N-terminus [Domain 1]-[Domain 2]-[Domain 3] C-terminus wherein
1. Domain 1 comprises at least 4 arginine residues and one or more X or B residues;
2. Domain 2 comprises the sequence ILFQ [SEQ ID NO:86], or ILIQ [SEQ ID NO:202];
3. Domain 3 comprises either a sequence having at least 3 arginine residues and one or more X or B residues, or comprises the sequence MKWHK [SEQ ID NO:203], or WKWHK [SEQ ID NO:204].

In Domains 1 and 3 the arginine residues are preferably spaced by one or two hydrophobic residues, e.g. one or two aminohexanoyl (X) or betaAlanine (B) residues in the sequence X, XX, B, BB, XB or BX, such that no more than two arginine residues are adjacent in the contiguous primary sequence of each of Domains 1 and 3.

In another aspect of the present invention there is provided a peptide, having a primary sequence structure comprised of at least three domains, having the arrangement:

N-terminus [Domain 1]-[Domain 2]-[Domain 3] C-terminus in which:

(i) Domain 1 comprises a sequence chosen from:

| | |
|---|---|
| RXRRBRRXR | [SEQ ID NO: 81] |
| RBRRXRRBR | [SEQ ID NO: 82] |

(ii) Domain 2 comprises a sequence chosen from:

| | |
|---|---|
| ILFQ, or | [SEQ ID NO: 86] |
| ILIQ | [SEQ ID NO: 202] |

(iii) Domain 3 comprises a sequence chosen from:

| | |
|---|---|
| RXRBRXR | [SEQ ID NO: 159] |
| RBRXRBR | [SEQ ID NO: 162] |
| RXRRXR | [SEQ ID NO: 161] |
| RXRXRXR | [SEQ ID NO: 160] |
| RXRBRX | [SEQ ID NO: 163] |

-continued

| | |
|---|---|
| MKWHK, or | [SEQ ID NO: 203] |
| WKWHK | [SEQ ID NO: 204] | wherein X=aminohexanoyl, B=betaAlanine

In some embodiments, Domain 2 comprises a sequence chosen from ILFQY [SEQ ID NO:88], or ILIQY [SEQ ID NO:296]. In some embodiments, Domain 2 comprises a sequence chosen from $Z_2Z_3ILFQZ_4$ [SEQ ID NO: 89], or $Z_2Z_3ILIQZ_4$ [SEQ ID NO: 297], wherein $Z_2$=I or no amino acid, $Z_3$=K, dK, H, R or no amino acid, $Z_4$=N or Y.

In some embodiments, Domain 3 comprises a sequence chosen from $Z_7Z_8$MKWHK [SEQ ID NO: 298], or $Z_7Z_8$WKWHK [SEQ ID NO: 299], where $Z_7$=R, dR, K or dK (wherein d=D-aminoacid) and $Z_8$=R, H or K. In some embodiments, Domain 3 comprises a sequence chosen from:

| | |
|---|---|
| dRRMKWHK | [SEQ ID NO: 111] |
| dRHMKWHK | [SEQ ID NO: 155] |
| dRRWKWHK | [SEQ ID NO: 157] |
| dKRMKWHK, or | [SEQ ID NO: 156] |
| dKHWKWHK | [SEQ ID NO: 158] |

In some embodiments, the peptide has a maximum length of 30 residues, including natural amino acids, X and B residues. 8. In some embodiments, Domain 1 has a length of from 6 to 11 residues, Domain 2 has a length of from 4 to 9 residues, and Domain 3 has a length of from 4 to 15 residues, wherein the lengths include natural amino acids, X and B residues.

In some embodiments, the peptide comprises, or consists of, a sequence chosen from one of SEQ ID NOs:242-277 (FIG. 25). In some embodiments, the peptide comprises, or consists of, a sequence having at least 90% sequence identity to one of SEQ ID NOs:242-277 (FIG. 25).

In some embodiments, the peptide comprises, or consists of, the sequence of Domains 1 to 3 or Domains 1 to 4 of one of Pip-5e, Pip-5j or Pip-5l (SEQ ID NOs:230, 234 or 236) or a sequence having at least 90% sequence identity to the sequence of Domains 1 to 3 or Domains 1 to 4 of one of Pip-5e, Pip-5j or Pip-5l (SEQ ID NOs:230, 234 or 236).

In some embodiments, the peptide comprises, or consists of, a sequence chosen from one of:

| | |
|---|---|
| $Z_1Z_2Z_3ILFQZ_4Z_5$RMKWHK | [SEQ ID NO: 113] |
| $Z_1Z_2Z_3ILFQZ_4Z_5$HMKWHK | [SEQ ID NO: 183] |
| $Z_1Z_2Z_3ILFQZ_4Z_5$RWKWHK | [SEQ ID NO: 184] |
| $Z_1Z_2Z_3ILFQZ_4Z_5$HWKWHK | [SEQ ID NO: 185] |
| $Z_1Z_2Z_3ILFQZ_4$RXRBRXR | [SEQ ID NO: 186] |
| $Z_1Z_2Z_3ILFQZ_4$RXRXRXR | [SEQ ID NO: 187] |
| $Z_1Z_2Z_3ILFQZ_4$RXRRXR | [SEQ ID NO: 188] |
| $Z_1Z_2Z_3ILFQZ_4$RBRXRBR | [SEQ ID NO: 189] |
| $Z_1Z_2Z_3ILFQZ_4$RXRBRXR | [SEQ ID NO: 190] |
| $Z_1Z_2Z_3ILFQZ_4$RXRBRX | [SEQ ID NO: 191] |
| $Z_1Z_2Z_3ILIQZ_4Z_5$RMKWHK | [SEQ ID NO: 192] |

```
Z₁Z₂Z₃ILIQZ₄Z₅HMKWHK      [SEQ ID NO: 193]

Z₁Z₂Z₃ILIQZ₄Z₅RWKWHK      [SEQ ID NO: 194]

Z₁Z₂Z₃ILIQZ₄Z₅HWKWHK      [SEQ ID NO: 195]

Z₁Z₂Z₃ILIQZ₄RXRBRXR       [SEQ ID NO: 196]

Z₁Z₂Z₃ILIQZ₄RXRXRXR       [SEQ ID NO: 197]

Z₁Z₂Z₃ILIQZ₄RXRRXR        [SEQ ID NO: 198]

Z₁Z₂Z₃ILIQZ₄RBRXRBR       [SEQ ID NO: 199]

Z₁Z₂Z₃ILIQZ₄RXRBRXR       [SEQ ID NO: 200]

Z₁Z₂Z₃ILIQZ₄RXRBRX        [SEQ ID NO: 201]
``` wherein:

$Z_1$=RRBRRXR [SEQ ID NO:81]; or RBRRXRRBR [SEQ ID NO:82];

$Z_2$=I or no amino acid $Z_3$=K, dK, H, R or no amino acid $Z_4$=N, Y $Z_5$=R or dR, K or dK wherein d=D-aminoacid.

In some embodiments, the peptide further comprises a linker sequence at the C-terminus. The linker sequence may be chosen from BCys, XCys, Cys, GGCys, BBCys, BXCys, XBCys, BX, or XB.

In some embodiments, the peptide is chemically conjugated to a cargo molecule. The conjugation may be at the C-terminus of the peptide.

The cargo molecule may be chosen from a nucleic acid, peptide nucleic acid (PNA), phosphorodiamidate morpholino oligonucleotide (PMO), locked nucleic acid (LNA), antisense oligonucleotide, short interfering RNA (siRNA), peptide, cyclic peptide, protein, or drug. The cargo molecule may have a molecular weight less than 5,000 Da. In some embodiments, the cargo molecule is PNADMD [SEQ ID NO:115] or PMODMD [SEQ ID NO:206] or a molecule having at least 90% sequence identity to one of PNADMD [SEQ ID NO:115] or PMODMD [SEQ ID NO:206].

In a further aspect of the present invention a pharmaceutical composition or medicament comprising a peptide according to the present invention is provided. The pharmaceutical composition or medicament may further comprise a pharmaceutically acceptable diluent, adjuvant or carrier.

In another aspect of the present invention a peptide according to the present invention is provided for use in a method of treatment of disease. In another aspect of the present invention the use of a peptide according to the present invention in the manufacture of a medicament for use in the treatment of a disease is provided.

In a further aspect of the present invention a method of treatment of a disease in a patient in need of treatment is provided, the method comprising administering a peptide according to the present invention to the patient.

Peptide Mimetics

The designing of mimetics to a known pharmaceutically or biologically active compound is a known approach to the development of pharmaceuticals and therapeutics based on a "lead" compound. This might be desirable where the active compound is difficult or expensive to synthesise or where it is unsuitable for a particular method of administration, e.g. some peptides may be unsuitable active agents for oral compositions as they tend to be quickly degraded by proteases in the alimentary canal. Mimetic design, synthesis and testing are generally used to avoid randomly screening large numbers of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

With regard to the present invention, a method is provided comprising the step of modifying the peptide structure, optionally followed by testing the modified peptide in a splice correction assay or an exon skipping assay and/or in a serum stability assay. This process of modification of the peptide or peptide mimetic may be repeated a number of times, as desired, until a peptide having the desired splice correction or exon skipping activity and/or serum stability is identified.

The modification steps employed may comprise truncating the peptide or peptide mimetic length (this may involve synthesising a peptide or peptide mimetic of shorter length), substitution of one or more amino acid residues or chemical groups, and/or chemically modifying the peptide or peptide mimetic to increase stability, resistance to degradation, transport across cell membranes and/or resistance to clearance from the body.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

Splice correction activity of CPP-PNA conjugates. Activity levels are presented as fold increase in the luminescence produced from HeLa pLuc705 cells incubated for 4 h in OptiMEM and 1 µM conjugate 1a-1e (A) or 2a-2g (B) (see Table 1—FIG. 3) compared with the luminescence produced from control HeLa pLuc705 cells incubated in OptiMEM in the absence of conjugate. Luciferase expression was quantified 20 h post-transfection as previously reported[19]. The data presented are averaged from at least three experiments and the error bars are indicated.

FIG. 2.

Splice correction activity of R6Pen-PNA conjugates, R6Pen-S—S—KPNA705k$_3$ (disulfide-linked) and R6Pen-S—C—KPNA705K$_3$ (stably linked) showing internalization by an energy-dependent mechanism as measured by the effect of ATP depletion (ATP) or low temperature (4° C.). Cells were pre-incubated in OptiMEM at 4° C. or 37° C. for 30 min (temperature dependence) or in OptiMEM supplemented with 10 mM NaN$_3$ and 6 mM 2-deoxy-D-glucose at 37° C. (ATP depletion), and further incubated for 1 h with 1 µM conjugate at 4° C. or 37° C. as appropriate. Cells were then washed and the incubation was continued for 23 h in DMEM complete medium and the luciferase assay carried out as in FIG. 1.

FIG. 3.

Table 1—Nomenclature, sequences (SEQ ID NOs:116-128) and MALDI-TOF mass spectral data of CPP-PNA conjugates.

FIG. 4.

Stability of (R-Ahx-R)$_4$C-ss-CK-PNA$_{705}$-K (m/z 6944.36) in 20% serum for 1 h by MALDI-TOF mass spectrometry, demonstrating that the conjugate was mostly stable under these conditions.

FIG. 5.

Stability of R6PenC-ss-CK-PNA$_{705}$-K (m/z 8524.14) in 20% serum for 1 h by MALDI-TOF mass spectrometry, demonstrating that the conjugate was completely cleaved under these conditions.

FIG. 6.

Stability of Pip1-ss-CK-PNA$_{705}$-K (m/z 8391.16) in 20% serum for 1 h by MALDI-TOF mass spectrometry, demonstrating that the conjugate was completely cleaved under these conditions.

FIG. 7.

Stability of Pip2b-ss-CK-PNA$_{705}$-K (m/z 8480.17) in 20% serum for 1 h by MALDI-TOF mass spectrometry, demonstrating that conjugate was mostly stable under these conditions.

FIG. 8.

Dose-dependent up-regulation of luciferase activity by peptide-PNA conjugates. HeLa pLuc705 cells were incubated for 4 h with increasing concentrations (0.3-0.4-0.6-0.8-1.2 µM) of Pip-2b-PNA705 (aka. Pip-2b-ss-CK-PNA$_{705}$-K, see FIG. 7) and Pip-3a-PNA705 conjugates. Luciferase expression was quantified 20 h later and normalized to untreated cells giving the values of folds increase in luminescence,

FIG. 9.

Dose-dependent splicing correction as judged by a RT-PCR assay. The upper band is the aberrant RNA transcript and the lower band is the splicing corrected RNA transcript. UT shows RNA from untreated HeLa cells.

FIG. 10.

Figure 9:
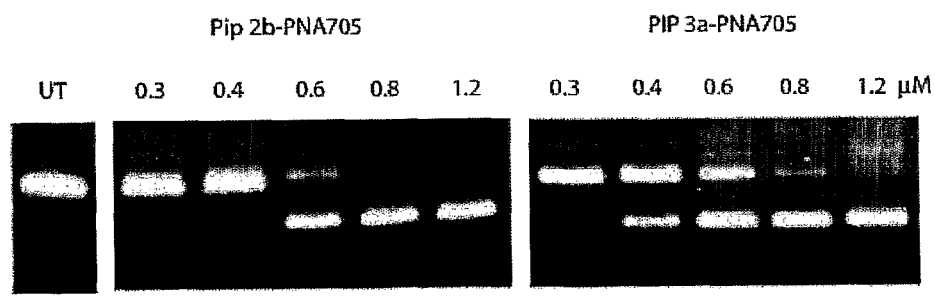

Graph showing how the EC$_{50}$ is determined by scanning of the gel in FIG. 9 (RT-PCR assay) for Peptide-PNA conjugates Pip-2b-PNA705 and Pip-3a-PNA705.

FIG. 11.

(A) Exon skipping seen in differentiated mouse mdx myoblasts treated with increasing concentrations of Pip-3a-PNADMD using a nested RT-PCR assay for dystrophin RNA. (B) Comparison of exon skipping activity in differentiated mouse mdx myoblasts treated with (R—X—R)$_4$-PNADMD, Pip-1-PNADMD, Pip-3a-PNADMD. All constructs have a stable thioether linkage.

FIG. 12.

Fold increases in luciferase production as judged by luminescence measurement with treatment of HeLa pLuc705 cells with 1 µM concentrations of CPP-PNA705 conjugates: Pip-2b-PNA705, (R-Ahx-R)$_4$-PNA705 and (R-Ahx-R)$_4$Ahx-βAla-PMO.

FIG. 13.

Graph showing number of dystrophin positive fibres per nmole following tibialis anterior injection of mdx mice with PNADMD and various CPP-PNADMD-constructs.

FIG. 14.

Luciferase expression (relative light units/µg protein) from splice correction assay in HeLa pLuc705 cells for R6Pen-PNA705, Pip-1-PNA705, Pip-2a-PNA705, Pip-2b-PNA705 and (R-Ahx-R)$_4$-PNA705 candidate CPP-PNAs at 37° C. and at 4° C.

FIG. 15.

Table showing peptide conjugates tested, including peptide sequences for Domains 1-4 and the PNA705 or PNADMD cargo. EC$_{50}$ is given for the conjugates in the HeLa cell luciferase splice correction assay. Stability for 1 h was assessed in the Serum Stability Assay.

FIG. 16.

Table showing Domain 1-3 peptide sequences according to the present invention.

FIG. 17.

Table showing exon skipping activity for a range of Pip peptides conjugated to PNADMD cargo in mouse mdx myotubes.

FIG. 18.

Table showing exon skipping activity for a range of Pip peptides conjugated to PMODMD cargo in mouse mdx myotubes.

FIG. 19.

Charts showing quantification of number of dystrophin-positive fibres for Pip-2b and (R-Ahx-R)$_4$ conjugated to PNADMD in tibialis anterior (TA), quadriceps, gastrocnemius (gas), biceps, diaphragm muscles (diaph), cardiac muscle (heart) and abdominal wall muscle (abdominal). This shows a higher number of dystrophin-positive fibres in heart and abdomen.

FIG. 20.

Diagram illustrating steps in PMO-peptide conjugation.

FIG. 21.

Exon skipping seen in differentiated mouse mdx myoblasts treated with 1 or 2 µM concentrations of B-peptide-PMODMD, Pip-5f-PMODMD and Pip-5f-PNADMD using a nested RT-PCR assay for dystrophin RNA.

FIG. 22.

Micrographs showing very strong dystrophin staining in tibialis anterior muscle following intramuscular injection in mdx mice with Pip-5e-PMODMD (upper) or Pip-5f-PMODMD (lower).

FIG. 23.

Chart showing mean percentage of dystrophin positive fibres following intramuscular injection into the tibialis anterior muscle of mdx mice with a range of Pip conjugates of PMODMD. Bars indicate standard error. B represents the 'B peptide' PMO conjugate control.

FIG. 24.

Western blots showing relative quantities of dystrophin produced by Pip-5e, Pip-5j, Pip-5l, Pip-5n and Pip-2b relative to B-peptide. Controls of wild type mouse (100% c57) and mdx mouse are also shown.

FIG. 25.

Table showing Domain 1-3 peptide sequences according to the present invention.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

The inventors have sought to design improved cell penetrating peptides. In particular they have sought a CPP that a) is stabilized to proteolysis and is thus suitable for in vivo use, b) has enhanced activity over R6Pen and (R-Ahx-R)$_4$ in a HeLa cell nuclear activity model when conjugated to a PNA sequence targeting the luciferase model intron and c) shows enhanced activity over naked PNA when conjugated to a PNA targeting exon 23 in the mouse mdx model.

In view of this, the inventors have designed a series of peptides, called PNA Internalizing Peptides (Pip) that differ in several key aspects from the previously disclosed R6Pen.

1) Their activities as PNA705 conjugates in the HeLa cell splicing correction model are higher (sub µM), 2) They have significant resistance to proteolysis (similar to (R-Ahx-R)$_4$C-KPNA705K), and 3) They have activity as PNADMD conjugates in a mouse mdx model by a) incubation with differentiated mouse myoblast cells and b) direct injection into the tibialis anterior muscle of mdx mice.

None of these attributes apply to R6Pen. The activities in vivo of Pip-2a and Pip-2b conjugates of PNA targeted to exon 23 are 2-3 fold higher compared to naked PNA, PNA conjugated to (R-Ahx-R)$_4$, or PNA conjugated to Pip1 (a non biostable peptide).

Pip2b-PNA appears to be energy-dependent in cell uptake and is likely to enter cells through the same or similar endosomal pathways as other cationic peptides, such as (R-Ahx-R)$_4$.

The activity of Pip-2b-PNA705 is several fold higher in the HeLa cell model than either (R-Ahx-R)$_4$-PNA705 or (R-Ahx-R)$_4$-PMO705.

Peptides

A range of candidate cell penetrating peptides were constructed and conjugated to a PNA Cargo.

For the luciferase assay the PNA cargo was PNA705 which has the 18-mer base sequence CCTCTTACCTCAGTTACA [SEQ ID NO: 114] and is linked to the peptide by disulphide bond.

For exon 23 skipping in mdx mice the PNA cargo was PNADMD which has the 20-mer base sequence GGCCAAACCTCGGCTTACCT [SEQ ID NO: 115] and is linked to the peptide by thioether linkage.

These core sequences may have additional N- and/or C-terminal sequences such as an N-terminal CK and C-terminal K or KKK to give, for example, the following cargo: CK-PNA705-K or CK-PNA705-K$_3$. The additional N-terminal sequence may enable disulphide or thioether linkage with Domain 4 of the peptide. The additional C-terminal sequence of amino acids may enhance water solubility of the conjugate.

Conjugation of PNA and CPP was either by disulphide bond formation or by thioether conjugation.

Splice Correction in HeLa pLuc705 Cells

A useful assay for assessing the activity of CPP-oligonucleotide conjugates has been established by Kole et al[10]. The assay involves the splice correction of an aberrant β-globin intron by an 18-mer synthetic oligonucleotide (at the 705 site) and subsequent up-regulation of firefly luciferase. The assay is uncomplicated and has a high dynamic range.

Conjugates were incubated for 4 h in 1 mL OptiMEM medium with exponentially growing HeLa pLuc705 cells (1.25×10$^5$ cells/well seeded and cultivated overnight in 24-well plates). The conjugates were then removed and incubation continued for 20 h in complete medium (DMEM/10% foetal bovine serum). Cells were washed twice with PBS and lysed with 300 µL of Reporter Lysis Buffer (Promega). Luciferase activity in 10 µL of cell lysates was quantified using the Luciferase Assay System substrate (Promega). Cellular protein concentrations were measured with the BCA™Protein Assay Kit (Pierce). AN experiments were performed in triplicate. Each data point was averaged over the three replicates.

Figure 1:
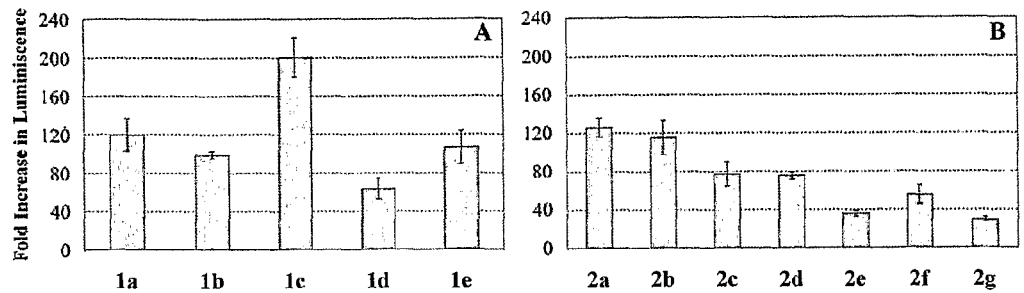
FIG. 1.

First are reported the splice correction activities of PNA705 conjugates of some variants of the R6Pen peptide and some composite peptides containing His, Phe and Arg residues (FIG. 1 and Table 1, FIG. 3).

A series of modified R6Pen peptides was synthesized and disulfide conjugated to KPNA705K$_3$, in the same way as previously described[19], and characterized by MALDI-TOF mass spectrometry (Table 1—FIG. 3). R6Pen-S—S—KPNA705K$_3$ (1a) showed a 120-fold increase over background in luminescence at 1 µM (FIG. 1A). Deletion of the double glycine spacer at the C-terminus of the peptide (Domain 4) (1b) had very little effect on activity (100-fold increase). By contrast, insertion of three Ahx spacers within the six N-terminal arginine residues (Domain 1) (1c) resulted in a significant increase in activity (to 200-fold). Replacement of the RRMKWKK basic region (Domain 3) plus GG spacer (Domain 4) by (R-Ahx)$_4$ (1e) maintained but did not increase the activity (110-fold), but replacement of the basic region alone by a Nuclear Localisation Signal (NLS) from SV40 (PKKKRKV) (1d) was somewhat detrimental (60-fold). A further variant where the basic domain and GG linker at the C-terminus of the peptide part (Domains 3 plus 4) is replaced by (R-Ahx)$_4$, (1e) maintained good activity in the HeLa pLuc705 splice correction assay. These results show that there is not an absolute sequence requirement within the two basic regions and that activity levels may be dependent on more subtle factors, such as cationic charge spacing and sections of hydrophobic sequence. The negative effect of the SV40 NLS sequence might be due to binding to the nuclear pore complex.

Another peptide that was reported to enhance activity of PMOs in the HeLa pLuc705 splice correction assay is R$_9$F$_2$[21]. However, it was found that the activity level for R$_9$F$_2$-PMO705 is modest compared to (R-Ahx-R)$_4$-PMO705[16]. Addition of histidine residues in amphipathic peptides has been shown to promote DNA delivery into cells[22]. We synthesized a series of peptides containing the R$_9$F$_2$ motif surrounded on each side with blocks of His, Phe or Ahx residues and disulfide conjugate them to PNA705 (Table 1—FIG. 3). In this case only one additional Lys residue was present on each end of the PNA. Interestingly, compared to R6Pen-S—S—KPNA705K (2a), H$_2$F$_2$R$_9$F$_2$-S—S—KPNA705K (2b) was found to have similarly good activity in the splice correction assay at 1 µM concentration (120-fold, FIG. 1B). By contrast, all of the other peptide-PNA conjugates synthesized (2c-2g) that contained larger numbers of His residues and/or Ahx spacers showed lower activity levels (25-75-fold increase). The $H_2F_2R_9F_2$ motif is thus a reasonable CPP and disulfide-linked conjugates with KPNA705K show significantly higher activity than (R-Ahx-R)$_4$—S—S—KPNA705K, for example (ca. 10-fold increase at 1 µM, data not shown). However, such motifs do not show high enough activity and are not likely to be sufficiently stable for in vivo use since there are many adjacent R residues. This work teaches that some peptides that have reasonable activity in the HeLa cell splice correction assay are less preferred as candidates for possible therapeutic use.

Figure 2:
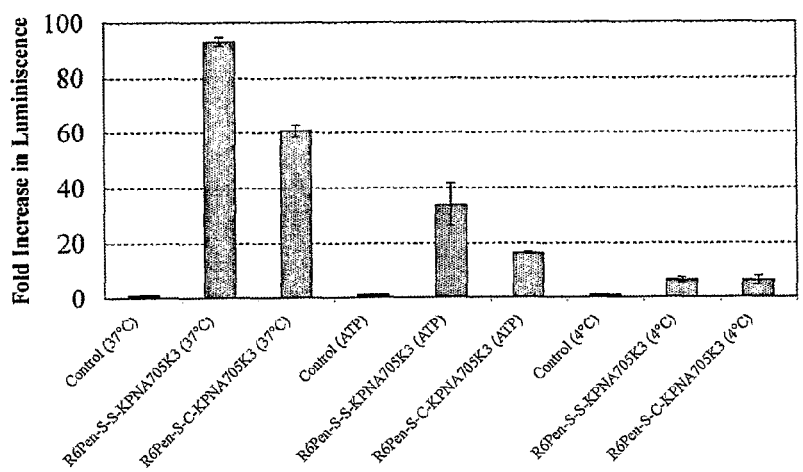

It has been previously reported that (R-Ahx-R)$_4$-PMO is internalized by HeLa cells in an energy-dependent mechanism, since activity in the splice correction assay was abolished at 4° C.[16]. When we carried out the splice correction assay at 4° C. for disulfide-linked R6Pen-S—S—KPNA705K$_3$ or stably linked R6Pen-S—C—KPNA705K$_3$[19], in both cases there was a dramatic loss of activity compared to activities at 37° C. (FIG. 2). A substantial decrease in activity was also seen when cells were depleted of ATP. A similar loss of activity at low temperature was seen for $H_2F_2R_9F_2$—S—S—KPNA705k (data not shown). These data point to cell internalization of these conjugates through an energy-dependent endocytotic pathway, although the precise nature of the pathway has not been determined in each case as yet.

A new series of peptides (PNA Internalization Peptides, Pip) was therefore designed.

Figure 8:
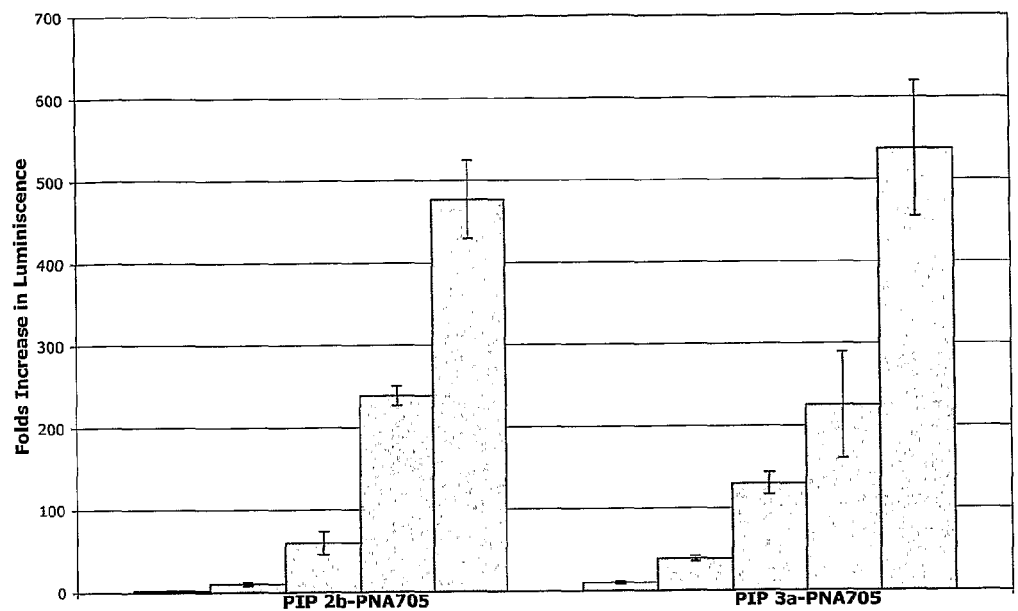

FIG. 8 shows a dose-dependent up-regulation of luciferase activity by Pip-2b and Pip-3a PNA705 conjugates. Activity is shown as fold increase in luminescence compared to untreated cells.

Figure 12:
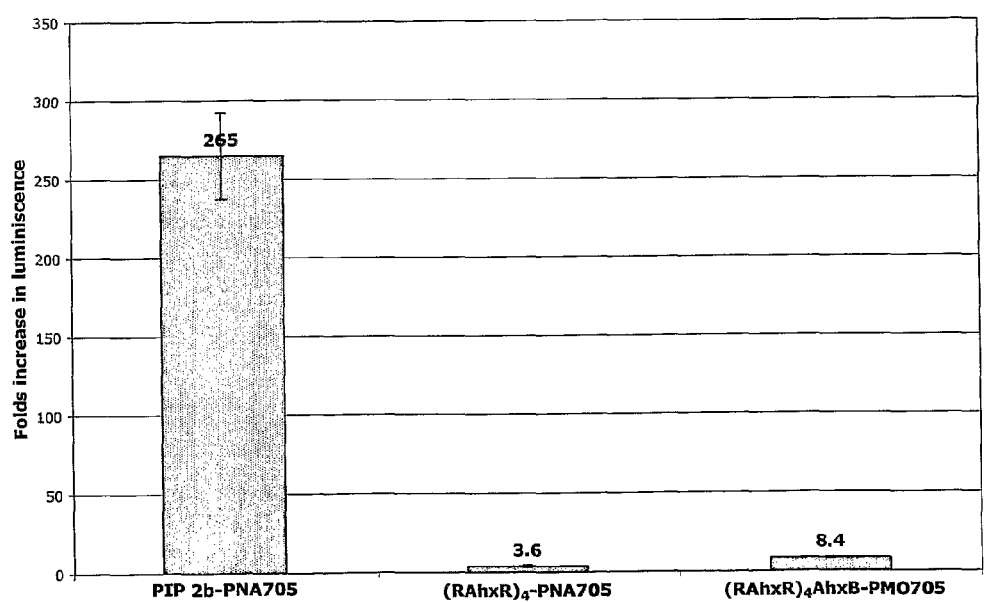

FIG. 12 shows high levels of activity of the Pip-2b-PNA705 conjugate in the firefly luciferase up-regulation assay as compared to the (R-Ahx-R)$_4$-PNA705 and (R-Ahx-R)$_4$AhxB-PMO705 conjugates. Activity is shown as fold increase in luminescence compared to untreated cells.

Figure 14:
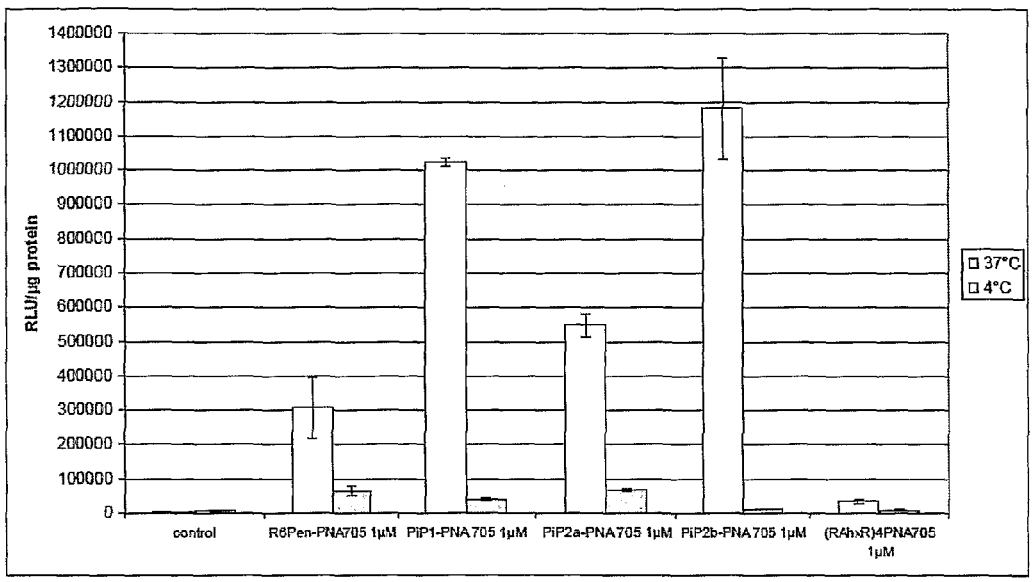

The results shown in FIG. 14 were obtained using a HeLa cell splice correction assay conducted according to the following protocol.

Exponentially growing HeLa pLuc705 cells (1.75×10$^5$ cells/well seeded and cultivated overnight in 24 well plates) were pre-incubated for 30 min in OptiMEM at 37° C. or 4° C.

The cells were then incubated in the presence of 1 µM of the various peptide-PNA conjugates at 37° C. (white bars) or at 4° C. (grey bars) for 1 h. Luciferase expression was quantified 23 h later and expressed as RLU/µg protein. Each experiment was made in triplicate and error bars (standard deviations) are indicated.

Results are shown in FIG. 14. Pip-1, Pip-2a and Pip-2b PNA705 conjugates showed considerably higher luciferase up-regulation compared to control R6Pen and (R-Ahx-R)$_4$PNA705 at 37° C. However at 4° C. all of the CPP-PNA conjugates lose most of their activities. This shows that all of these peptide-PNAs are internalized by an energy-dependent pathway, which is consistent with endocytosis. However the Pip series of peptides show far higher activity levels in this assay when conjugated to PNA705 compared to R6Pen and this in turn has far higher activity than (R-Ahx-R)$_4$PNA705.

RT-PCR Analysis of Splice Correction

RT-PCR can also be used to assess splice correction in the HeLa pLuc705 luciferase splice correction assay of Kole et al.

To perform RT-PCR analysis of splice correction, total RNA was extracted from 300 µL of combined cell lysates (3×100 µL) from triplicate wells corresponding to each conjugate concentration using 1 mL of TRI Reagent (Ambion).

Figure 10:
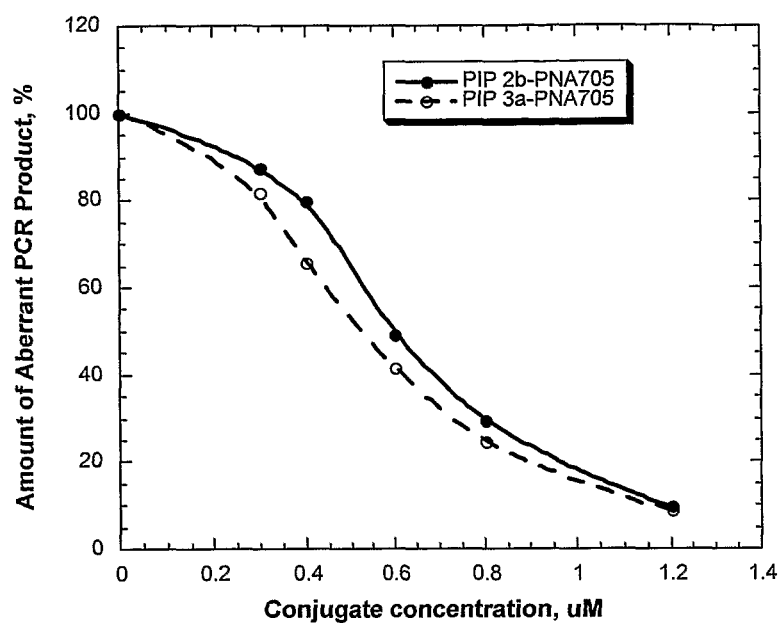

The RT-PCR was carried out in 25 µL with 0.5 µg RNA template using SuperScript III One-Step RT-PCR System with Platinum Taq DNA polymerase (Invitrogen) primed by forward primer 5'TTG ATA TGT GGA TTT CGA GTC GTC3' [SEQ ID NO: 133] and reverse primer 5'TGT CAA TCA GAG TGC TTT TGG CG3' [SEQ ID NO: 134]. The initial cDNA synthesis was performed at 55° C. for 30 min followed by 30 cycles of 95° C. for 30 sec, 58° C. for 1 min and 68° C. for 1 min. The products were analysed on a 2% agarose gel (FIG. 9) and after scanning using Gene Tools Analysis Software (SynGene) $EC_{50}$ values were calculated from graphical distribution of aberrant PCR product (FIG. 10).

FIG. 9 shows dose-dependent splice correction in the HeLa pLuc705 luciferase assay as determined by RT-PCR for Pip-2b-PNA705 and Pip-3a-PNA705. $EC_{50}$ measurement is shown in FIG. 10.

These results are consistent with the luciferase up-regulation assay results shown in FIG. 8.

$EC_{50}$ values for splice correction are shown in FIG. 15 for Pip-2a to Pip-5c conjugates with PNA705. Pip-2a, Pip-2b, Pip-2c, Pip-3a, Pip-4b, Pip-4c, Pip-5a, Pip-5b and Pip-5c conjugates all showed $EC_{50}$ values less than 0.8 µM, whereas Pip-3b-PNA705 was slightly worse and Pip-4a-PNA705 and Pip-4d-PNA705 considerably worse. These results further demonstrate that domain 2 has sequence specificity. The best sequences contain either ILFQN or ILFQY in domain 2.

Serum Stability Assay

CPP-PNA conjugates (20 µM) were incubated in PBS containing 20% mouse serum* at 37° C. Aliquots of 10 µL were taken at 0, 15, 30, 60 and 120 min, and diluted with 50 µL 10% DCA in $H_2O/CH_3CN$ (50/50). The samples were mixed and kept at −20° C. The precipitated serum proteins were separated by centrifugation (13000 rpm, 5 min) and the supernatant was analysed by MALDI-TOF mass spectrometry.

*Mouse serum was prepared by centrifugation (3×30 min, 13000 rpm, 4° C.) of fresh clotted blood from female Balb/c mice.

Figure 4:
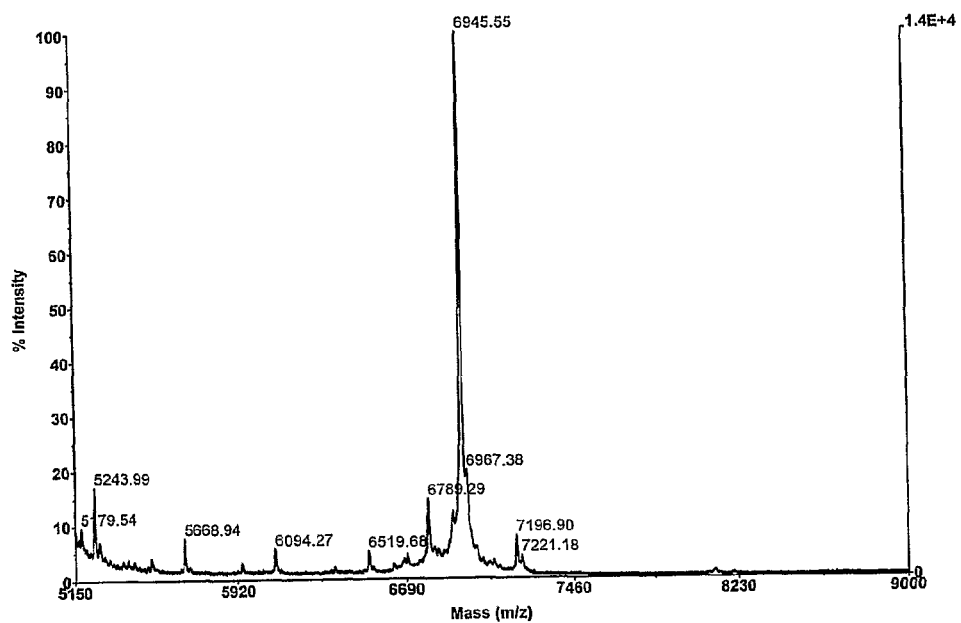

The stability of (R-Ahx-R)$_4$C-ss-CK-PNA$_{705}$-K (m/z 6944.36) in 20% serum for 1 h by MALDI-TOF mass spectrometry is indicated in FIG. 4 which shows that under these conditions there is only minor serum proteolysis of (R-Ahx-R)$_4$C-ss-CK-PNA$_{705}$-K.

Figure 5:
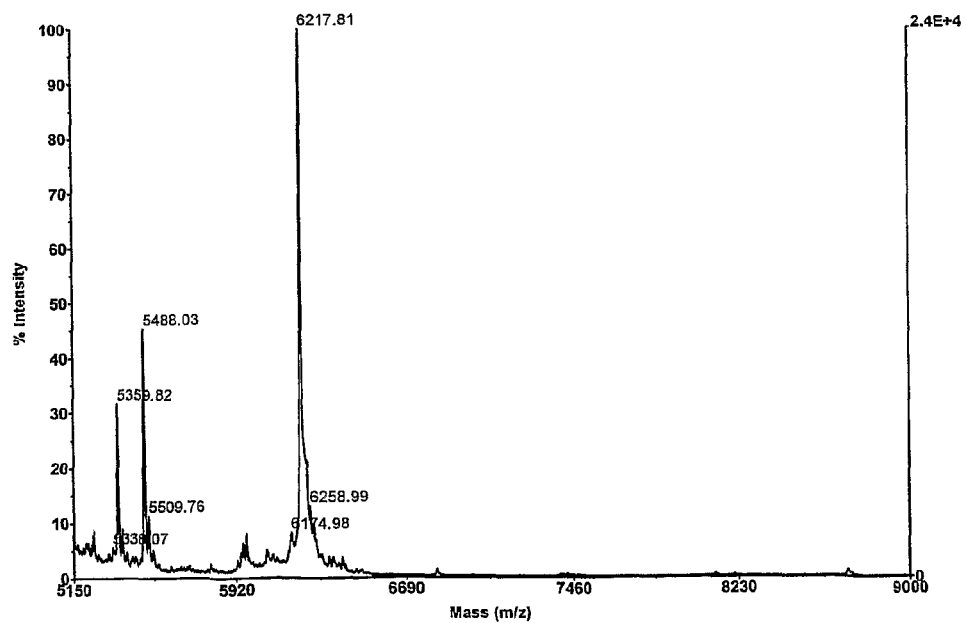

The stability of R6PenC-ss-CK-PNA$_{705}$-K (m/z 8524.14) in 20% serum for 1 h by MALDI-TOF mass spectrometry is indicated in FIG. 5. This shows that R6Pen is completely cleaved in at least one internal position within the peptide within 1 hour to give a major and several minor products. Further degradation of the peptide occurs after 1 hour. The PNA cargo component is stable.

Figure 6:
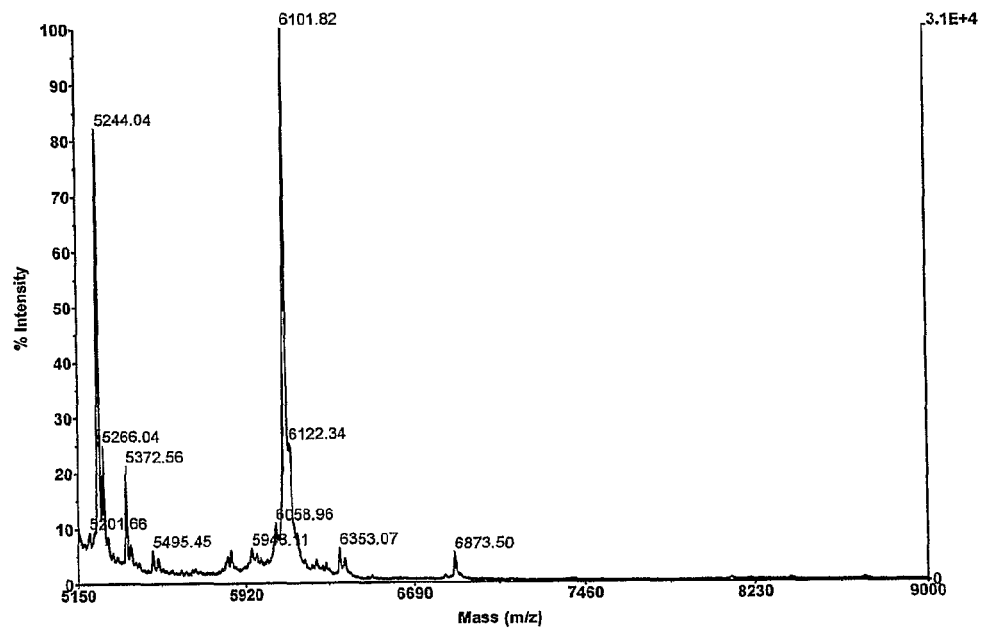

The stability of Pip1-ss-CK-PNA$_{705}$-K (m/z 8391.16) in 20% serum for 1 h by MALDI-TOF mass spectrometry is indicated in FIG. 6. This shows that the Pip1 peptide has not gained sufficient stability compared to R6Pen and there is still complete cleavage after 1 hour.

Figure 7:
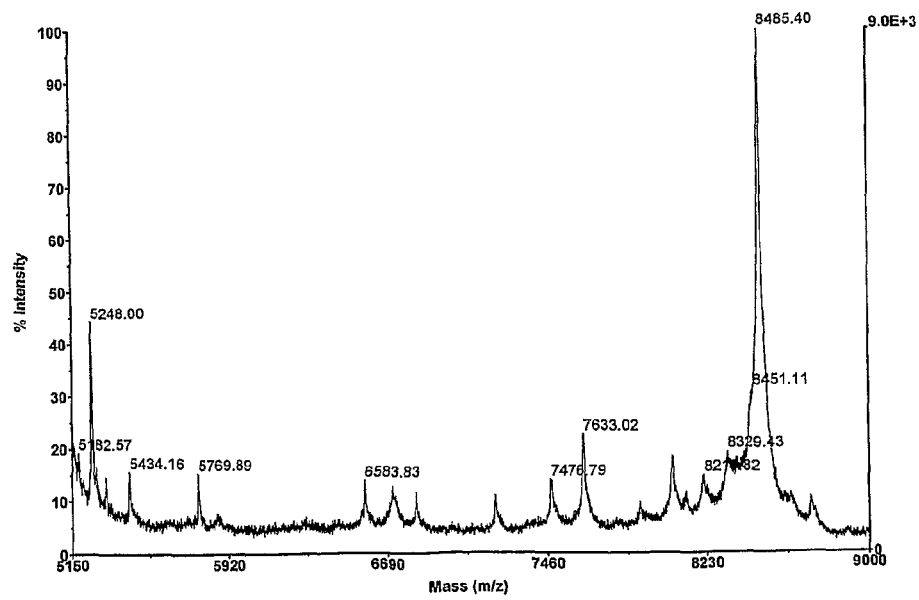

The stability of Pip2b-ss-CK-PNA$_{705}$-K (m/z 8480.17) in 20% serum for 1 h by MALDI-TOF mass spectrometry is indicated by FIG. 7. This shows that Pip2b is predominantly unaltered after 1 hour and there are only minor cleavage products. The stability is therefore similar under these conditions to (R-Ahx-R)$_4$-PNA.

These results show that Pip2b-PNA has sufficient stability to serum proteolysis to be a candidate for in vivo studies. Similar stability to serum proteolysis was also seen for Pip-2a-PNA, Pip-3a-PNA and Pip-3b-PNA as judged by MALDI-TOF mass spectrometry (data not shown).

Exon Skipping in Differentiated H2K mdx Cells

Yin and Wood achieved some skipping of exon 23 in cultured mouse mdx myoblasts in the presence of a transfection agent using PNA and PNA conjugates[23]. The same approach can be taken to assess the effect of peptides according to the invention on cellular penetration of peptide-PNA conjugates. In this case the incubation of peptide-PNA conjugates is in the absence of a transfection agent.

A PNA 20-mer to be used in exon 23 skipping experiments in the DMD mdx model is:

```
GGCCAAACCTCGGCTTACCT.    [SEQ ID NO: 115] (PNADMD)
```

Myotubes were obtained from confluent H2K mdx cells seeded in gelatin coated 24-well plates following 2 days of serum deprivation (DMEM with 5% Horse serum). The CPP-PNA conjugates were incubated with myotubes for 4 h in 0.5 mL OptiMEM and then replaced by 1 mL of DMEM/5% Horse serum media for further incubation. After 20 h myotubes were washed twice with PBS and total RNA was extracted with 0.5 mL of TRI Reagent. RNA preparations were treated with RNAse free DNAse (2 U) and Proteinase K (20 μg) prior to RT-PCR analysis. The RT-PCR was carried out in 25 μL with 1 μg RNA template using SuperScript III One-Step RT-PCR System with Platinum Taq DNA polymerase (Invitrogen) primed by forward primer 5'CAG AAT TCT GCC AAT TGC TGAG3' [SEQ ID NO: 129] and reverse primer 5'TTC TTC AGC TTG TGT CAT CC3' [SEQ ID NO: 130]. The initial cDNA synthesis was performed at 55° C. for 30 min followed by 30 cycles of 95° C. for 30 sec, 55° C. for 1 min and 68° C. for 80 sec. RT PCR product (1 μL) was then used as the template for secondary PCR performed in 25 μL with 0.5 U Super TAQ polymerase (HT Biotechnologies) and primed by forward primer 5'CCC AGT CIA CCA CCC TAT CAG AGC3' [SEQ ID NO:131] and reverse primer 5'CCT GCC TTT AAG GCT TCC TT3' [SEQ ID NO: 132]. The cycling conditions were 95° C. for 1 min, 57° C. for 1 min and 72° C. for 80 sec for 25 cycles. Products were examined by 2% agarose gel electrophoresis and, after scanning, using Gene Tools Analysis Software (SynGene). The relative amount of exon 22 skipping was expressed as a percentage at a given concentration of conjugates averaged over duplicates of three experiments.

Figure 11A:
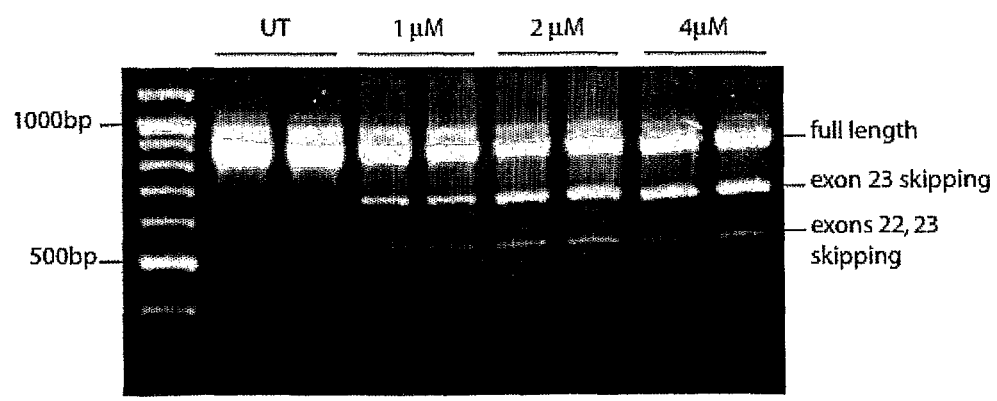
Figure 11B:
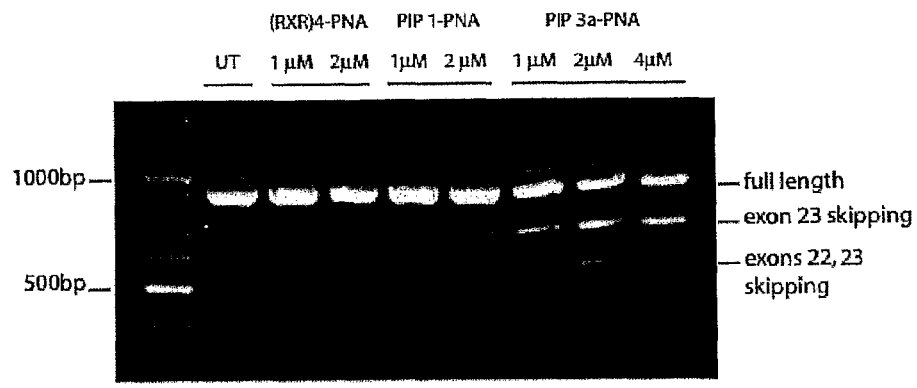

FIG. 11A shows an increase in exon 23 skipping and exon 22, 23 double skipping in differentiated mouse mdx myoblasts as determined by RT-PCR with increasing dose of Pip3a-PNADMD. FIG. 11B shows exon 23 skipping in differentiated mouse mdx myoblasts as determined by RT-PCR for Pip3a-PNADMD. No activity for (R-Ahx-R)$_4$-PNADMD was found at equivalent conjugate concentrations and very weak exon 23 skipping (but not exon 22, 23 double skipping) was found for Pip-1-PNADMD.

These results show that Pip-3a-PNADMD has good activity in this model. A similar result is expected for Pip-2a-PNADMD and Pip-2b-PNADMD.

Exon skipping levels (% of exon 23 deletion compared to unskipped) were determined at 1 μm and at 2 μM added conjugate by scanning of the agarose gel, and results are shown in FIG. 17. Pip-2a, Pip-2b, Pip-4-b, Pip-4-c, Pip-4-e, Pip-4-f, Pip-4-g and Pip-4-h as thioether conjugates of PNADMD all showed exon skipping at >30% at 2 μM and 16-27% at 1 μM. Pip-3a and Pip-3b conjugates with altered domain 2 were slightly less active. Once again all the best peptides contained the sequence ILFQN or ILFQY in domain 2. Domain 1 contained 5 or 6 spaced Arg residues and the results showed that some aminohexanoyl (X) spacers could be replaced by either Beta-Ala (B) or by Ile (I).

A further series of Pip peptides was synthesized (Pip-5a to Pip-5g) as conjugates of PNADMD. Pip-5a to Pip-5g all had domain 1 of RXRRBRRXR [SEQ ID NO:81] and domain 2 of ILFQY [SEQ ID NO:88] or ILIQY [SEQ ID NO:296] (Pip-5g). Pip-5a to Pip-5d and Pip-5g each had slight variations in the sequence of domain 3 but maintained two basic residues in the first two positions, M or W in the third position followed in each case by KWHK. In the cases of Pip-5e and Pip-5f domain 3 was significantly altered to give 4 Arg residues spaced by either X or B residues. Pip-5a, Pip-5b, Pip-5e, Pip-5f and Pip-5g PNADMD conjugates all showed good exon skipping of ≥30% at 2 μM. Pip-5c and Pip-5d conjugates were slightly poorer. These results showed that domain 3 can consist of spaced Arg residues and that domain 2 can be ILFQY or ILIQY.

Pip-5h contains shorter domains 1 and 3 with only 4 spaced Arg residues in each case (RXRRRXR [SEQ ID NO:74]) whilst maintaining an optimal domain 2 (ILFQY [SEQ ID NO:88]). Pip-5h-PNADMD showed lower activities for % exon skipping at both 1 and 2 μm respectively compared to for example Pip-5e-PNADMD. This result shows that 4 Arg residues in domain 1 are insufficient for optimal exon skipping activity in mdx muscle cells.

For synthetic simplicity therefore (least number of different amino acids and including no Lys or His residues or D-amino acids) Pip-5e and Pip-5f are optimal sequences.

Exon Skipping and Restoration of Dystrophin Expression by PNA in mdx Mouse

Yin and Wood achieved efficient skipping of exon 23 in mdx mice by single intramuscular injections of PNA and PNA-conjugates into the tibialis anterior muscles of mdx mice[23]. The same approach was taken to assess the effect of Pip-PNADMD conjugates.

The PNA 20-mer GGCCAAACCTCGGCTTACCT [SEQ ID NO: 115] (PNADMD) was used in exon 23 skipping experiments in the DMD mdx model.

Exon skipping can be assessed according to the protocol of Yin and Wood[23], which may be summarised as follows.

8-week old male mdx mice (number is 3) are given 5 μg PNA or CPP-PNA conjugates in saline and water; total volume is 40 μl intramuscular injection into the tibilias anterior muscle. The tissues are harvested 3 weeks after injection.

Tissues are assayed by immunohistochemistry using a rabbit polyclonal antibody (targeted at C terminal of dystrophin protein) and nuclei counter-stained with DAPI. Dystrophin-positive fibres are counted by fluorescence microscopy using Alex vision LE software.

Figure 13:
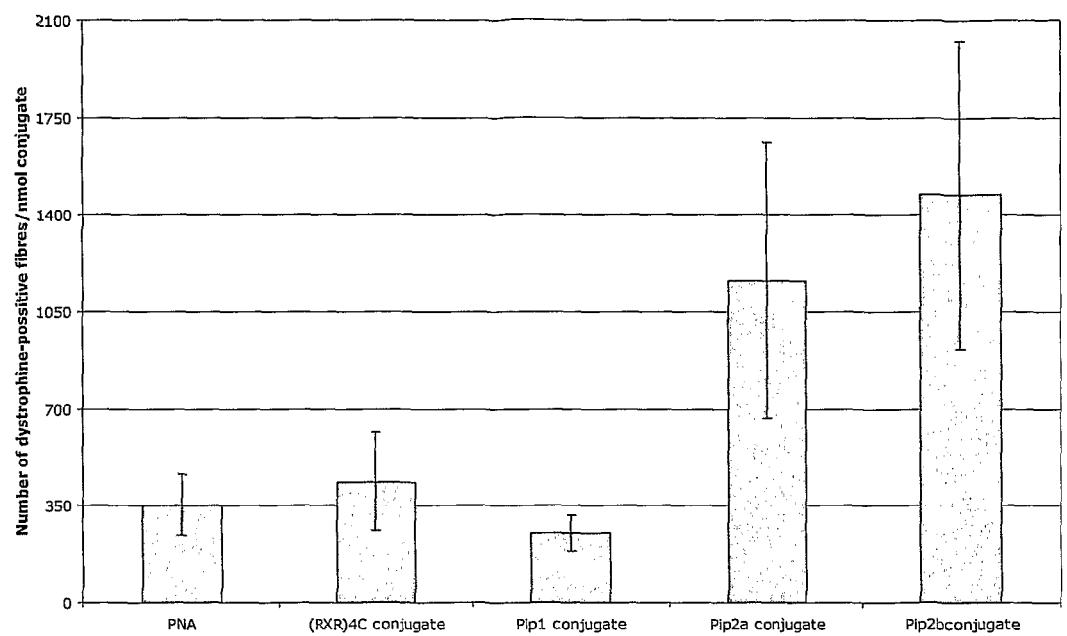

Initial results are shown in FIG. 13. Pip2a and Pip2b conjugates with PNA [SEQ ID NO: 32 and 33] show considerably better exon skipping activity in mdx mouse than Pip-1-PNADMD, (R-Ahx-R)$_4$-PNADMD or naked PNADMD.

It should be noted that (R-Ahx-R)$_4$-PMO conjugate has shown significant activity in a number of muscle types in mdx mice following intraperitoneal administration[24]. Therefore it is reasonable to suppose that Pip-2a and Pip-2b conjugates to PNADMD, and subsequent Pip-3 and Pip-4 conjugates, are likely to show significant activity by routes of delivery other than by direct muscle injection, such as intraperitoneal or intravenous and such experiments are therefore in progress.

mdx mice were injected with a 80 μl dose of PNA-peptide conjugate (Pip-2b-PNADMD or (RXR)4-PNADMD) with saline at a final dose of 25 mg/kg. The mice were killed at 2 weeks after injection by $CO_2$ inhalation and tissues were removed and snap-frozen in liquid nitrogen-cooled isopentane and stored at −80° C.

Immunohistochemistry and Dystrophin-Positive Fibre Counting:

Sections of 8 µm were cut from at least two-thirds of the muscle length of tibialis anterior (TA), quadriceps, gastrocnemius, biceps, abdominal wall and diaphragm muscles and cardiac muscle at 100 µm intervals. The sections were then examined for dystrophin expression with a polyclonal antibody 2166 against the dystrophin carboxyl-terminal region (the antibody was kindly provided by Professor Kay Davies). The maximum number of dystrophin-positive fibres in one section was counted using the Zeiss AxioVision fluorescence microscope. The intervening muscle sections were collected either for RT-PCR analysis and Western blot or as serial sections for immunohistochemistry. Polyclonal antibodies were detected by goat-anti-rabbit IgGs Alexa Fluro 594 (Molecular Probe, UK).

Protein Extraction and Western Blot

The collected sections were placed in a 1.5 ml polypropylene eppendorf tube (Anachem, UK) on dry ice. The tissue sections were lysed with 150 µl protein extraction buffer containing 125 mmol/l Tris-HCl (pH=6.8), 10% sodium dodecyl sulphate, 2 mol/l urea, 20% glycerol, and 5% 2-mercaptoethanol. The mixture was boiled for 5 minutes and centrifuged. The supernatant was collected and the protein concentration was quantified by Bradford assay (Sigma, UK). Various amounts of protein from normal C57BL6 mice as a positive control and corresponding amounts of protein from muscles of treated or untreated mdx mice were loaded onto sodium dodecyl sulphate polyacrylamide gel electrophoresis gels (4% stacking, 6% resolving). Samples were electrophoresed for 4 hours at 80 mA and transferred to nitrocellulose overnight at 50 V at 4° C. The membrane was then washed and blocked with 5% skimmed milk and probed overnight with DYS1 (monoclonal antibody against dystrophin R8 repeat, 1:200, NovoCastra, UK) for the detection of dytstrophin protein and β-actinin (monoclonal antibody, 1:5000, Sigma, UK) as a loading control. The bound primary antibody was detected by horseradish peroxidise-conjugated rabbit anti-mouse IgGs and the ECL Western Blotting Analysis system (Amersham Pharmacia Biosciences, UK). The intensity of the bands obtained from treated mdx muscles was measured by Image J software; the quantification is based on band intensity and area, and is compared with that from normal muscles of C57BL6 mice.

The results showed (FIG. 19) that both conjugates induced a similar increase in the number of centrally nucleated muscle fibres in TA, quadriceps, gastrocnemius, biceps and diaphragm, but that Pip-2b-PNADMD had a significantly higher fibre count in heart and abdomen.

Synthesis of Pip Conjugates of Alternative Cargo PMO Oligonucleotide

PMO 25-mer M23D(+7-18) (5'-GGCCAAACCTCGGCT-TACCTGAAAT-3' [SEQ ID NO:206]) (PMODMD) is commonly used as an oligonucleotide analogue suitable for exon skipping in mdx mice[37,42,43,44]. In many of these examples, B peptide (sequence RXRRBRRXRRBRXB [SEQ ID NO:207]) was conjugated to PMODMD and shown to significantly enhance exon skipping and dystrophin production by intramuscular or intravenous delivery in mdx mice compared to naked PMODMD. The B-peptide (which differs from $(RXR)_4XB$ only by two replacements of X by B units) is now the leading candidate peptide for clinical trial development in conjugation with a PMO for DMD treatment[43].

Figure 20:
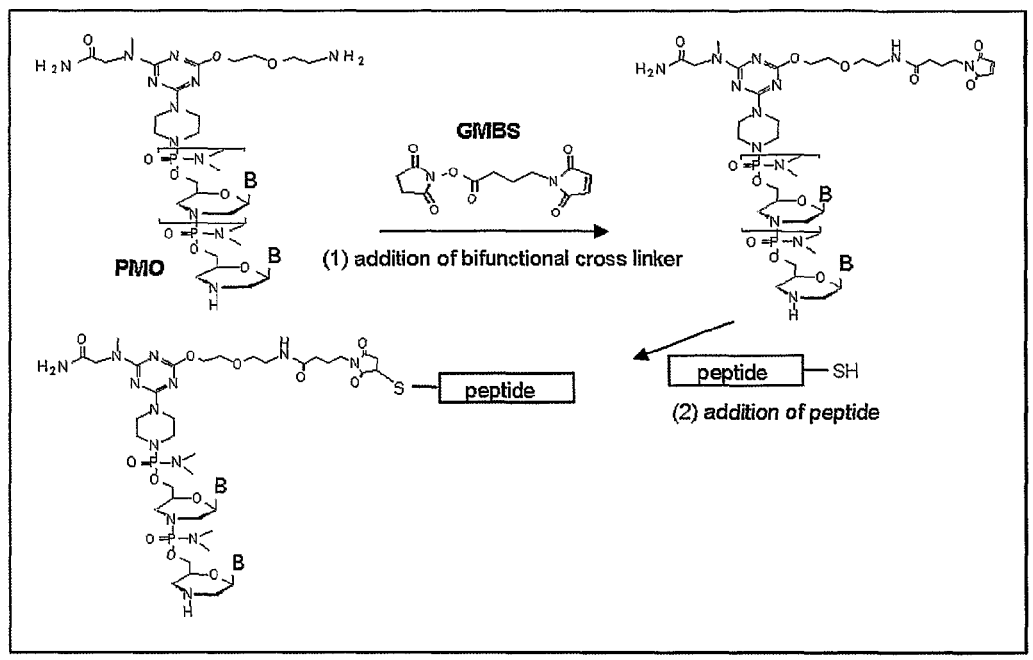

We developed a procedure for the preparation of peptide conjugates of PMO oligonucleotides via a thioether (thiomaleimide) linkage based on the method described by Moulton et al[45]. This method involves the use of N-[γ-maleimidobutyryloxy]succinimide ester (GMBS), a heterobifunctional cross-linker containing an amine-reactive N-hydroxysuccinimide (NHS) ester at one end and a sulfhydryl-reactive maleimide group at the other end. First, the 5'-primary amine of 5'-amino-linked 25-mer PMODMD (Gene Tools Inc) was activated by reaction with GMBS (FIG. 20). The PMO-linker intermediate was subsequently attached to the peptide through a thiomaleimide linkage. Purification was however was much simpler than that described by Moulton et al[45] in the use of a single HPLC separation involving use of a heptafluorobutyric acid (HFBA) buffer.

Thus, 1000 nmole of PMODMD was dissolved in 100 µl 50 mM sodium phosphate buffer (pH 7.2) containing 20% acetonitrile (makes 10 mM stock). A 100 mM GMBS stock solution was prepared in DMSO. To 10 µl of a 10 mM solution of PMODMD in a 1.5-ml microfuge tube was added 13 µl of 50 mM sodium phosphate buffer (pH 7.2) containing 20% acetonitrile. 2 µl of GMBS solution (2-fold molar excess) was added, the mixture vortexed and incubated for 1 h at room temperature in the dark. 750 µl of cold acetone (30-fold excess) was added to precipitate the product, which was collected by centrifugation for 2 min at 13,000 rpm at room temperature. The acetone was removed by decantation and the residue dried in air for 30 minutes. The PMO-linker product was dissolved in 30 µl of 50 mM sodium phosphate buffer (pH 6.5) containing 20% acetonitrile (to make a 2 mM solution, assuming 100% recovery). 20 µl of 10 mM peptide thiol (2-fold molar excess) was added, the tube vortexed and incubated at room temperature for 2 h in the dark. The reaction mixture may be stored overnight at 4° C. if necessary. The product was then purified by RP-HPLC on a Jupiter C18 column (250×10 mm) with buffer A, 0.1% HFBA in water, and buffer B, 90% acetonitrile in 0.1% HFBA (gradient: 38%-50% B in 20 minutes) with detection at 260 nm. The product was collected, lyophilized, and dissolved in sterile water. The product was analysed by MALDI-TOF mass spectrometry on a Voyager DE Pro using a matrix of 2,6-dihydroxyacetophenone (20 mg/ml) in methanol/diammonium hydrogen citrate.

Pip-5e to Pip-5o, Pip-2b and control B peptide were synthesized as conjugates of PMODMD (FIG. 18).

Exon Skipping in Differentiated H2K mdx Cells (PMO Coniugates)

Exon skipping levels (% of exon 23 deletion compared to unskipped) were determined at 0.5 µM, 1 µm and at 2 µM added conjugate to differentiated H2K mdx mouse cells and agarose gels scanned by the method described for Pip-PNA.

Figure 21:
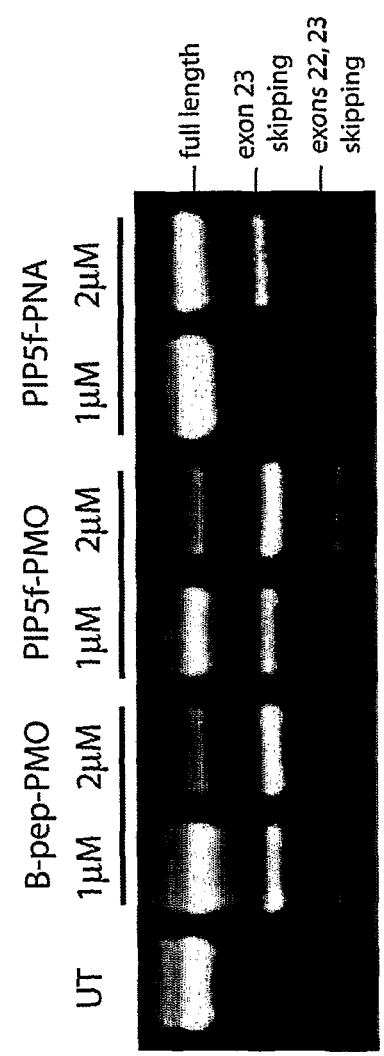

The first observation is that the levels of exon 23 skipping for PMO conjugates are at least twice those for PNA conjugates having the same Pip peptide attached (e.g. Pip-5f-PMODMD compared to Pip-5f-PNADMD, FIG. 21). Particularly active conjugates taking into consideration results at all 3 concentration levels were Pip-5e-1.0 PMODMD and Pip-5j-PMODMD but all conjugates except Pip-5m-PMODMD had very high exon skipping activity at 2 µM concentration. B-peptide-PMODMD was slightly less active than the leading Pip-5e-PMODMD and Pip5j-PMODMD conjugates. Exon skipping levels are shown in FIG. 18.

Exon Skipping and Restoration of Dystrophin Expression by PMO-Conjugates in mdx Mouse The in vivo activities of Pip-PMO conjugates were determined by intramuscular injection. 5 µg of PMO-peptide conjugate in saline (40 µl) was injected into the tibialis anterior muscle of mdx mice and tissue harvested at 2 weeks after injection as described above.

Figure 22:
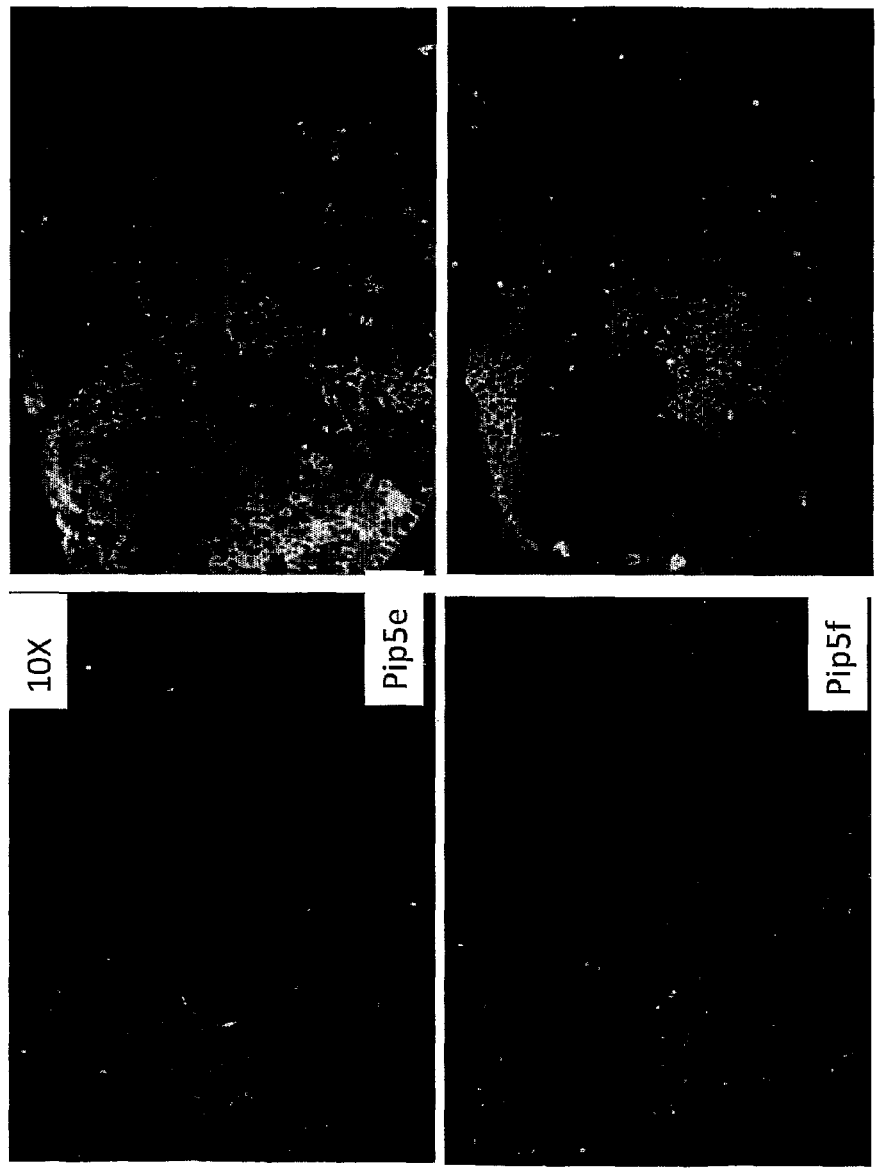
Figure 23:
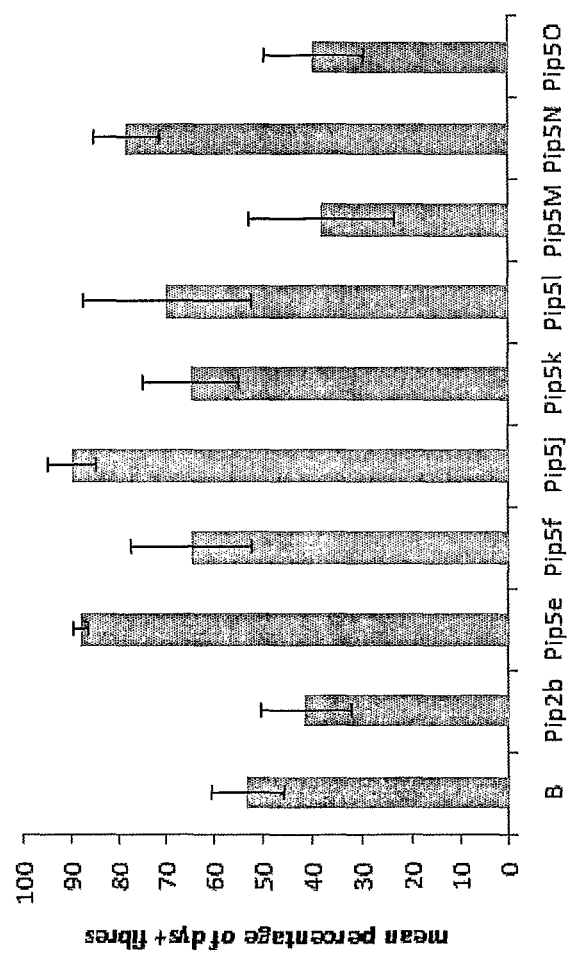

All of the PMODMD conjugates tested (Pip-2b, Pip-5e, Pip-5f, Pip-5j, Pip-5k, Pip-5l, Pip-5m, Pip-5n and Pip-5o, as well as B-peptide control) showed significant staining for dystrophin positive fibres (for example, Pip-5e and Pip-5f, FIG. 22). Calculation of the mean percentage of dystrophin positive fibres showed that some of the Pip conjugates had significantly higher values than B-peptide conjugate, notably Pip-5e and Pip-5j as well as Pip-5l and Pip-5n (FIG. 23).

Figure 24:
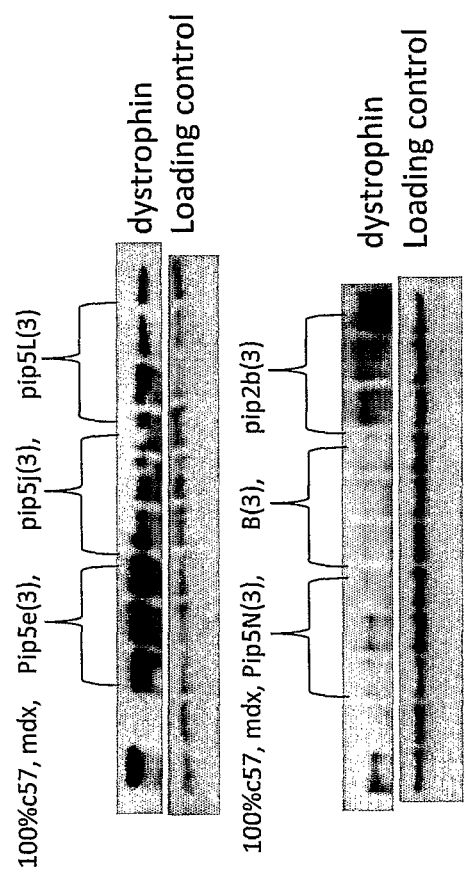

The amount of dystrophin produced can be quantified by Western blotting relative to normal control and Pip-5e, Pip-5j, Pip-5l and Pip-2b showed much higher levels of dystrophin protein produced than B-peptide or Pip-5n (FIG. 24).

Significant levels of exon skipping were seen for all constructs by RT-PCR (data not shown).

Intravenous Administration

Exon skipping can also be assessed by intravenous injection into the tail vein of mdx mice[42]. The mdx mice were injected with an 80 μl dose of PMO-peptide conjugate (Pip5e-PMODMD or B-PMODMD) with saline at a final dose of 25 mg/kg. The mice were killed at 1 week after injection by $CO_2$ inhalation and tissues were removed and snap-frozen in liquid nitrogen-cooled isopentane and stored at −80° C.

Immunohistochemistry and fibre counting was carried out as above. Notably, in heart tissue almost all cardiomyocytes looked to have been corrected by immunostaining and at the RNA level.

Preliminary data has been obtained demonstrating that Pip-5e-PMODMD has significantly higher dystrophin production than B-PMODMD in heart muscle (data not shown).

Conjugation of Pip Peptides to Cyclic Anticancer Peptide

Pip peptides are suitable for enhancing the cellular delivery of peptide cargoes.

The kinase CDK4 has a critical role in cancer development that appears to be unrelated to the kinase activity itself. Because of a recent discovery that CDK1 is co-expressed approximately equally with CDK4 in cancer cells[48], this has led to the hypothesis that this relationship is in some way important in cancer cells, but not in normal cells.

Peptides have been designed (Theryte Ltd) that mimic a hydrophobic region of CDK4 and these have been shown to have weak anticancer activity and cause cancer cells to die (undisclosed data of Theryte). After further structure-activity studies an active compound has emerged, THR-87 with structure cyclo-[PRPvalklclklalPRG] ([SEQ ID NO: 300])—a 17-mer cyclic peptide where lower case letters within brackets are D-amino acids and upper case are L-amino acids). Since the location of CDK4 is expected to be in the cell nucleus, with the aim of enhancing cell delivery and hence anti-cancer activity, we conjugated THR-87 via a disulfide linkage from the single D-Cys residue to Pip-5f peptide for testing in cancer cells.

The C-terminal Cys of THR-87 was activated by dissolving the cyclic peptide in HPLC grade water at a concentration of 5 mM. Aqueous ammonium bicarbonate solution (1 M) was added to make an overall concentration of 0.1 M buffer. Then, 10 equivalents of 2-aidrithiol solution (10 mg/ml) were added, the solution was vortexed, and allowed to stand for 2 hours at room temperature. The product was purified by RP-HPLC on a Jupiter C18 reversed phase column (250×10 mm) with buffer A, 0.1% TFA in water, and buffer B, 90% acetonitrile in 0.1% TFA (gradient: 5%-35% B in 20 minutes) with detection at 218 nm. The product was freeze-dried and then dissolved in 0.1% TFA. The product was analysed by MALDI-TOF mass spectrometry on a Voyager DE Pro using a matrix of α-cyano-4-hydroxycinnamic acid (10 mg/ml) in acetonitrile/3% aqueous trifluoroacetic acid solution. For conjugation of Pip-5f to THR-87), 10 μl (100 nmole) of 10 mM THR-87 solution in 0.1% TFA was placed in a microcentrifuge tube. Formamide (250 μl) was then added and the tube was vortexed. Thiol-activated peptide (200 nmole) was added to the THR-87 solution and vortexed, and then 50 μl of ammonium acetate (10 mM) was added. The tube was vortexed, and allowed to stand at room temperature for 1 hour. The product was purified by RP-HPLC on a Jupiter C18 column (250×10 mm) with buffer A, 5 mM HCl in water, and buffer B, 90% acetonitrile, 10% water, 5 mM HCl (gradient: 10%-50% B in 20 minutes) with detection at 218 nm. The product was freeze-dried and then dissolved in water. The solution was dried using speed vacuum (3 times). The residue was dissolved in sterile water and passed though 0.22 μm filter. The product was analysed by MALDI-TOF mass spectrometry on a Voyager DE Pro using a matrix of α-cyano-4-hydroxycinnamic acid (10 mg/ml) in acetonitrile/3% aqueous trifluoroacetic acid. The concentration of the peptide was determined by amino acid analysis.

Pip-5f-THR-87 conjugate is expected to have enhanced anti-cancer activity.

REFERENCES

1. Kurreck J.: *Eur. J. Biochem.* 2003, 270, 1628.
2. Eckstein F.: *Expert Opin. Biol. Ther.* 2007, 7, 1021.
3. Egholm M., BuchardtO., Nielsen P. E., Berg R. H.: *J. Amer. Chem. Soc.* 1992, 114, 1895.
4. Summerton J., Weller D.: *Antisense Nucl. Acid Drug Dev.* 1997, 7, 187.
5. Lebleu B., Moulton H. M., Abes R., Ivanova G. D., Abes S., Stein D. A., Iversen P. L., Arzumanov A., Gait M. J.: *Adv. Drug Delivery Rev.* 2008, 60, 517.
6. Zatsepin T. S., Turner J. J., Oretskaya T. S., Gait M. J.: *Curr. Pharm. Design* 2005, 11, 3639.
7. Abes R., Arzumanov A., Moulton H. M., Abes S., Ivanova G. D., Iversen P. L., Gait M. J., Lebleu B.: *Biochem. Soc. Trans.* 2007, 35, 775.
8. Turner J. J., Arzumanov A., Ivanova G., Fabani M., Gait M. J.: Cell-Penetrating Peptides, 2nd Edition. (U. Langel Ed.) 2006, CRC Press, Boca Raton. 313.
9. Turner J. J., Jones S., Fabani M., Ivanova G., Arzumanov A., Gait M. J.: *Blood, Cells, Molecules and Diseases* 2007, 38, 1.
10. Kang S.-H., Cho M.-J., Kole R.: *Biochemistry* 1998, 37, 6235.
11. Bendifallah N., Rasmussen F. W., Zachar V., Ebbesen P., Nielsen P. E., Koppelhus U.: *Bioconjugate Chem.* 2006, 17, 750.
12. El-Andaloussi S., Johansson H. J., Lundberg P., Langel U.: *J. Gene Medicine* 2006, 8, 1262.
13. El-Andaloussi S., Johansson H. J., Holm T., Langel U.: *Mol. Ther.* 2007, 15, 1820.
14. Abes S., Williams D., Prevot P., Thierry A. R., Gait M. J., Lebleu B.: *J. Controlled Release* 2006, 110, 595.
15. Abes S., Moulton H. M., Turner J. J., Clair P., Richard J.-P., Iversen P. L., Gait M. J., Lebleu B.: *Biochem. Soc. Trans.* 2007, 35, 53.
16. Abes S., Moulton H. M., Clair P., Prevot P., Youngblood D. S., Wu R. P., Iversen P. L., Lebleu B.: *J. Controlled Release* 2006, 116, 304.
17. Turner J. J., Arzumanov A. A., Gait M. J.: *Nucl. Acids Res.* 2005, 33, 27.
18. Turner J. J., Ivanova G. D., Verbeure B., Williams D., Arzumanov A., Abes S., Lebleu B., Gait M. J.: *Nucl. Acids Res.* 2005, 33, 6837.
19. Abes S., Turner J. J., Ivanova G. D., Owen D., Williams D., Arzumanov A., Clair P., Gait M. J., Lebleu B.: *Nucl. Acids Res.* 2007, 35, 4495.
20. Fabani M., Gait M. J.: *RNA* 2008, 14, 336.

21. Moulton H. M., Nelson M. H., Hatlevig S. A., Reddy M. T., Iversen P. L.: *Bioconjugate Chem.* 2004, 15, 290.
22. Kichler A., Leborgne C, J. M., Danos O., Bechinger B.: *Proc. Nail. Acad. Sci. USA* 2003, 100, 1564.
23. Yin H., Lu Q., Wood M.: *Mol. Ther.* 2008, 16, 38.
24. Fletcher S., Honeyman K., Fall A. M., Harding P. L., Johnsen R. D., Wilton S. D.: *J Gene Med.* 2006, 8, 207.
25. Soifer H. S., Rossi J. J., Saetrom P.: *Mol. Ther.* 2007, 15, 2070.
26. Jopling C. L., Yi M., Lancaster A. M., Lemon S. M., Sarnow P.: *Science* 2005, 309, 1577.
27. Kriitzfeldt J., Rajewsky N., Braich R., Rajeev K. G., Tuschl T., Manoharan M., Stoffel M.: *Nature* 2005, 438, 685.
28. Esau C, Davis S., Murray S. F., Yu X. X., Pandey S. K., Pear M., Watts L., Booten S. L., Graham M., Mckay R., Subramanian A., Propp S., LoHo B. A., Freier S. M., Bennett C. F., Bhanot S., Monia B. P.: *Cell Metabolism* 2006, 3, 87.
29. Cossu, G. and Sampaolesi, M. (2007) *Trends Mol. Medicine,* 13 520-526.
30. Aartsma-Rus, A. and van Ommen, G.-J. B. (2007) *RNA,* 13, 1609-1624. 31. Lu, Q. et al (2005) Proc. Natl. Acad. Sci. USA, 102, 198-203.
33. Alter, J. et al (2006) *Nature Medicine,* 12, 175-177.
34. van Deutekom, J. et al (2007) New England J. Med. 357, 2677-2686.
35. Arechavala-Gomeza, V. et al (2007) *Human Gene Therapy,* 18, 798-810.
36. Lebleu, B. et al. (2008) *Adv. Drug Delivery Rev.* 60, 517-529. 37. Fletcher, S. et al (2007) Mol. Ther. 15, 1587-1592.
38. Madsen, E. C., Morcos, P. A., Mendelsohn, B A, and Gitlin, J. D. (2008) *Proc. Natl. Acad. Sci. USA,* 105, 3909-3914
39. Kole, R. Vacek, M., and Williams T. (2004) *Oligonucleotides,* 14, 65-74).
40. Scaffidi, P. and Mistelli, T. (2006) *Science,* 312, 1059-1063
41. Du, L. et al (2007) *Proc. Natl. Acad. Sci. USA* 104, 6007-6012
42. Yin, H. et al (2008) *Human Mol. Gen.* 17, 3909-3918;
43. Wu. B. et al (2008) *Proc. Natl. Acad. Sci. USA* 105, 14814-14819
44. Jearawiriyapaisarn, N. et al (2008) *Mol. Ther.* 16, 1624-1629
45. Moulton et al. (2004) *Bioconjugate Chem.* 15, 290-299.
46. Seabra, L. and Warenius, H. (2007) Eur. *J. Cancer* 43, 1483-1492.

---

SEQUENCE LISTING

```
<160> NUMBER OF SEQ ID NOS: 304

<210> SEQ ID NO 1
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (25)..(25)
<223> OTHER INFORMATION: Disulfide linked to Cys-Lys-PNA705-Lys-Lys-Lys

<400> SEQUENCE: 1

Arg Arg Arg Arg Arg Arg Arg Gln Ile Lys Ile Trp Phe Gln Asn Arg
1               5                   10                  15

Arg Met Lys Trp Lys Lys Gly Gly Cys
            20                  25

<210> SEQ ID NO 2
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (25)..(25)
<223> OTHER INFORMATION: Thioether linked to
      CH2-CO-Lys-PNA705-Lys-Lys-Lys

<400> SEQUENCE: 2

Arg Arg Arg Arg Arg Arg Arg Gln Ile Lys Ile Trp Phe Gln Asn Arg
1               5                   10                  15

Arg Met Lys Trp Lys Lys Gly Gly Cys
            20                  25

<210> SEQ ID NO 3
<211> LENGTH: 19
```

```
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: 19
<223> OTHER INFORMATION: Disulfide linked to Cys-Lys-PNA705-Lys-Lys-Lys

<400> SEQUENCE: 3

Arg Gln Ile Lys Ile Trp Phe Gln Asn Arg Arg Met Lys Trp Lys Lys
1               5                   10                  15

Gly Gly Cys

<210> SEQ ID NO 4
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: 23
<223> OTHER INFORMATION: Disulfide linked to Cys-Lys-PNA705-Lys-Lys-Lys

<400> SEQUENCE: 4

Arg Arg Arg Arg Arg Arg Arg Gln Ile Lys Ile Trp Phe Gln Asn Arg
1               5                   10                  15

Arg Met Lys Trp Lys Lys Cys
            20

<210> SEQ ID NO 5
<211> LENGTH: 28
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 28
<223> OTHER INFORMATION: Disulfide linked to Cys-Lys-PNA705-Lys-Lys-Lys

<400> SEQUENCE: 5

Arg Xaa Arg Arg Xaa Arg Arg Xaa Arg Arg Gln Ile Lys Ile Trp Phe
1               5                   10                  15

Gln Asn Arg Arg Met Lys Trp Lys Lys Gly Gly Cys
            20                  25

<210> SEQ ID NO 6
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (17)..(17)
<223> OTHER INFORMATION: Xaa is aminohexyl
<220> FEATURE:
```

```
<221> NAME/KEY: SITE
<222> LOCATION: (19)..(19)
<223> OTHER INFORMATION: Xaa is aminohexyl
<220> FEATURE:
<221> NAME/KEY: SITE
<222> LOCATION: (21)..(21)
<223> OTHER INFORMATION: Xaa is aminohexyl
<220> FEATURE:
<221> NAME/KEY: SITE
<222> LOCATION: (23)..(23)
<223> OTHER INFORMATION: Xaa is aminohexyl
<220> FEATURE:
<221> NAME/KEY: SITE
<222> LOCATION: 24
<223> OTHER INFORMATION: Disulfide linked to Cys-Lys-PNA705-Lys-Lys-Lys

<400> SEQUENCE: 6

Arg Arg Arg Arg Arg Arg Arg Gln Ile Lys Ile Leu Phe Gln Asn Arg
1               5                   10                  15

Xaa Arg Xaa Arg Xaa Arg Xaa Cys
            20

<210> SEQ ID NO 7
<211> LENGTH: 13
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is aminohexyl
<220> FEATURE:
<221> NAME/KEY: SITE
<222> LOCATION: (13)..(13)
<223> OTHER INFORMATION: Disulfide linked to Cys-Lys-PNA705-Lys

<400> SEQUENCE: 7

Arg Xaa Arg Arg Xaa Arg Arg Xaa Arg Arg Xaa Arg Cys
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is aminohexyl
```

```
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: 14
<223> OTHER INFORMATION: Disulfide linked to Cys-Lys-PNA705-Lys

<400> SEQUENCE: 8

Arg Xaa Arg Arg Xaa Arg Arg Xaa Arg Arg Xaa Arg Xaa Cys
1               5                  10

<210> SEQ ID NO 9
<211> LENGTH: 26
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 26
<223> OTHER INFORMATION: Disulfide linked to Cys-Lys-PNA705-Lys

<400> SEQUENCE: 9

Arg Xaa Arg Arg Xaa Arg Arg Xaa Arg Ile Lys Ile Leu Phe Gln Asn
1               5                  10                  15

Arg Arg Met Lys Trp Lys Lys Gly Gly Cys
            20                  25

<210> SEQ ID NO 10
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 24
<223> OTHER INFORMATION: Disulfide linked to Cys-Lys-PNA705-Lys

<400> SEQUENCE: 10

Arg Xaa Arg Arg Xaa Arg Arg Xaa Arg Ile Lys Ile Leu Phe Gln Asn
1               5                  10                  15

Arg Arg Met Lys Trp Lys Lys Cys
            20

<210> SEQ ID NO 11
```

```
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 23
<223> OTHER INFORMATION: Disulfide linked to Cys-Lys-PNA705-Lys

<400> SEQUENCE: 11

Arg Xaa Arg Arg Xaa Arg Arg Xaa Arg Ile Lys Ile Leu Phe Gln Asn
1               5                   10                  15

Arg Met Lys Trp Lys Lys Cys
            20

<210> SEQ ID NO 12
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is aminohexyl
<220> FEATURE:
<221> NAME/KEY: SITE
<222> LOCATION: 24
<223> OTHER INFORMATION: Disulfide linked to Cys-Lys-PNA705-Lys

<400> SEQUENCE: 12

Arg Xaa Arg Arg Xaa Arg Arg Xaa Arg Ile Lys Ile Leu Phe Gln Asn
1               5                   10                  15

Xaa Arg Met Lys Trp Lys Lys Cys
            20

<210> SEQ ID NO 13
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
```

```
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 24
<223> OTHER INFORMATION: Disulfide linked to Cys-Lys-PNA705-Lys

<400> SEQUENCE: 13

Arg Xaa Arg Arg Xaa Arg Arg Xaa Arg Ile Lys Ile Leu Phe Gln Asn
1               5                   10                  15

His Arg Met Lys Trp Lys Lys Cys
            20

<210> SEQ ID NO 14
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: SITE
<222> LOCATION: 24
<223> OTHER INFORMATION: Disulfide linked to Cys-Lys-PNA705-Lys

<400> SEQUENCE: 14

Arg Xaa Arg Arg Xaa Arg Arg Xaa Arg Ile Lys Ile Leu Phe Gln Asn
1               5                   10                  15

Xaa Arg Met Lys Trp Lys Lys Cys
            20

<210> SEQ ID NO 15
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is homoArg
<220> FEATURE:
<221> NAME/KEY: SITE
<222> LOCATION: 24
```

<223> OTHER INFORMATION: Disulfide linked to Cys-Lys-PNA705-Lys

<400> SEQUENCE: 15

Arg Xaa Arg Arg Xaa Arg Arg Xaa Arg Ile Lys Ile Leu Phe Gln Asn
1               5                   10                  15

Xaa Arg Met Lys Trp Lys Lys Cys
            20

<210> SEQ ID NO 16
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: 24
<223> OTHER INFORMATION: Disulfide linked to Cys-Lys-PNA705-Lys

<400> SEQUENCE: 16

Arg Xaa Arg Arg Xaa Arg Arg Xaa Arg Ile Lys Ile Leu Phe Gln Asn
1               5                   10                  15

Xaa Arg Met Lys Trp Lys Ala Cys
            20

<210> SEQ ID NO 17
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25

```
<223> OTHER INFORMATION: Disulfide linked to Cys-Lys-PNA705-Lys

<400> SEQUENCE: 17

Arg Xaa Arg Arg Xaa Arg Arg Xaa Arg Ile Lys Ile Leu Phe Gln Asn
1               5                   10                  15

Xaa Arg Met Lys Trp His Lys Ala Cys
            20                  25

<210> SEQ ID NO 18
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: SITE
<222> LOCATION: 24
<223> OTHER INFORMATION: Disulfide linked to Cys-Lys-PNA705-Lys

<400> SEQUENCE: 18

Arg Xaa Arg Arg Xaa Arg Arg Xaa Arg Ile Lys Ile Leu Phe Gln Asn
1               5                   10                  15

Xaa Arg Met Lys Trp His Arg Cys
            20

<210> SEQ ID NO 19
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (4)..(4)
<223> OTHER INFORMATION: Xaa is aminohexyl
<220> FEATURE:
<221> NAME/KEY: SITE
<222> LOCATION: (6)..(6)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 24
<223> OTHER INFORMATION: Disulfide linked to Cys-Lys-PNA705-Lys

<400> SEQUENCE: 19

Arg Xaa Arg Xaa Arg Xaa Arg Xaa Arg Ile Lys Ile Leu Phe Gln Asn
1               5                   10                  15

Arg Arg Met Lys Trp Lys Lys Cys
```

```
<210> SEQ ID NO 20
<211> LENGTH: 24
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: MOD_RES
<222> LOCATION: 2, 4, 6, 8
<223> OTHER INFORMATION: bAla
<220> FEATURE:
<221> NAME/KEY: SITE
<222> LOCATION: 24
<223> OTHER INFORMATION: Disulfide linked to Cys-Lys-PNA705-Lys

<400> SEQUENCE: 20

Arg Ala Arg Ala Arg Ala Arg Ala Arg Ile Lys Ile Leu Phe Gln Asn
1               5                   10                  15

Arg Arg Met Lys Trp Lys Lys Cys
            20

<210> SEQ ID NO 21
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: (24)
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 21

Arg Xaa Arg Arg Xaa Arg Arg Xaa Arg Ile Xaa Ile Leu Phe Gln Asn
1               5                   10                  15

Xaa Arg Met Lys Trp His Lys Ala Cys
            20                  25

<210> SEQ ID NO 22
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
```

```
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 22

Arg Xaa Arg Arg Xaa Arg Arg Xaa Arg Ile His Ile Leu Phe Gln Asn
1               5                   10                  15

Xaa Arg Met Lys Trp His Lys Ala Cys
            20                  25

<210> SEQ ID NO 23
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 23

Arg Xaa Arg Arg Xaa Arg Arg Xaa Arg Ile Arg Ile Leu Phe Gln Asn
1               5                   10                  15

Xaa Arg Met Lys Trp His Lys Ala Cys
            20                  25

<210> SEQ ID NO 24
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
```

```
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 24

Arg Xaa Arg Arg Xaa Arg Arg Xaa Arg Ile Xaa Ile Leu Phe Gln Tyr
1               5                   10                  15

Xaa Arg Met Lys Trp His Lys Ala Cys
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: 18
<223> OTHER INFORMATION: Xaa is D-Arg
<220> FEATURE:
<221> NAME/KEY: MOD_RES
<222> LOCATION: 25
<223> OTHER INFORMATION: bAla
<220> FEATURE:
<221> NAME/KEY: SITE
<222> LOCATION: 26
<223> OTHER INFORMATION: Disulfide linked to Cys-Lys-PNA705-Lys

<400> SEQUENCE: 25

Arg Xaa Arg Arg Xaa Arg Arg Xaa Arg Leu Tyr Ser Pro Leu Ser Phe
1               5                   10                  15

Gln Xaa Arg Met Lys Trp His Lys Ala Cys
            20                  25

<210> SEQ ID NO 26
<211> LENGTH: 25
<212> TYPE: PRT
<213> ORGANISM: Artificial sequence
<220> FEATURE:
```

```
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 26

Arg Xaa Arg Arg Xaa Arg Arg Xaa Arg Ile Ser Ile Leu Phe Gln Tyr
1               5                   10                  15

Xaa Arg Met Lys Trp His Lys Ala Cys
            20                  25

<210> SEQ ID NO 27
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)
<223> OTHER INFORMATION: Xaa is D-Arg
<220> FEATURE:
<221> NAME/KEY: MOD_RES
<222> LOCATION: 22
<223> OTHER INFORMATION: bAla
<220> FEATURE:
<221> NAME/KEY: SITE
<222> LOCATION: 23
<223> OTHER INFORMATION: Disulfide linked to Cys-Lys-PNA705-Lys

<400> SEQUENCE: 27

Arg Xaa Arg Arg Xaa Arg Arg Xaa Arg Ile Leu Phe Gln Tyr Xaa Arg
1               5                   10                  15

Met Lys Trp His Lys Ala Cys
            20

<210> SEQ ID NO 28
<211> LENGTH: 22
<212> TYPE: PRT
<213> ORGANISM: Artificial sequence
<220> FEATURE:
```

```
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: 8, 14
<223> OTHER INFORMATION: Xaa is D-Arg
<220> FEATURE:
<221> NAME/KEY: MOD_RES
<222> LOCATION: 21
<223> OTHER INFORMATION: bAla
<220> FEATURE:
<221> NAME/KEY: SITE
<222> LOCATION: 22
<223> OTHER INFORMATION: Disulfide linked to Cys-Lys-PNA705-Lys

<400> SEQUENCE: 28

Arg Xaa Arg Arg Xaa Arg Ile Xaa Ile Leu Phe Gln Tyr Xaa Arg Met
 1               5                  10                  15

Lys Trp His Lys Ala Cys
            20

<210> SEQ ID NO 29
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 29

Arg Xaa Arg Arg Ala Arg Arg Xaa Arg Ile His Ile Leu Phe Gln Tyr
 1               5                  10                  15

Xaa Arg Met Lys Trp His Lys Ala Cys
            20                  25

<210> SEQ ID NO 30
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: MOD_RES
<222> LOCATION: 2, 8
<223> OTHER INFORMATION: bAla
<220> FEATURE:
<221> NAME/KEY: SITE
<222> LOCATION: (5)..(5)
```

-continued

```
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 30

Arg Ala Arg Arg Xaa Arg Arg Ala Arg Ile His Ile Leu Phe Gln Tyr
1               5                   10                  15

Xaa Arg Met Lys Trp His Lys Ala Cys
            20                  25

<210> SEQ ID NO 31
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Disulfide linked to Cys-Lys-PNA705-Lys

<400> SEQUENCE: 31

Arg Xaa Arg Arg Xaa Arg Arg Xaa Arg Ile His Ile Leu Phe Gln Tyr
1               5                   10                  15

Xaa Arg Met Lys Trp His Lys Ala Cys
            20                  25

<210> SEQ ID NO 32
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
```

<223> OTHER INFORMATION: Xaa is aminohexyl
<220> FEATURE:
<221> NAME/KEY: SITE
<222> LOCATION: 11
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: (25)..(25)
<223> OTHER INFORMATION: Thioether linked to CH2-CO-Lys-PNADMD-Lys

<400> SEQUENCE: 32

Arg Xaa Arg Arg Xaa Arg Arg Xaa Arg Ile Xaa Ile Leu Phe Gln Asn
1               5                   10                  15

Xaa Arg Met Lys Trp His Lys Ala Cys
            20                  25

<210> SEQ ID NO 33
<211> LENGTH: 25
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: (25)..(25)
<223> OTHER INFORMATION: Thioether linked to CH2-CO-Lys-PNADMD-Lys

<400> SEQUENCE: 33

Arg Xaa Arg Arg Xaa Arg Arg Xaa Arg Ile His Ile Leu Phe Gln Asn
1               5                   10                  15

Xaa Arg Met Lys Trp His Lys Ala Cys
            20                  25

<210> SEQ ID NO 34
<211> LENGTH: 23
<212> TYPE: PRT
<213> ORGANISM: Artificial sequence
<220> FEATURE:
<223> OTHER INFORMATION: Synthetic sequence: Domain 1-3 peptide
      sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE

```
<222> LOCATION: (5)..(5)
<223> OTHER INFORMATION: Xaa is aminohexyl
<220> FEATURE:
<221> NAME/KEY: SITE
<222> LOCATION: (8)..(8)
<223> OTHER INFORMATION: Xaa is aminohexyl

<400> SEQUENCE: 34

Arg Xaa Arg Arg Xaa Arg Arg Xaa Arg Ile Lys Ile Leu Phe Gln Asn
1               5                   10                  15

Arg Arg Met Lys Trp His Lys
            20

<210> SEQ ID NO 35
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 35

Arg Xaa Arg Arg Xaa Arg Arg Xaa Arg Ile Lys Ile Leu Phe Gln Asn
1               5                   10                  15

Xaa Arg Met Lys Trp His Lys
            20

<210> SEQ ID NO 36
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys

<400> SEQUENCE: 36

Arg Xaa Arg Arg Xaa Arg Arg Xaa Arg Ile Xaa Ile Leu Phe Gln Asn
1               5                   10                  15

Arg Arg Met Lys Trp His Lys
            20

<210> SEQ ID NO 37
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
```

<222> LOCATION: (17)..(17)
<223> OTHER INFORMATION: Xaa is D-Arg

<400> SEQUENCE: 37

Arg Xaa Arg Arg Xaa Arg Arg Xaa Arg Ile Xaa Ile Leu Phe Gln Asn
1               5                   10                  15

Xaa Arg Met Lys Trp His Lys
            20

<210> SEQ ID NO 38
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 38

Arg Xaa Arg Arg Xaa Arg Arg Xaa Arg Ile His Ile Leu Phe Gln Asn
1               5                   10                  15

Arg Arg Met Lys Trp His Lys
            20

<210> SEQ ID NO 39
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 39

Arg Xaa Arg Arg Xaa Arg Arg Xaa Arg Ile His Ile Leu Phe Gln Asn
1               5                   10                  15

Xaa Arg Met Lys Trp His Lys
            20

<210> SEQ ID NO 40
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 40

Arg Xaa Arg Arg Xaa Arg Arg Xaa Arg Ile Arg Ile Leu Phe Gln Asn
1               5                   10                  15

Arg Arg Met Lys Trp His Lys
            20

<210> SEQ ID NO 41
<211> LENGTH: 23
<212> TYPE: PRT
<213> ORGANISM: Artificial sequence

```
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 41

Arg Xaa Arg Arg Xaa Arg Arg Xaa Arg Ile Arg Ile Leu Phe Gln Asn
1               5                   10                  15

Xaa Arg Met Lys Trp His Lys
            20

<210> SEQ ID NO 42
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 42

Arg Xaa Arg Arg Xaa Arg Arg Xaa Arg Ile Ile Leu Phe Gln Asn Arg
1               5                   10                  15

Arg Met Lys Trp His Lys
            20

<210> SEQ ID NO 43
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 43

Arg Xaa Arg Arg Xaa Arg Arg Xaa Arg Ile Ile Leu Phe Gln Asn Xaa
1               5                   10                  15

Arg Met Lys Trp His Lys
            20

<210> SEQ ID NO 44
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 44

Arg Xaa Arg Arg Xaa Arg Arg Xaa Arg Lys Ile Leu Phe Gln Asn Arg
1               5                   10                  15
```

Arg Met Lys Trp His Lys
        20

<210> SEQ ID NO 45
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 45

Arg Xaa Arg Arg Xaa Arg Arg Xaa Arg Lys Ile Leu Phe Gln Asn Xaa
1               5                   10                  15

Arg Met Lys Trp His Lys
        20

<210> SEQ ID NO 46
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (10)..(10)
<223> OTHER INFORMATION: Xaa is D-Lys

<400> SEQUENCE: 46

Arg Xaa Arg Arg Xaa Arg Arg Xaa Arg Xaa Ile Leu Phe Gln Asn Arg
1               5                   10                  15

Arg Met Lys Trp His Lys
        20

<210> SEQ ID NO 47
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (10)..(10)
<223> OTHER INFORMATION: Xaa is D-Lys
<220> FEATURE:
<221> NAME/KEY: SITE
<222> LOCATION: 16
<223> OTHER INFORMATION: Xaa is D-Arg

<400> SEQUENCE: 47

Arg Xaa Arg Arg Xaa Arg Arg Xaa Arg Xaa Ile Leu Phe Gln Asn Xaa
1               5                   10                  15

Arg Met Lys Trp His Lys
        20

```
<210> SEQ ID NO 48
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 48

Arg Xaa Arg Arg Xaa Arg Arg Xaa Arg His Ile Leu Phe Gln Asn Arg
1               5                   10                  15

Arg Met Lys Trp His Lys
            20

<210> SEQ ID NO 49
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 49

Arg Xaa Arg Arg Xaa Arg Arg Xaa Arg His Ile Leu Phe Gln Asn Xaa
1               5                   10                  15

Arg Met Lys Trp His Lys
            20

<210> SEQ ID NO 50
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 50

Arg Xaa Arg Arg Xaa Arg Arg Xaa Arg Ile Leu Phe Gln Asn Arg
1               5                   10                  15

Arg Met Lys Trp His Lys
            20

<210> SEQ ID NO 51
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 51
```

```
Arg Xaa Arg Arg Xaa Arg Arg Xaa Arg Ile Leu Phe Gln Asn Xaa
1               5                   10                  15

Arg Met Lys Trp His Lys
            20
```

```
<210> SEQ ID NO 52
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 52
```

```
Arg Xaa Arg Arg Xaa Arg Arg Xaa Arg Ile Leu Phe Gln Asn Arg Arg
1               5                   10                  15

Met Lys Trp His Lys
            20
```

```
<210> SEQ ID NO 53
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 15
<223> OTHER INFORMATION: Xaa is D-Arg

<400> SEQUENCE: 53
```

```
Arg Xaa Arg Arg Xaa Arg Arg Xaa Arg Ile Leu Phe Gln Asn Xaa Arg
1               5                   10                  15

Met Lys Trp His Lys
            20
```

```
<210> SEQ ID NO 54
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 54
```

```
Arg Xaa Arg Arg Xaa Arg Arg Xaa Arg Ile Lys Ile Leu Phe Gln Tyr
1               5                   10                  15

Arg Arg Met Lys Trp His Lys
            20
```

```
<210> SEQ ID NO 55
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
```

```
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 55

Arg Xaa Arg Arg Xaa Arg Arg Xaa Arg Ile Lys Ile Leu Phe Gln Tyr
1               5                   10                  15

Xaa Arg Met Lys Trp His Lys
            20

<210> SEQ ID NO 56
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys

<400> SEQUENCE: 56

Arg Xaa Arg Arg Xaa Arg Arg Xaa Arg Ile Xaa Ile Leu Phe Gln Tyr
1               5                   10                  15

Arg Arg Met Lys Trp His Lys
            20

<210> SEQ ID NO 57
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg

<400> SEQUENCE: 57

Arg Xaa Arg Arg Xaa Arg Arg Xaa Arg Ile Xaa Ile Leu Phe Gln Tyr
1               5                   10                  15

Xaa Arg Met Lys Trp His Lys
            20

<210> SEQ ID NO 58
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 58
```

```
Arg Xaa Arg Arg Xaa Arg Arg Xaa Arg Ile His Ile Leu Phe Gln Tyr
1               5                   10                  15

Arg Arg Met Lys Trp His Lys
            20

<210> SEQ ID NO 59
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 59

Arg Xaa Arg Arg Xaa Arg Arg Xaa Arg Ile His Ile Leu Phe Gln Tyr
1               5                   10                  15

Xaa Arg Met Lys Trp His Lys
            20

<210> SEQ ID NO 60
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 60

Arg Xaa Arg Arg Xaa Arg Arg Xaa Arg Ile Arg Ile Leu Phe Gln Tyr
1               5                   10                  15

Arg Arg Met Lys Trp His Lys
            20

<210> SEQ ID NO 61
<211> LENGTH: 23
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg

<400> SEQUENCE: 61

Arg Xaa Arg Arg Xaa Arg Arg Xaa Arg Ile Arg Ile Leu Phe Gln Tyr
1               5                   10                  15

Xaa Arg Met Lys Trp His Lys
            20

<210> SEQ ID NO 62
<211> LENGTH: 22
<212> TYPE: PRT
<213> ORGANISM: Artificial sequence
```

```
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 62

Arg Xaa Arg Arg Xaa Arg Arg Xaa Arg Ile Ile Leu Phe Gln Tyr Arg
1               5                   10                  15

Arg Met Lys Trp His Lys
            20

<210> SEQ ID NO 63
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 63

Arg Xaa Arg Arg Xaa Arg Arg Xaa Arg Ile Ile Leu Phe Gln Tyr Xaa
1               5                   10                  15

Arg Met Lys Trp His Lys
            20

<210> SEQ ID NO 64
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 64

Arg Xaa Arg Arg Xaa Arg Arg Xaa Arg Lys Ile Leu Phe Gln Tyr Arg
1               5                   10                  15

Arg Met Lys Trp His Lys
            20

<210> SEQ ID NO 65
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 65

Arg Xaa Arg Arg Xaa Arg Arg Xaa Arg Lys Ile Leu Phe Gln Tyr Xaa
1               5                   10                  15
```

```
<210> SEQ ID NO 66
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (10)..(10)
<223> OTHER INFORMATION: Xaa is D-Lys

<400> SEQUENCE: 66

Arg Xaa Arg Arg Xaa Arg Arg Xaa Arg Xaa Ile Leu Phe Gln Tyr Arg
1               5                   10                  15

Arg Met Lys Trp His Lys
            20

<210> SEQ ID NO 67
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (10)..(10)
<223> OTHER INFORMATION: Xaa is D-Lys
<220> FEATURE:
<221> NAME/KEY: SITE
<222> LOCATION: 16
<223> OTHER INFORMATION: Xaa is D-Arg

<400> SEQUENCE: 67

Arg Xaa Arg Arg Xaa Arg Arg Xaa Arg Xaa Ile Leu Phe Gln Tyr Xaa
1               5                   10                  15

Arg Met Lys Trp His Lys
            20

<210> SEQ ID NO 68
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 68

Arg Xaa Arg Arg Xaa Arg Arg Xaa Arg His Ile Leu Phe Gln Tyr Arg
1               5                   10                  15

Arg Met Lys Trp His Lys
            20

<210> SEQ ID NO 69
<211> LENGTH: 22
<212> TYPE: PRT
<213> ORGANISM: Artificial sequence
```

```
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 69

Arg Xaa Arg Arg Xaa Arg Arg Xaa Arg His Ile Leu Phe Gln Tyr Xaa
1               5                   10                  15

Arg Met Lys Trp His Lys
            20

<210> SEQ ID NO 70
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 70

Arg Xaa Arg Arg Xaa Arg Arg Xaa Arg Arg Ile Leu Phe Gln Tyr Arg
1               5                   10                  15

Arg Met Lys Trp His Lys
            20

<210> SEQ ID NO 71
<211> LENGTH: 22
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 16
<223> OTHER INFORMATION: Xaa is D-Arg

<400> SEQUENCE: 71

Arg Xaa Arg Arg Xaa Arg Arg Xaa Arg Arg Ile Leu Phe Gln Tyr Xaa
1               5                   10                  15

Arg Met Lys Trp His Lys
            20

<210> SEQ ID NO 72
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl

<400> SEQUENCE: 72

Arg Xaa Arg Arg Xaa Arg Arg Xaa Arg Ile Leu Phe Gln Tyr Arg Arg
1               5                   10                  15
```

```
Met Lys Trp His Lys
            20

<210> SEQ ID NO 73
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 15
<223> OTHER INFORMATION: Xaa is D-Arg

<400> SEQUENCE: 73

Arg Xaa Arg Arg Xaa Arg Arg Xaa Arg Ile Leu Phe Gln Tyr Xaa Arg
1               5                   10                  15

Met Lys Trp His Lys
            20

<210> SEQ ID NO 74
<211> LENGTH: 6
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: VARIANT
<222> LOCATION: 2, 5
<223> OTHER INFORMATION: Xaa is aminohexyl, beta-alanyl, p-aminobenzoyl,
      isonipecotyl, or Aib

<400> SEQUENCE: 74

Arg Xaa Arg Arg Xaa Arg
1               5

<210> SEQ ID NO 75
<211> LENGTH: 9
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: VARIANT
<222> LOCATION: (2, 5, 8)
<223> OTHER INFORMATION: Xaa is aminohexyl, beta-alanyl, p-aminobenzoyl,
      isonipecotyl, or Aib

<400> SEQUENCE: 75

Arg Xaa Arg Arg Xaa Arg Arg Xaa Arg
1               5

<210> SEQ ID NO 76
<211> LENGTH: 12
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: VARIANT
<222> LOCATION: (2, 5, 8, 11)
<223> OTHER INFORMATION: Xaa is aminohexyl, beta-alanyl, p-aminobenzoyl,
      isonipecotyl, or Aib

<400> SEQUENCE: 76

Arg Xaa Arg Arg Xaa Arg Arg Xaa Arg Arg Xaa Arg
1               5                   10
```

```
<210> SEQ ID NO 77
<211> LENGTH: 6
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: MOD_RES
<222> LOCATION: 2, 5
<223> OTHER INFORMATION: bAla

<400> SEQUENCE: 77

Arg Ala Arg Arg Ala Arg
1               5

<210> SEQ ID NO 78
<211> LENGTH: 9
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: MOD_RES
<222> LOCATION: 2, 5, 8
<223> OTHER INFORMATION: bAla

<400> SEQUENCE: 78

Arg Ala Arg Arg Ala Arg Arg Ala Arg
1               5

<210> SEQ ID NO 79
<211> LENGTH: 12
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: MOD_RES
<222> LOCATION: 2, 5, 8, 11
<223> OTHER INFORMATION: bAla

<400> SEQUENCE: 79

Arg Ala Arg Arg Ala Arg Arg Ala Arg Arg Ala Arg
1               5                   10

<210> SEQ ID NO 80
<211> LENGTH: 8
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: VARIANT
<222> LOCATION: (2, 5)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (8)..(8)
<223> OTHER INFORMATION: Xaa is D-Arg

<400> SEQUENCE: 80

Arg Xaa Arg Arg Xaa Arg Ile Xaa
1               5

<210> SEQ ID NO 81
<211> LENGTH: 9
<212> TYPE: PRT
<213> ORGANISM: Artificial sequence
<220> FEATURE:
```

```
<223> OTHER INFORMATION: Synthetic sequence: Domain 1 sequence
<220> FEATURE:
<221> NAME/KEY: VARIANT
<222> LOCATION: (2, 8)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: 5
<223> OTHER INFORMATION: bAla

<400> SEQUENCE: 81

Arg Xaa Arg Arg Ala Arg Arg Xaa Arg
1               5

<210> SEQ ID NO 82
<211> LENGTH: 9
<212> TYPE: PRT
<213> ORGANISM: Artificial sequence
<220> FEATURE:
<223> OTHER INFORMATION: Synthetic sequence: Domain 1 sequence
<220> FEATURE:
<221> NAME/KEY: VARIANT
<222> LOCATION: (5)..(5)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (2, 8)
<223> OTHER INFORMATION: bAla

<400> SEQUENCE: 82

Arg Ala Arg Arg Xaa Arg Arg Ala Arg
1               5

<210> SEQ ID NO 83
<211> LENGTH: 5
<212> TYPE: PRT
<213> ORGANISM: Artificial sequence
<220> FEATURE:
<223> OTHER INFORMATION: Synthetic sequence: Domain 1 sequence

<400> SEQUENCE: 83

Arg Arg Arg Arg Arg
1               5

<210> SEQ ID NO 84
<211> LENGTH: 6
<212> TYPE: PRT
<213> ORGANISM: Artificial sequence
<220> FEATURE:
<223> OTHER INFORMATION: Synthetic sequence: Domain 1 sequence

<400> SEQUENCE: 84

Arg Arg Arg Arg Arg Arg
1               5

<210> SEQ ID NO 85
<211> LENGTH: 7
<212> TYPE: PRT
<213> ORGANISM: Artificial sequence
<220> FEATURE:
<223> OTHER INFORMATION: Synthetic sequence: Domain 1 sequence

<400> SEQUENCE: 85

Arg Arg Arg Arg Arg Arg Arg
1               5

<210> SEQ ID NO 86
<211> LENGTH: 4
```

```
<212> TYPE: PRT
<213> ORGANISM: Artificial sequence
<220> FEATURE:
<223> OTHER INFORMATION: Synthetic sequence: Domain 2 sequence

<400> SEQUENCE: 86

Ile Leu Phe Gln
1

<210> SEQ ID NO 87
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 87

Ile Leu Phe Gln Asn
1               5

<210> SEQ ID NO 88
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 88

Ile Leu Phe Gln Tyr
1               5

<210> SEQ ID NO 89
<211> LENGTH: 7
<212> TYPE: PRT
<213> ORGANISM: Artificial sequence
<220> FEATURE:
<223> OTHER INFORMATION: Synthetic sequence: Generic domain 2 sequence
<220> FEATURE:
<221> NAME/KEY: VARIANT
<222> LOCATION: (1)..(1)
<223> OTHER INFORMATION: Xaa may be present or absent. If present, Xaa
      is Ile.
<220> FEATURE:
<221> NAME/KEY: VARIANT
<222> LOCATION: (2)..(2)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (7)..(7)
<223> OTHER INFORMATION: Xaa is Asn or Tyr

<400> SEQUENCE: 89

Xaa Xaa Ile Leu Phe Gln Xaa
1               5

<210> SEQ ID NO 90
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 90

Ile Lys Ile Leu Phe Gln Asn
1               5

<210> SEQ ID NO 91
<211> LENGTH: 7
<212> TYPE: PRT
```

```
<213> ORGANISM: Artificial sequence
<220> FEATURE:
<223> OTHER INFORMATION: Synthetic sequence: Domain 2 sequence

<400> SEQUENCE: 91

Ile Lys Ile Leu Phe Gln Tyr
1               5

<210> SEQ ID NO 92
<211> LENGTH: 7
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (2)..(2)
<223> OTHER INFORMATION: Xaa is D-Lys

<400> SEQUENCE: 92

Ile Xaa Ile Leu Phe Gln Asn
1               5

<210> SEQ ID NO 93
<211> LENGTH: 7
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (2)..(2)
<223> OTHER INFORMATION: Xaa is D-Lys

<400> SEQUENCE: 93

Ile Xaa Ile Leu Phe Gln Tyr
1               5

<210> SEQ ID NO 94
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 94

Ile His Ile Leu Phe Gln Asn
1               5

<210> SEQ ID NO 95
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 95

Ile His Ile Leu Phe Gln Tyr
1               5

<210> SEQ ID NO 96
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 96

Ile Arg Ile Leu Phe Gln Asn
```

<210> SEQ ID NO 97
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 97

Ile Arg Ile Leu Phe Gln Tyr
1               5

<210> SEQ ID NO 98
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 98

Ile Ile Leu Phe Gln Asn
1               5

<210> SEQ ID NO 99
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 99

Ile Ile Leu Phe Gln Tyr
1               5

<210> SEQ ID NO 100
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 100

Lys Ile Leu Phe Gln Asn
1               5

<210> SEQ ID NO 101
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 101

Lys Ile Leu Phe Gln Tyr
1               5

<210> SEQ ID NO 102
<211> LENGTH: 6
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: 1
<223> OTHER INFORMATION: Xaa is D-Lys

<400> SEQUENCE: 102

```
Xaa Ile Leu Phe Gln Asn
1               5

<210> SEQ ID NO 103
<211> LENGTH: 6
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: 1
<223> OTHER INFORMATION: Xaa is D-Lys

<400> SEQUENCE: 103

Xaa Ile Leu Phe Gln Tyr
1               5

<210> SEQ ID NO 104
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 104

His Ile Leu Phe Gln Asn
1               5

<210> SEQ ID NO 105
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 105

His Ile Leu Phe Gln Tyr
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 106

Arg Ile Leu Phe Gln Asn
1               5

<210> SEQ ID NO 107
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 107

Arg Ile Leu Phe Gln Tyr
1               5

<210> SEQ ID NO 108
<211> LENGTH: 5
<212> TYPE: PRT
<213> ORGANISM: Artificial sequence
<220> FEATURE:
<223> OTHER INFORMATION: Synthetic sequence: Domain 2 sequence
```

```
<400> SEQUENCE: 108

Ile Leu Phe Gln Asn
1               5

<210> SEQ ID NO 109
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 109

Ile Leu Phe Gln Tyr
1               5

<210> SEQ ID NO 110
<211> LENGTH: 7
<212> TYPE: PRT
<213> ORGANISM: Artificial sequence
<220> FEATURE:
<223> OTHER INFORMATION: Synthetic sequence: Domain 3 sequence

<400> SEQUENCE: 110

Arg Arg Met Lys Trp His Lys
1               5

<210> SEQ ID NO 111
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: SITE
<222> LOCATION: (1)..(1)
<223> OTHER INFORMATION: Xaa is D-Arg

<400> SEQUENCE: 111

Xaa Arg Met Lys Trp His Lys
1               5

<210> SEQ ID NO 112
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
```

```
          In an embodiment, Xaa1 - 6 is absent and Xaa7-12 is
          (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
          Xaa5 - 12 is (Arg)8. In an embodiment, Xaa1 - 5 is absent and
          Xaa6 - 12 is (Arg)7. In an embodiment, Xaa1 - 6 is absent and
          Xaa7 - 12 is (Arg)6. In an embodiment, Xaa1 - 7 is absent and
          Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
          Xaa5 - 12 is Arg - Xaa - Arg - Arg - Xaa - Arg - Ile - D-Arg (SEQ
          ID NO: 80) wherein Xaa is aminohexyl, beta-alanyl, p-aminobenzoyl,
          isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
          Xaa4 - 12 is Arg - Xaa - Arg - Arg - Ala - Arg - Arg - Xaa - Arg
          (SEQ ID NO: 81) wherein Xaa is aminohexyl, beta-alanyl,
          p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
          Xaa4 - 12 is Arg - Ala - Arg - Arg - Xaa - Arg - Arg - Ala - Arg
          (SEQ ID NO: 82) wherein Xaa is aminohexyl, beta-alanyl,
          p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
          is Ile.
<220> FEATURE:
<221> NAME/KEY: VARIANT
<222> LOCATION: (14)..(14)
<223> OTHER INFORMATION: Xaa may be present or absent. If present, Xaa
          is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 112

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Met Lys Trp His Lys
            20                  25

<210> SEQ ID NO 113
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
          (Arg - Xaa - Arg)4 wherein Xaa is aminohexyl, beta-alanyl,
          p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
          4-12 is (Arg - Xaa - Arg)3 wherein Xaa is aminohexyl, beta-alanyl,
```

```
        p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 113

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Met Lys Trp His Lys
            20                  25

<210> SEQ ID NO 114
<211> LENGTH: 18
<212> TYPE: DNA
<213> ORGANISM: Artificial sequence
<220> FEATURE:
<223> OTHER INFORMATION: Synthetic sequence: PNA cargo PNA705

<400> SEQUENCE: 114
```

```
cctcttacct cagttaca                                                 18
```

<210> SEQ ID NO 115
<211> LENGTH: 20
<212> TYPE: DNA
<213> ORGANISM: Artificial sequence
<220> FEATURE:
<223> OTHER INFORMATION: Synthetic sequence: PNA cargo PNADMD

<400> SEQUENCE: 115

```
ggccaaacct cggcttacct                                               20
```

<210> SEQ ID NO 116
<211> LENGTH: 25
<212> TYPE: PRT
<213> ORGANISM: Artificial sequence
<220> FEATURE:
<223> OTHER INFORMATION: Synthetic sequence: Disulfide conjugate of
      CKPNA705K3

<400> SEQUENCE: 116

Arg Arg Arg Arg Arg Arg Arg Gln Ile Lys Ile Trp Phe Gln Asn Arg
1               5                   10                  15

Arg Met Lys Trp Lys Lys Gly Gly Cys
            20                  25

<210> SEQ ID NO 117
<211> LENGTH: 23
<212> TYPE: PRT
<213> ORGANISM: Artificial sequence
<220> FEATURE:
<223> OTHER INFORMATION: Synthetic sequence: Disulfide conjugate of
      CKPNA705K3

<400> SEQUENCE: 117

Arg Arg Arg Arg Arg Arg Arg Gln Ile Lys Ile Trp Phe Gln Asn Arg
1               5                   10                  15

Arg Met Lys Trp Lys Lys Cys
            20

<210> SEQ ID NO 118
<211> LENGTH: 28
<212> TYPE: PRT
<213> ORGANISM: Artificial sequence
<220> FEATURE:
<223> OTHER INFORMATION: Synthetic sequence: Disulfide conjugate of
      CKPNA705K3
<220> FEATURE:
<221> NAME/KEY: SITE
<222> LOCATION: 2, 5, 8
<223> OTHER INFORMATION: Xaa is aminohexyl

<400> SEQUENCE: 118

Arg Xaa Arg Arg Xaa Arg Arg Xaa Arg Arg Gln Ile Lys Ile Trp Phe
1               5                   10                  15

Gln Asn Arg Arg Met Lys Trp Lys Lys Gly Gly Cys
            20                  25

<210> SEQ ID NO 119
<211> LENGTH: 25
<212> TYPE: PRT
<213> ORGANISM: Artificial sequence
<220> FEATURE:
<223> OTHER INFORMATION: Synthetic sequence: Disulfide conjugate of
      CKPNA705K3

<400> SEQUENCE: 119

```
Arg Arg Arg Arg Arg Arg Arg Gln Ile Lys Ile Leu Phe Gln Asn Pro
1               5                   10                  15

Lys Lys Lys Arg Lys Val Gly Gly Cys
            20              25

<210> SEQ ID NO 120
<211> LENGTH: 24
<212> TYPE: PRT
<213> ORGANISM: Artificial sequence
<220> FEATURE:
<223> OTHER INFORMATION: Synthetic sequence: Disulfide conjugate of
      CKPNA705K3
<220> FEATURE:
<221> NAME/KEY: SITE
<222> LOCATION: (17)..(17)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl
<220> FEATURE:
<221> NAME/KEY: SITE
<222> LOCATION: (21)..(21)
<223> OTHER INFORMATION: Xaa is aminohexyl
<220> FEATURE:
<221> NAME/KEY: SITE
<222> LOCATION: (23)..(23)
<223> OTHER INFORMATION: Xaa is aminohexyl

<400> SEQUENCE: 120

Arg Arg Arg Arg Arg Arg Arg Gln Ile Lys Ile Leu Phe Gln Asn Arg
1               5                   10                  15

Xaa Arg Xaa Arg Xaa Arg Xaa Cys
            20

<210> SEQ ID NO 121
<211> LENGTH: 25
<212> TYPE: PRT
<213> ORGANISM: Artificial sequence
<220> FEATURE:
<223> OTHER INFORMATION: Synthetic sequence: Disulfide conjugate of
      CKPNA705K

<400> SEQUENCE: 121

Arg Arg Arg Arg Arg Arg Arg Gln Ile Lys Ile Trp Phe Gln Asn Arg
1               5                   10                  15

Arg Met Lys Trp Lys Lys Gly Gly Cys
            20              25

<210> SEQ ID NO 122
<211> LENGTH: 16
<212> TYPE: PRT
<213> ORGANISM: Artificial sequence
<220> FEATURE:
<223> OTHER INFORMATION: Synthetic sequence: Disulfide conjugate of
      CKPNA705K

<400> SEQUENCE: 122

His His Phe Phe Arg Arg Arg Arg Arg Arg Arg Arg Phe Phe Cys
1               5                   10                  15

<210> SEQ ID NO 123
<211> LENGTH: 18
<212> TYPE: PRT
<213> ORGANISM: Artificial sequence
<220> FEATURE:
<223> OTHER INFORMATION: Synthetic sequence: Disulfide conjugate of
      CKPNA705K
```

<400> SEQUENCE: 123

His His His His His His Arg Arg Arg Arg Arg Arg Arg Arg Phe
1               5                   10                  15

Phe Cys

<210> SEQ ID NO 124
<211> LENGTH: 20
<212> TYPE: PRT
<213> ORGANISM: Artificial sequence
<220> FEATURE:
<223> OTHER INFORMATION: Synthetic sequence: Disulfide conjugate of
      CKPNA705K

<400> SEQUENCE: 124

His His His His His His Phe Phe Arg Arg Arg Arg Arg Arg Arg
1               5                   10                  15

Arg Phe Phe Cys
            20

<210> SEQ ID NO 125
<211> LENGTH: 19
<212> TYPE: PRT
<213> ORGANISM: Artificial sequence
<220> FEATURE:
<223> OTHER INFORMATION: Synthetic sequence: Disulfide conjugate of
      CKPNA705K
<220> FEATURE:
<221> NAME/KEY: SITE
<222> LOCATION: (6)..(7)
<223> OTHER INFORMATION: Xaa is aminohexyl

<400> SEQUENCE: 125

His His His His His Xaa Xaa Arg Arg Arg Arg Arg Arg Arg Arg
1               5                   10                  15

Phe Phe Cys

<210> SEQ ID NO 126
<211> LENGTH: 22
<212> TYPE: PRT
<213> ORGANISM: Artificial sequence
<220> FEATURE:
<223> OTHER INFORMATION: Synthetic sequence: Disulfide conjugate of
      CKPNA705K
<220> FEATURE:
<221> NAME/KEY: SITE
<222> LOCATION: (7)..(8)
<223> OTHER INFORMATION: Xaa is aminohexyl

<400> SEQUENCE: 126

His His His His His His Xaa Xaa Phe Phe Arg Arg Arg Arg Arg
1               5                   10                  15

Arg Arg Arg Phe Phe Cys
            20

<210> SEQ ID NO 127
<211> LENGTH: 20
<212> TYPE: PRT
<213> ORGANISM: Artificial sequence
<220> FEATURE:
<223> OTHER INFORMATION: Synthetic sequence: Disulfide conjugate of
      CKPNA705K
<220> FEATURE:
<221> NAME/KEY: SITE
<222> LOCATION: (4)..(4)
<223> OTHER INFORMATION: Xaa is aminohexyl
<220> FEATURE:
<221> NAME/KEY: SITE
<222> LOCATION: (16)..(16)

-continued

<223> OTHER INFORMATION: Xaa is aminohexyl

<400> SEQUENCE: 127

His His His Xaa Arg Arg Arg Arg Arg Arg Arg Arg Phe Phe Xaa
1               5                   10                  15

His His His Cys
            20

<210> SEQ ID NO 128
<211> LENGTH: 18
<212> TYPE: DNA
<213> ORGANISM: Artificial sequence
<220> FEATURE:
<223> OTHER INFORMATION: Synthetic sequence: PNA705

<400> SEQUENCE: 128
cctcttacct cagttaca                                         18

<210> SEQ ID NO 129
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 129
cagaattctg ccaattgctg ag                                    22

<210> SEQ ID NO 130
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 130
ttcttcagct tgtgtcatcc                                       20

<210> SEQ ID NO 131
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 131
cccagtctac caccctatca gagc                                  24

<210> SEQ ID NO 132
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 132
cctgccttta aggcttcctt                                       20

<210> SEQ ID NO 133
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 133

-continued ttgatatgtg gatttcgagt cgtc                                            24

<210> SEQ ID NO 134
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 134
tgtcaatcag agtgcttttg gcg                                             23

<210> SEQ ID NO 135
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 135

Ile Lys Ile Leu Ile Gln Asn
1               5

<210> SEQ ID NO 136
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 136

Ile Lys Ile Leu Ile Gln Tyr
1               5

<210> SEQ ID NO 137
<211> LENGTH: 7
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (2)..(2)
<223> OTHER INFORMATION: Xaa is D-Lys

<400> SEQUENCE: 137

Ile Xaa Ile Leu Ile Gln Asn
1               5

<210> SEQ ID NO 138
<211> LENGTH: 7
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (2)..(2)
<223> OTHER INFORMATION: Xaa is D-Lys

<400> SEQUENCE: 138

Ile Xaa Ile Leu Ile Gln Tyr
1               5

<210> SEQ ID NO 139
<211> LENGTH: 7
<212> TYPE: PRT
<213> ORGANISM: Artificial sequence
<220> FEATURE:

<223> OTHER INFORMATION: Synthetic sequence: Domain 2 sequence

<400> SEQUENCE: 139

Ile His Ile Leu Ile Gln Asn
1               5

<210> SEQ ID NO 140
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 140

Ile His Ile Leu Ile Gln Tyr
1               5

<210> SEQ ID NO 141
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 141

Ile Arg Ile Leu Ile Gln Asn
1               5

<210> SEQ ID NO 142
<211> LENGTH: 7
<212> TYPE: PRT
<213> ORGANISM: Artificial sequence
<220> FEATURE:
<223> OTHER INFORMATION: Synthetic sequence: Domain 2 sequence

<400> SEQUENCE: 142

Ile Arg Ile Leu Ile Gln Tyr
1               5

<210> SEQ ID NO 143
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 143

Ile Ile Leu Ile Gln Asn
1               5

<210> SEQ ID NO 144
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 144

Ile Ile Leu Ile Gln Tyr
1               5

<210> SEQ ID NO 145
<211> LENGTH: 6
<212> TYPE: PRT
<213> ORGANISM: Artificial sequence
<220> FEATURE:
<223> OTHER INFORMATION: Synthetic sequence: Domain 2 sequence

```
<400> SEQUENCE: 145

Lys Ile Leu Ile Gln Asn
1               5

<210> SEQ ID NO 146
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 146

Lys Ile Leu Ile Gln Tyr
1               5

<210> SEQ ID NO 147
<211> LENGTH: 6
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (1)
<223> OTHER INFORMATION: Xaa is D-Lys

<400> SEQUENCE: 147

Xaa Ile Leu Ile Gln Asn
1               5

<210> SEQ ID NO 148
<211> LENGTH: 6
<212> TYPE: PRT
<213> ORGANISM: Artificial sequence
<220> FEATURE:
<223> OTHER INFORMATION: Synthetic sequence: Domain 2 sequence
<220> FEATURE:
<221> NAME/KEY: SITE
<222> LOCATION: (1)
<223> OTHER INFORMATION: Xaa is D-Lys

<400> SEQUENCE: 148

Xaa Ile Leu Ile Gln Tyr
1               5

<210> SEQ ID NO 149
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 149

His Ile Leu Ile Gln Asn
1               5

<210> SEQ ID NO 150
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 150

His Ile Leu Ile Gln Tyr
1               5

<210> SEQ ID NO 151
```

```
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 151

Arg Ile Leu Ile Gln Asn
1               5

<210> SEQ ID NO 152
<211> LENGTH: 6
<212> TYPE: PRT
<213> ORGANISM: Artificial sequence
<220> FEATURE:
<223> OTHER INFORMATION: Synthetic sequence: Domain 2 sequence

<400> SEQUENCE: 152

Arg Ile Leu Ile Gln Tyr
1               5

<210> SEQ ID NO 153
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 153

Ile Leu Ile Gln Asn
1               5

<210> SEQ ID NO 154
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 154

Ile Leu Ile Gln Tyr
1               5

<210> SEQ ID NO 155
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: SITE
<222> LOCATION: (1)..(1)
<223> OTHER INFORMATION: Xaa is D-Arg

<400> SEQUENCE: 155

Xaa His Met Lys Trp His Lys
1               5

<210> SEQ ID NO 156
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: SITE
<222> LOCATION: (1)..(1)
<223> OTHER INFORMATION: Xaa is D-Lys

<400> SEQUENCE: 156
```

```
Xaa Arg Met Lys Trp His Lys
1               5

<210> SEQ ID NO 157
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: SITE
<222> LOCATION: (1)..(1)
<223> OTHER INFORMATION: Xaa is D-Arg

<400> SEQUENCE: 157

Xaa Arg Trp Lys Trp His Lys
1               5

<210> SEQ ID NO 158
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: SITE
<222> LOCATION: (1)..(1)
<223> OTHER INFORMATION: Xaa is D-Lys

<400> SEQUENCE: 158

Xaa His Trp Lys Trp His Lys
1               5

<210> SEQ ID NO 159
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (2, 6)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (4)..(4)
<223> OTHER INFORMATION: bAla

<400> SEQUENCE: 159

Arg Xaa Arg Ala Arg Xaa Arg
1               5

<210> SEQ ID NO 160
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (2, 4, 6)
<223> OTHER INFORMATION: Xaa is aminohexyl, beta-alanyl, p-aminobenzoyl,
      isonipecotyl, or Aib

<400> SEQUENCE: 160

Arg Xaa Arg Xaa Arg Xaa Arg
1               5

<210> SEQ ID NO 161
```

```
<211> LENGTH: 6
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (2, 5)
<223> OTHER INFORMATION: Xaa is aminohexyl, beta-alanyl, p-aminobenzoyl,
      isonipecotyl, or Aib

<400> SEQUENCE: 161

Arg Xaa Arg Arg Xaa Arg
1               5

<210> SEQ ID NO 162
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: MOD_RES
<222> LOCATION: (2)..(2)
<223> OTHER INFORMATION: bAla
<220> FEATURE:
<221> NAME/KEY: VARIANT
<222> LOCATION: (4)..(4)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (6)..(6)
<223> OTHER INFORMATION: bAla

<400> SEQUENCE: 162

Arg Ala Arg Xaa Arg Ala Arg
1               5

<210> SEQ ID NO 163
<211> LENGTH: 6
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (2, 6)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (4)..(4)
<223> OTHER INFORMATION: bAla

<400> SEQUENCE: 163

Arg Xaa Arg Ala Arg Xaa
1               5

<210> SEQ ID NO 164
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
```

```
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 164

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Met Lys Trp His Lys
            20                  25

<210> SEQ ID NO 165
<211> LENGTH: 26
```

```
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
```

```
<223> OTHER INFORMATION: Attached to Z6 linker

<400> SEQUENCE: 165

Xaa Xaa Xaa Xaa Xaa Xaa Xaa Xaa Xaa Xaa Xaa Xaa Xaa Xaa Ile Leu
1               5                   10                  15

Phe Gln Xaa Xaa Arg Trp Lys Trp His Lys
            20                  25

<210> SEQ ID NO 166
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
```

```
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 166

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Trp Lys Trp His Lys
            20                  25

<210> SEQ ID NO 167
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment,
      Xaa1 - 3 is absent and Xaa4-12 is (Arg - Ala - Arg)3 wherein Ala
      is bAla. In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
```

```
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21)..(21)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: VARIANT
<222> LOCATION: (25)..(25)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (26)..(26)
<223> OTHER INFORMATION: Attached to Z6 linker

<400> SEQUENCE: 167

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg
            20                  25

<210> SEQ ID NO 168
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
```

```
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 23, 25)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (26)..(26)
<223> OTHER INFORMATION: Attached to Z6 linker

<400> SEQUENCE: 168

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Xaa Arg Xaa Arg
            20                  25

<210> SEQ ID NO 169
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
```

```
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present,
      Xaa is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 24)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (26)..(26)
<223> OTHER INFORMATION: Attached to Z6 linker

<400> SEQUENCE: 169

Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Arg Xaa Arg
            20                  25

<210> SEQ ID NO 170
<211> LENGTH: 26
<212> TYPE: PRT
<213> ORGANISM: Artificial sequence
<220> FEATURE:
```

```
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala -
      Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: MOD_RES
<222> LOCATION: (21, 25)
<223> OTHER INFORMATION: bAla
<220> FEATURE:
<221> NAME/KEY: VARIANT
<222> LOCATION: (23)..(23)
<223> OTHER INFORMATION: Xaa is aminohexyl, beta-alanyl, p-aminobenzoyl,
      isonipecotyl, or Aib
<220> FEATURE:
```

```
<221> NAME/KEY: SITE
<222> LOCATION: (26)..(26)
<223> OTHER INFORMATION: Attached to Z6 linker

<400> SEQUENCE: 170

Xaa Xaa Xaa Xaa Xaa Xaa Xaa Xaa Xaa Xaa Xaa Xaa Xaa Xaa Ile Leu
1               5                   10                  15

Phe Gln Xaa Arg Ala Arg Xaa Arg Ala Arg
            20                  25

<210> SEQ ID NO 171
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and
      Xaa 7-12 is (Arg - Xaa - Arg)2 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
```

```
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: (26)..(26)
<223> OTHER INFORMATION: Attached to Z6 linker

<400> SEQUENCE: 171

Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg
            20                  25

<210> SEQ ID NO 172
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and
      Xaa 7-12 is (Arg - Xaa - Arg)2 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
```

```
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: (26)..(26)
<223> OTHER INFORMATION: Attached to Z6 linker

<400> SEQUENCE: 172

Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa
            20                  25

<210> SEQ ID NO 173
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and
      Xaa 7-12 is (Arg - Xaa - Arg)2 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
```

```
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 173

Xaa Xaa Xaa Xaa Xaa Xaa Xaa Xaa Xaa Xaa Xaa Xaa Xaa Ile Leu
1               5                   10                  15

Ile Gln Xaa Xaa Arg Met Lys Trp His Lys
            20                  25

<210> SEQ ID NO 174
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
```

```
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa -  Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 174

Xaa Xaa Xaa Xaa Xaa Xaa Xaa Xaa Xaa Xaa Xaa Xaa Xaa Ile Leu
1               5                   10                  15

Ile Gln Xaa Xaa His Met Lys Trp His Lys
            20                  25

<210> SEQ ID NO 175
<211> LENGTH: 26
<212> TYPE: PRT
<213> ORGANISM: Artificial sequence
<220> FEATURE:
```

```
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 175
```

Xaa Xaa Xaa Xaa Xaa Xaa Xaa Xaa Xaa Xaa Xaa Xaa Xaa Ile Leu
1               5                   10                  15

Ile Gln Xaa Xaa Arg Trp Lys Trp His Lys
            20                  25

<210> SEQ ID NO 176
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:

```
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys
<220> FEATURE:
<221> NAME/KEY: SITE
<222> LOCATION: (26)..(26)
<223> OTHER INFORMATION: Attached to Z6 linker

<400> SEQUENCE: 176

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Trp Lys Trp His Lys
            20                  25

<210> SEQ ID NO 177
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa -
      Arg - Arg - Ala - Arg - Arg - Xaa - Arg (SEQ ID NO: 81) wherein
      Xaa is aminohexyl, beta-alanyl, p-aminobenzoyl, isonipecotyl, or
      Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and Xaa4 -
```

```
                12 is Arg - Ala - Arg - Arg - Xaa - Arg - Arg - Ala - Arg (SEQ ID
                NO: 82) wherein Xaa is aminohexyl, beta-alanyl, p-aminobenzoyl,
                isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
                is Ile.
<220> FEATURE:
<221> NAME/KEY: VARIANT
<222> LOCATION: (14)..(14)
<223> OTHER INFORMATION: Xaa may be present or absent. If present, Xaa
                is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
                isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: (26)..(26)
<223> OTHER INFORMATION: Attached to Z6 linker

<400> SEQUENCE: 177

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg
            20                  25

<210> SEQ ID NO 178
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
                Arg)4 wherein Xaa is aminohexyl, beta-alanyl, p-aminobenzoyl,
                isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
                Xaa 4-12 is (Arg - Xaa - Arg)3 wherein Xaa is aminohexyl,
                beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
                7-12 is (Arg - Xaa - Arg)2 wherein Xaa is aminohexyl, beta-alanyl,
                p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is (Arg - Ala -
                Arg)4 wherein Ala is bAla. In an embodiment, Xaa1 - 3 is absent
                and Xaa4-12 is (Arg - Ala - Arg)3 wherein Ala is bAla. In an
                embodiment, Xaa1 - 6 is absent and Xaa7-12 is (Arg - Ala - Arg)2
                wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
                Xaa5 - 12 is (Arg)8. In an embodiment, Xaa1 - 5 is absent and
                Xaa6 - 12 is (Arg)7. In an embodiment, Xaa1 - 6 is absent and
                Xaa7 - 12 is (Arg)6. In an embodiment, Xaa1 - 7 is absent and
                Xaa8 - 12 is (Arg)5.
```

```
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 23, 25)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (26)..(26)
<223> OTHER INFORMATION: Attached to Z6 linker

<400> SEQUENCE: 178

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Xaa Arg Xaa Arg
            20                  25

<210> SEQ ID NO 179
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is (Arg - Xaa -
      Arg)4 wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
```

```
<222> LOCATION: (1)..(12)
<223> OTHER INFORMATION: In an embodiment, Xaa1 - 12 is (Arg - Ala -
      Arg)4 wherein Ala is bAla. In an embodiment, Xaa1 - 3 is absent
      and Xaa4-12 is (Arg - Ala - Arg)3 wherein Ala is bAla. In an
      embodiment, Xaa1 - 6 is absent and Xaa7-12 is (Arg - Ala - Arg)2
      wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg
      (SEQ ID NO: 80) wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 24)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: 25
<223> OTHER INFORMATION: Attached to Z6 linker

<400> SEQUENCE: 179

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Arg Xaa Arg
            20                  25

<210> SEQ ID NO 180
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
```

```
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: MOD_RES
<222> LOCATION: (21, 25)
<223> OTHER INFORMATION: bAla
<220> FEATURE:
<221> NAME/KEY: VARIANT
<222> LOCATION: (23)..(23)
<223> OTHER INFORMATION: Xaa is aminohexyl, beta-alanyl, p-aminobenzoyl,
      isonipecotyl, or Aib
<220> FEATURE:
<221> NAME/KEY: SITE
<222> LOCATION: (26)..(26)
<223> OTHER INFORMATION: Attached to Z6 linker

<400> SEQUENCE: 180

Xaa Xaa Xaa Xaa Xaa Xaa Xaa Xaa Xaa Xaa Xaa Xaa Xaa Xaa Ile Leu
```

```
                1               5                  10                15
Ile Gln Xaa Arg Ala Arg Xaa Arg Ala Arg
                20                  25

<210> SEQ ID NO 181
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
```

```
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: (26)..(26)
<223> OTHER INFORMATION: Attached to Z6 linker

<400> SEQUENCE: 181

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg
            20              25

<210> SEQ ID NO 182
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
```

```
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla
<220> FEATURE:
<221> NAME/KEY: SITE
<222> LOCATION: 25
<223> OTHER INFORMATION: Attached to Z6 linker

<400> SEQUENCE: 182

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa
            20                  25

<210> SEQ ID NO 183
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
```

```
        Xaa7 - 12 is (Arg)6. In an embodiment, Xaa1 - 7 is absent and
        Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
        Xaa5 - 12 is Arg - Xaa - Arg - Arg - Xaa - Arg - Ile - D-Arg (SEQ
        ID NO: 80) wherein Xaa is aminohexyl, beta-alanyl, p-aminobenzoyl,
        isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
        Xaa4 - 12 is Arg - Xaa - Arg - Arg - Ala - Arg - Xaa - Arg
        (SEQ ID NO: 81) wherein Xaa is aminohexyl, beta-alanyl,
        p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
        Xaa4 - 12 is Arg - Ala - Arg - Arg - Xaa - Arg - Ala - Arg
        (SEQ ID NO: 82) wherein Xaa is aminohexyl, beta-alanyl,
        p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
        is Ile.
<220> FEATURE:
<221> NAME/KEY: VARIANT
<222> LOCATION: (14)..(14)
<223> OTHER INFORMATION: Xaa may be present or absent. If present, Xaa
        is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 183

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Met Lys Trp His Lys
            20                  25

<210> SEQ ID NO 184
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
        (Arg - Xaa - Arg)4 wherein Xaa is aminohexyl, beta-alanyl,
        p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
        4-12 is (Arg - Xaa - Arg)3 wherein Xaa is aminohexyl, beta-alanyl,
        p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
        7-12 is (Arg - Xaa - Arg)2 wherein Xaa is aminohexyl, beta-alanyl,
        p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
        (Arg - Ala - Arg)4 wherein Ala is bAla. In an embodiment, Xaa1 - 3
```

```
              is absent and Xaa4-12 is (Arg - Ala - Arg)3 wherein Ala is bAla.
              In an embodiment, Xaa1 - 6 is absent and Xaa7-12 is
              (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
              Xaa5 - 12 is (Arg)8. In an embodiment, Xaa1 - 5 is absent and
              Xaa6 - 12 is (Arg)7. In an embodiment, Xaa1 - 6 is absent and
              Xaa7 - 12 is (Arg)6. In an embodiment, Xaa1 - 7 is absent and
              Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
              Xaa5 - 12 is Arg - Xaa - Arg - Arg - Xaa - Arg - Ile - D-Arg (SEQ
              ID NO: 80) wherein Xaa is aminohexyl, beta-alanyl, p-aminobenzoyl,
              isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
              Xaa4 - 12 is Arg - Xaa - Arg - Arg - Ala - Arg - Arg - Xaa - Arg
              (SEQ ID NO: 81) wherein Xaa is aminohexyl, beta-alanyl,
              p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
              Xaa4 - 12 is Arg - Ala - Arg - Arg - Xaa - Arg - Arg - Ala - Arg
              (SEQ ID NO: 82) wherein Xaa is aminohexyl, beta-alanyl,
              p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
              is Ile.
<220> FEATURE:
<221> NAME/KEY: VARIANT
<222> LOCATION: (14)..(14)
<223> OTHER INFORMATION: Xaa may be present or absent. If present, Xaa
              is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 184

Xaa Xaa Xaa Xaa Xaa Xaa Xaa Xaa Xaa Xaa Xaa Xaa Xaa Ile Leu
1               5                   10                  15

Phe Gln Xaa Xaa Arg Trp Lys Trp His Lys
            20                  25

<210> SEQ ID NO 185
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
              (Arg - Xaa - Arg)4 wherein Xaa is aminohexyl, beta-alanyl,
              p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
              4-12 is (Arg - Xaa - Arg)3 wherein Xaa is aminohexyl, beta-alanyl,
              p-aminobenzoyl, isonipecotyl, or Aib.
<220> FEATURE:
<221> NAME/KEY: VARIANT
```

```
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 185

Xaa Xaa Xaa Xaa Xaa Xaa Xaa Xaa Xaa Xaa Xaa Xaa Xaa Xaa Ile Leu
1               5                   10                  15

Phe Gln Xaa Xaa His Trp Lys Trp His Lys
            20                  25

<210> SEQ ID NO 186
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
```

```
                p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa 4-12 is (Arg - Xaa - Arg)3 wherein Xaa is aminohexyl,
      beta-alanyl, p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla

<400> SEQUENCE: 186

Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg
```

```
                    20                  25

<210> SEQ ID NO 187
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
```

-continued

```
<222> LOCATION: (21, 23, 25)
<223> OTHER INFORMATION: Xaa is aminohexyl, beta-alanyl, p-aminobenzoyl,
      isonipecotyl, or Aib

<400> SEQUENCE: 187

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Xaa Arg Xaa Arg
            20                  25

<210> SEQ ID NO 188
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
```

```
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 24)
<223> OTHER INFORMATION: Xaa is aminohexyl, beta-alanyl, p-aminobenzoyl,
      isonipecotyl, or Aib

<400> SEQUENCE: 188

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Arg Xaa Arg
            20                  25

<210> SEQ ID NO 189
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
```

```
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: MOD_RES
<222> LOCATION: (21, 25)
<223> OTHER INFORMATION: bAla
<220> FEATURE:
<221> NAME/KEY: VARIANT
<222> LOCATION: (23)..(23)
<223> OTHER INFORMATION: Xaa is aminohexyl, beta-alanyl, p-aminobenzoyl,
      isonipecotyl, or Aib

<400> SEQUENCE: 189

Xaa Xaa Xaa Xaa Xaa Xaa Xaa Xaa Xaa Xaa Xaa Xaa Xaa Xaa Ile Leu
1               5                   10                  15

Phe Gln Xaa Arg Ala Arg Xaa Arg Ala Arg
            20                  25

<210> SEQ ID NO 190
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
```

```
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla

<400> SEQUENCE: 190

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa Arg
            20                  25

<210> SEQ ID NO 191
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
```

```
             is absent and Xaa4-12 is (Arg - Ala - Arg)3 wherein Ala is bAla.
             In an embodiment, Xaa1 - 6 is absent and Xaa7-12 is
             (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
             Xaa5 - 12 is (Arg)8. In an embodiment, Xaa1 - 5 is absent and
             Xaa6 - 12 is (Arg)7. In an embodiment, Xaa1 - 6 is absent and
             Xaa7 - 12 is (Arg)6. In an embodiment, Xaa1 - 7 is absent and
             Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
             Xaa5 - 12 is Arg - Xaa - Arg - Arg - Xaa - Arg - Ile - D-Arg (SEQ
             ID NO: 80) wherein Xaa is aminohexyl, beta-alanyl, p-aminobenzoyl,
             isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
             Xaa4 - 12 is Arg - Xaa - Arg - Arg - Ala - Arg - Arg - Xaa - Arg
             (SEQ ID NO: 81) wherein Xaa is aminohexyl, beta-alanyl,
             p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
             Xaa4 - 12 is Arg - Ala - Arg - Arg - Xaa - Arg - Arg - Ala - Arg
             (SEQ ID NO: 82) wherein Xaa is aminohexyl, beta-alanyl,
             p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
             is Ile.
<220> FEATURE:
<221> NAME/KEY: VARIANT
<222> LOCATION: (14)..(14)
<223> OTHER INFORMATION: Xaa may be present or absent. If present, Xaa
             is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
             isonipecotyl, or Aib
<220> FEATURE:
<221> NAME/KEY: MOD_RES
<222> LOCATION: (23)..(23)
<223> OTHER INFORMATION: bAla

<400> SEQUENCE: 191

Xaa Xaa Xaa Xaa Xaa Xaa Xaa Xaa Xaa Xaa Xaa Xaa Xaa Xaa Ile Leu
1               5                   10                  15

Phe Gln Xaa Arg Xaa Arg Ala Arg Xaa
            20                  25

<210> SEQ ID NO 192
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
             (Arg - Xaa - Arg)4 wherein Xaa is aminohexyl, beta-alanyl,
             p-aminobenzoyl, isonipecotyl, or Aib.
<220> FEATURE:
<221> NAME/KEY: VARIANT
<222> LOCATION: (1)..(12)
```

```
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 192

Xaa Xaa Xaa Xaa Xaa Xaa Xaa Xaa Xaa Xaa Xaa Xaa Xaa Ile Leu
1               5                   10                  15

Ile Gln Xaa Xaa Arg Met Lys Trp His Lys
            20                  25

<210> SEQ ID NO 193
<211> LENGTH: 26
<212> TYPE: PRT
<213> ORGANISM: Artificial sequence
<220> FEATURE:
<223> OTHER INFORMATION: Synthetic peptide
```

```
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 193

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Met Lys Trp His Lys
```

```
                          20              25

<210> SEQ ID NO 194
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
```

```
<222> LOCATION: (20)..(20)
<223> OTHER INFORMATION: Xaa is Arg or D-Arg, Lys or D-Lys

<400> SEQUENCE: 194

Xaa Xaa Xaa Xaa Xaa Xaa Xaa Xaa Xaa Xaa Xaa Xaa Xaa Xaa Ile Leu
1               5                   10                  15

Ile Gln Xaa Xaa Arg Trp Lys Trp His Lys
            20                  25

<210> SEQ ID NO 195
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
```

```
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (20)..(20)
<223> OTHER INFORMATION: Xaa is Arg or D-Arg, Lys or D-Lys

<400> SEQUENCE: 195

Xaa Xaa Xaa Xaa Xaa Xaa Xaa Xaa Xaa Xaa Xaa Xaa Xaa Xaa Ile Leu
1               5                   10                  15

Ile Gln Xaa Xaa His Trp Lys Trp His Lys
            20                  25

<210> SEQ ID NO 196
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
```

```
                         (SEQ ID NO: 82) wherein Xaa is aminohexyl, beta-alanyl,
                         p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
                         is Ile.
<220> FEATURE:
<221> NAME/KEY: VARIANT
<222> LOCATION: (14)..(14)
<223> OTHER INFORMATION: Xaa may be present or absent. If present, Xaa
                         is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
                         isonipecotyl, or Aib
<220> FEATURE:
<221> NAME/KEY: MOD_RES
<222> LOCATION: (23)..(23)
<223> OTHER INFORMATION: bAla

<400> SEQUENCE: 196

Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg
            20                  25

<210> SEQ ID NO 197
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
                         (Arg - Xaa - Arg)4 wherein Xaa is aminohexyl, beta-alanyl,
                         p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
                         4-12 is (Arg - Xaa - Arg)3 wherein Xaa is aminohexyl, beta-alanyl,
                         p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
                         7-12 is (Arg - Xaa - Arg)2 wherein Xaa is aminohexyl, beta-alanyl,
                         p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
                         (Arg - Ala - Arg)4 wherein Ala is bAla. In an embodiment, Xaa1 - 3
                         is absent and Xaa4-12 is (Arg - Ala - Arg)3 wherein Ala is bAla.
                         In an embodiment, Xaa1 - 6 is absent and Xaa7-12 is
                         (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
                         Xaa5 - 12 is (Arg)8. In an embodiment, Xaa1 - 5 is absent and
                         Xaa6 - 12 is (Arg)7. In an embodiment, Xaa1 - 6 is absent and
                         Xaa7 - 12 is (Arg)6. In an embodiment, Xaa1 - 7 is absent and
                         Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
                         Xaa5 - 12 is Arg - Xaa - Arg - Arg - Xaa - Arg - Ile - D-Arg (SEQ
```

```
           ID NO: 80) wherein Xaa is aminohexyl, beta-alanyl, p-aminobenzoyl,
           isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
           Xaa4 - 12 is Arg - Xaa - Arg - Arg - Ala - Arg - Arg - Xaa - Arg
           (SEQ ID NO: 81) wherein Xaa is aminohexyl, beta-alanyl,
           p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
           Xaa4 - 12 is Arg - Ala - Arg - Arg - Xaa - Arg - Arg - Ala - Arg
           (SEQ ID NO: 82) wherein Xaa is aminohexyl, beta-alanyl,
           p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
           is Ile.
<220> FEATURE:
<221> NAME/KEY: VARIANT
<222> LOCATION: (14)..(14)
<223> OTHER INFORMATION: Xaa may be present or absent. If present, Xaa
           is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 23, 25)
<223> OTHER INFORMATION: Xaa is aminohexyl, beta-alanyl, p-aminobenzoyl,
           isonipecotyl, or Aib

<400> SEQUENCE: 197

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Xaa Arg Xaa Arg
            20                  25

<210> SEQ ID NO 198
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
           (Arg - Xaa - Arg)4 wherein Xaa is aminohexyl, beta-alanyl,
           p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
           4-12 is (Arg - Xaa - Arg)3 wherein Xaa is aminohexyl, beta-alanyl,
           p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
           7-12 is (Arg - Xaa - Arg)2 wherein Xaa is aminohexyl, beta-alanyl,
           p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
           (Arg - Ala - Arg)4 wherein Ala is bAla. In an embodiment, Xaa1 - 3
           is absent and Xaa4-12 is (Arg - Ala - Arg)3 wherein Ala is bAla.
           In an embodiment, Xaa1 - 6 is absent and Xaa7-12 is
           (Arg - Ala - Arg)2 wherein Ala is bAla.
<220> FEATURE:
<221> NAME/KEY: VARIANT
<222> LOCATION: (1)..(12)
```

```
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 24)
<223> OTHER INFORMATION: Xaa is aminohexyl, beta-alanyl, p-aminobenzoyl,
      isonipecotyl, or Aib

<400> SEQUENCE: 198

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Arg Xaa Arg
            20                  25

<210> SEQ ID NO 199
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
```

```
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla.
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: MOD_RES
<222> LOCATION: (21)..(21)
<223> OTHER INFORMATION: bAla
<220> FEATURE:
<221> NAME/KEY: VARIANT
<222> LOCATION: (23)..(23)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (25)..(25)
<223> OTHER INFORMATION: bAla

<400> SEQUENCE: 199

Xaa Xaa Xaa Xaa Xaa Xaa Xaa Xaa Xaa Xaa Xaa Xaa Xaa Ile Leu
1               5                   10                  15

Ile Gln Xaa Arg Ala Arg Xaa Arg Ala Arg
            20                  25

<210> SEQ ID NO 200
<211> LENGTH: 26
<212> TYPE: PRT
<213> ORGANISM: Artificial sequence
<220> FEATURE:
<223> OTHER INFORMATION: Synthetic peptide
<220> FEATURE:
```

```
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla

<400> SEQUENCE: 200
```

```
Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa Arg
            20                  25

<210> SEQ ID NO 201
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(12)
<223> OTHER INFORMATION: In an embodiment, Xaa1 - 12 is
      (Arg - Xaa - Arg)4 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and Xaa
      4-12 is (Arg - Xaa - Arg)3 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 6 is absent and Xaa
      7-12 is (Arg - Xaa - Arg)2 wherein Xaa is aminohexyl, beta-alanyl,
      p-aminobenzoyl, isonipecotyl, or Aib.
<220> FEATURE:
<221> NAME/KEY: VARIANT
<222> LOCATION: (1)..(12)
<223> OTHER INFORMATION: In an embodiment, Xaa1 - 12 is
      (Arg - Ala - Arg)4 wherein Ala is bAla. In an embodiment, Xaa1 - 3
      is absent and Xaa4-12 is (Arg - Ala - Arg)3 wherein Ala is bAla.
      In an embodiment, Xaa1 - 6 is absent and Xaa7-12 is
      (Arg - Ala - Arg)2 wherein Ala is bAla.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is (Arg)8. In an embodiment, Xaa1 - 5 is absent and
      Xaa6 - 12 is (Arg)7. In an embodiment, Xaa1 - 6 is absent and
      Xaa7 - 12 is (Arg)6. In an embodiment, Xaa1 - 7 is absent and
      Xaa8 - 12 is (Arg)5.
<220> FEATURE:
<221> NAME/KEY: VARIANT
<222> LOCATION: (1)..(12)
<223> OTHER INFORMATION: In an embodiment, Xaa1 - 4 is absent and
      Xaa5 - 12 is Arg - Xaa - Arg - Arg - Xaa - Arg - Ile - D-Arg (SEQ
      ID NO: 80) wherein Xaa is aminohexyl, beta-alanyl, p-aminobenzoyl,
      isonipecotyl, or Aib.
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Xaa - Arg - Arg - Ala - Arg - Arg - Xaa - Arg
      (SEQ ID NO: 81) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (1)..(12)
<223> OTHER INFORMATION: In an embodiment, Xaa1 - 3 is absent and
      Xaa4 - 12 is Arg - Ala - Arg - Arg - Xaa - Arg - Arg - Ala - Arg
      (SEQ ID NO: 82) wherein Xaa is aminohexyl, beta-alanyl,
      p-aminobenzoyl, isonipecotyl, or Aib and Ala is bAla
<220> FEATURE:
<221> NAME/KEY: VARIANT
<222> LOCATION: (13)..(13)
<223> OTHER INFORMATION: Xaa may be present or absent. If present, Xaa
      is Ile.
<220> FEATURE:
<221> NAME/KEY: VARIANT
<222> LOCATION: (14)..(14)
<223> OTHER INFORMATION: Xaa may be present or absent. If present, Xaa
      is Lys, D-Lys, His, or Arg
<220> FEATURE:
<221> NAME/KEY: VARIANT
```

```
<222> LOCATION: (19)..(19)
<223> OTHER INFORMATION: Xaa is Asn or Tyr
<220> FEATURE:
<221> NAME/KEY: VARIANT
<222> LOCATION: (21, 25)
<223> OTHER INFORMATION: Xaa is aminohexyl, beta-alanyl, p-aminobenzoyl,
      isonipecotyl, or Aib
<220> FEATURE:
<221> NAME/KEY: MOD_RES
<222> LOCATION: (23)..(23)
<223> OTHER INFORMATION: bAla

<400> SEQUENCE: 201

Xaa Xaa Xaa Xaa Xaa Xaa Xaa Xaa Xaa Xaa Xaa Xaa Xaa Xaa Ile Leu
1               5                   10                  15

Ile Gln Xaa Arg Xaa Arg Ala Arg Xaa
            20                  25

<210> SEQ ID NO 202
<211> LENGTH: 4
<212> TYPE: PRT
<213> ORGANISM: Artificial sequence
<220> FEATURE:
<223> OTHER INFORMATION: Synthetic sequence: Domain 2 sequence

<400> SEQUENCE: 202

Ile Leu Ile Gln
1

<210> SEQ ID NO 203
<211> LENGTH: 5
<212> TYPE: PRT
<213> ORGANISM: Artificial sequence
<220> FEATURE:
<223> OTHER INFORMATION: Synthetic sequence: Domain 3 sequence

<400> SEQUENCE: 203

Met Lys Trp His Lys
1               5

<210> SEQ ID NO 204
<211> LENGTH: 5
<212> TYPE: PRT
<213> ORGANISM: Artificial sequence
<220> FEATURE:
<223> OTHER INFORMATION: Synthetic sequence: Domain 3 sequence

<400> SEQUENCE: 204

Trp Lys Trp His Lys
1               5

<210> SEQ ID NO 205

<400> SEQUENCE: 205

000

<210> SEQ ID NO 206
<211> LENGTH: 25
<212> TYPE: DNA
<213> ORGANISM: Artificial sequence
<220> FEATURE:
<223> OTHER INFORMATION: Synthetic sequence: PMODMD

<400> SEQUENCE: 206
ggccaaacct cggcttacct gaaat                                       25

<210> SEQ ID NO 207
```

```
<211> LENGTH: 14
<212> TYPE: PRT
<213> ORGANISM: Artificial sequence
<220> FEATURE:
<223> OTHER INFORMATION: Synthetic sequence: B peptide
<220> FEATURE:
<221> NAME/KEY: SITE
<222> LOCATION: 2, 8, 13
<223> OTHER INFORMATION: Xaa is aminohexyl
<220> FEATURE:
<221> NAME/KEY: MOD_RES
<222> LOCATION: (5, 11, 14)
<223> OTHER INFORMATION: bAla

<400> SEQUENCE: 207

Arg Xaa Arg Arg Ala Arg Arg Xaa Arg Arg Ala Arg Xaa Ala
1               5                   10

<210> SEQ ID NO 208
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: 15
<223> OTHER INFORMATION: Xaa is D-Arg
<220> FEATURE:
<221> NAME/KEY: SITE
<222> LOCATION: 23
<223> OTHER INFORMATION: Disulfide linked to Cys-Lys-PNA705-Lys

<400> SEQUENCE: 208

Arg Xaa Arg Arg Ala Arg Arg Xaa Arg Ile Leu Phe Gln Tyr Xaa His
1               5                   10                  15

Met Lys Trp His Lys Ala Cys
            20

<210> SEQ ID NO 209
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: 15
<223> OTHER INFORMATION: Xaa is D-Lys
<220> FEATURE:
<221> NAME/KEY: SITE
<222> LOCATION: 23
<223> OTHER INFORMATION: Disulfide linked to Cys-Lys-PNA705-Lys

<400> SEQUENCE: 209

Arg Xaa Arg Arg Ala Arg Arg Xaa Arg Ile Leu Phe Gln Tyr Xaa Arg
1               5                   10                  15
```

Met Lys Trp His Lys Ala Cys
            20

<210> SEQ ID NO 210
<211> LENGTH: 23
<212> TYPE: PRT
<213> ORGANISM: Artificial sequence
<220> FEATURE:
<223> OTHER INFORMATION: Synthetic sequence: Peptide conjugate
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: 15
<223> OTHER INFORMATION: Xaa is D-Arg
<220> FEATURE:
<221> NAME/KEY: SITE
<222> LOCATION: 23
<223> OTHER INFORMATION: Disulfide linked to Cys-Lys-PNA705-Lys

<400> SEQUENCE: 210

Arg Xaa Arg Arg Ala Arg Arg Xaa Arg Ile Leu Phe Gln Tyr Xaa Arg
1               5                   10                  15

Trp Lys Trp His Lys Ala Cys
            20

<210> SEQ ID NO 211
<211> LENGTH: 13
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8, 11)
<223> OTHER INFORMATION: Xaa is aminohexyl
<220> FEATURE:
<221> NAME/KEY: SITE
<222> LOCATION: 13
<223> OTHER INFORMATION: Thioether linked to CH2-CO-K-PNADMD-K

<400> SEQUENCE: 211

Arg Xaa Arg Arg Xaa Arg Arg Xaa Arg Arg Xaa Arg Cys
1               5                   10

<210> SEQ ID NO 212
<211> LENGTH: 25
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24

```
<223> OTHER INFORMATION: bAla
<220> FEATURE:
<221> NAME/KEY: SITE
<222> LOCATION: 25
<223> OTHER INFORMATION: Thioether linked to CH2-CO-K-PNADMD-K

<400> SEQUENCE: 212

Arg Xaa Arg Arg Xaa Arg Arg Xaa Arg Ile Xaa Ile Leu Phe Gln Asn
1               5                   10                  15

Xaa Arg Met Lys Trp His Lys Ala Cys
            20                  25

<210> SEQ ID NO 213
<211> LENGTH: 25
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Thioether linked to CH2-CO-K-PNADMD-K

<400> SEQUENCE: 213

Arg Xaa Arg Arg Xaa Arg Arg Xaa Arg Ile His Ile Leu Phe Gln Asn
1               5                   10                  15

Xaa Arg Met Lys Trp His Lys Ala Cys
            20                  25

<210> SEQ ID NO 214
<211> LENGTH: 25
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (11)..(11)
<223> OTHER INFORMATION: Xaa is D-Lys
<220> FEATURE:
<221> NAME/KEY: SITE
<222> LOCATION: (17)..(17)
<223> OTHER INFORMATION: Xaa is D-Arg
<220> FEATURE:
<221> NAME/KEY: MOD_RES
<222> LOCATION: 24
<223> OTHER INFORMATION: bAla
<220> FEATURE:
<221> NAME/KEY: SITE
<222> LOCATION: 25
<223> OTHER INFORMATION: Thioether linked to CH2-CO-K-PNADMD-K

<400> SEQUENCE: 214

Arg Xaa Arg Arg Xaa Arg Arg Xaa Arg Ile Xaa Ile Leu Phe Gln Tyr
1               5                   10                  15
```

Xaa Arg Met Lys Trp His Lys Ala Cys
            20                  25

<210> SEQ ID NO 215
<211> LENGTH: 26
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: (18)
<223> OTHER INFORMATION: Xaa is D-Arg
<220> FEATURE:
<221> NAME/KEY: MOD_RES
<222> LOCATION: 25
<223> OTHER INFORMATION: bAla
<220> FEATURE:
<221> NAME/KEY: SITE
<222> LOCATION: 26
<223> OTHER INFORMATION: Thioether linked to CH2-CO-K-PNADMD-K

<400> SEQUENCE: 215

Arg Xaa Arg Arg Xaa Arg Arg Xaa Arg Leu Tyr Ser Pro Leu Ser Phe
1               5                   10                  15

Gln Xaa Arg Met Lys Trp His Lys Ala Cys
            20                  25

<210> SEQ ID NO 216
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 5, 8)
<223> OTHER INFORMATION: Xaa is aminohexyl
<220> FEATURE:
<221> NAME/KEY: SITE
<222> LOCATION: 15
<223> OTHER INFORMATION: Xaa is D-Arg
<220> FEATURE:
<221> NAME/KEY: MOD_RES
<222> LOCATION: (22)
<223> OTHER INFORMATION: bAla
<220> FEATURE:
<221> NAME/KEY: SITE
<222> LOCATION: 23
<223> OTHER INFORMATION: Thioether linked to CH2-CO-K-PNADMD-K

<400> SEQUENCE: 216

Arg Xaa Arg Arg Xaa Arg Arg Xaa Arg Ile Leu Phe Gln Tyr Xaa Arg
1               5                   10                  15

Met Lys Trp His Lys Ala Cys
            20

<210> SEQ ID NO 217
<211> LENGTH: 22
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE

```
<222> LOCATION: (2, 5)
<223> OTHER INFORMATION: Xaa is aminohexyl
<220> FEATURE:
<221> NAME/KEY: SITE
<222> LOCATION: 8, 14
<223> OTHER INFORMATION: Xaa is D-Arg
<220> FEATURE:
<221> NAME/KEY: MOD_RES
<222> LOCATION: 21
<223> OTHER INFORMATION: bAla
<220> FEATURE:
<221> NAME/KEY: SITE
<222> LOCATION: 22
<223> OTHER INFORMATION: Thioether linked to CH2-CO-K-PNADMD-K

<400> SEQUENCE: 217

Arg Xaa Arg Arg Xaa Arg Ile Xaa Ile Leu Phe Gln Tyr Xaa Arg Met
1               5                   10                  15

Lys Trp His Lys Ala Cys
            20

<210> SEQ ID NO 218
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: MOD_RES
<222> LOCATION: 2, 8, 22
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: 15
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 218

Arg Ala Arg Arg Xaa Arg Arg Ala Arg Ile Leu Phe Gln Tyr Xaa Arg
1               5                   10                  15

Met Lys Trp His Lys Ala Cys
            20

<210> SEQ ID NO 219
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K
```

-continued

<400> SEQUENCE: 219

Arg Xaa Arg Arg Ala Arg Arg Xaa Arg Ile Leu Phe Gln Tyr Xaa Arg
1               5                   10                  15

Met Lys Trp His Lys Ala Cys
            20

<210> SEQ ID NO 220
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: MOD_RES
<222> LOCATION: 2, 8, 22
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: 15
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 220

Arg Ala Arg Arg Xaa Arg Arg Ala Arg Ile Leu Phe Gln Tyr Xaa Arg
1               5                   10                  15

Met Lys Trp His Lys Ala Cys
            20

<210> SEQ ID NO 221
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 221

Arg Xaa Arg Arg Ala Arg Arg Xaa Arg Ile Leu Phe Gln Tyr Xaa Arg
1               5                   10                  15

Met Lys Trp His Lys Ala Cys
            20

<210> SEQ ID NO 222
<211> LENGTH: 23
<212> TYPE: PRT
<213> ORGANISM: Artificial sequence

```
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 222

Arg Xaa Arg Arg Ala Arg Arg Xaa Arg Ile Leu Phe Gln Tyr Xaa His
 1               5                  10                  15

Met Lys Trp His Lys Ala Cys
             20

<210> SEQ ID NO 223
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
<223> OTHER INFORMATION: Xaa is D-Lys
<220> FEATURE:
<221> NAME/KEY: SITE
<222> LOCATION: 23
<223> OTHER INFORMATION: Thioether linked to CH2-CO-K-PNADMD-K

<400> SEQUENCE: 223

Arg Xaa Arg Arg Ala Arg Arg Xaa Arg Ile Leu Phe Gln Tyr Xaa Arg
 1               5                  10                  15

Met Lys Trp His Lys Ala Cys
             20

<210> SEQ ID NO 224
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
```

```
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 224

Arg Xaa Arg Arg Ala Arg Arg Xaa Arg Ile Leu Phe Gln Tyr Xaa Arg
1               5                   10                  15

Trp Lys Trp His Lys Ala Cys
            20

<210> SEQ ID NO 225
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
<223> OTHER INFORMATION: Xaa is D-Lys
<220> FEATURE:
<221> NAME/KEY: SITE
<222> LOCATION: 23
<223> OTHER INFORMATION: Thioether linked to CH2-CO-K-PNADMD-K

<400> SEQUENCE: 225

Arg Xaa Arg Arg Ala Arg Arg Xaa Arg Ile Leu Phe Gln Tyr Xaa His
1               5                   10                  15

Trp Lys Trp His Lys Ala Cys
            20

<210> SEQ ID NO 226
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: 2, 8, 16, 20
<223> OTHER INFORMATION: Xaa is aminohexyl
<220> FEATURE:
<221> NAME/KEY: MOD_RES
<222> LOCATION: 5, 18, 22
<223> OTHER INFORMATION: bAla
<220> FEATURE:
<221> NAME/KEY: SITE
<222> LOCATION: 23
<223> OTHER INFORMATION: Thioether linked to CH2-CO-K-PNADMD-K

<400> SEQUENCE: 226

Arg Xaa Arg Arg Ala Arg Arg Xaa Arg Ile Leu Phe Gln Tyr Arg Xaa
1               5                   10                  15

Arg Ala Arg Xaa Arg Ala Cys
            20

<210> SEQ ID NO 227
<211> LENGTH: 23
<212> TYPE: PRT
```

```
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: 2, 8, 16, 18, 20
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: 23
<223> OTHER INFORMATION: Thioether linked to CH2-CO-K-PNADMD-K

<400> SEQUENCE: 227

Arg Xaa Arg Arg Ala Arg Arg Xaa Arg Ile Leu Phe Gln Tyr Arg Xaa
1               5                   10                  15

Arg Xaa Arg Xaa Arg Ala Cys
            20

<210> SEQ ID NO 228
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: (2, 8)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (15)..(15)
<223> OTHER INFORMATION: Xaa is D-Arg
<220> FEATURE:
<221> NAME/KEY: SITE
<222> LOCATION: 23
<223> OTHER INFORMATION: Thioether linked to CH2-CO-K-PNADMD-K

<400> SEQUENCE: 228

Arg Xaa Arg Arg Ala Arg Arg Xaa Arg Ile Leu Ile Gln Tyr Xaa Arg
1               5                   10                  15

Met Lys Trp His Lys Ala Cys
            20

<210> SEQ ID NO 229
<211> LENGTH: 18
<212> TYPE: PRT
<213> ORGANISM: Artificial sequence
<220> FEATURE:
<223> OTHER INFORMATION: Synthetic sequence: Pip peptide conjugated to
      PNADMD cargo
<220> FEATURE:
<221> NAME/KEY: SITE
<222> LOCATION: 2, 5, 13, 16
<223> OTHER INFORMATION: Xaa is aminohexyl
<220> FEATURE:
<221> NAME/KEY: SITE
<222> LOCATION: 18
<223> OTHER INFORMATION: Thioether linked to CH2-CO-K-PNADMD-K

<400> SEQUENCE: 229

Arg Xaa Arg Arg Xaa Arg Ile Leu Phe Gln Tyr Arg Xaa Arg Arg Xaa
1               5                   10                  15
```

Arg Cys

```
<210> SEQ ID NO 230
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5, 18, 22
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl
<220> FEATURE:
<221> NAME/KEY: SITE
<222> LOCATION: 23
<223> OTHER INFORMATION: Thioether linked to PMODMD

<400> SEQUENCE: 230

Arg Xaa Arg Arg Ala Arg Arg Xaa Arg Ile Leu Phe Gln Tyr Arg Xaa
1               5                   10                  15

Arg Ala Arg Xaa Arg Ala Cys
            20

<210> SEQ ID NO 231
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl
<220> FEATURE:
<221> NAME/KEY: SITE
<222> LOCATION: 23
<223> OTHER INFORMATION: Thioether linked to PMODMD
```

-continued

```
<400> SEQUENCE: 231

Arg Xaa Arg Arg Ala Arg Arg Xaa Arg Ile Leu Phe Gln Tyr Arg Xaa
1               5                   10                  15

Arg Xaa Arg Xaa Arg Ala Cys
            20

<210> SEQ ID NO 232
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5, 22
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Arg
<220> FEATURE:
<221> NAME/KEY: SITE
<222> LOCATION: 23
<223> OTHER INFORMATION: Thioether linked to PMODMD

<400> SEQUENCE: 232

Arg Xaa Arg Arg Ala Arg Arg Xaa Arg Ile Leu Ile Gln Tyr Xaa Arg
1               5                   10                  15

Met Lys Trp His Lys Ala Cys
            20

<210> SEQ ID NO 233
<211> LENGTH: 20
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: 20
<223> OTHER INFORMATION: Thioether linked to PMODMD

<400> SEQUENCE: 233

Arg Xaa Arg Arg Xaa Arg Ile Leu Phe Gln Tyr Arg Xaa Arg Arg Xaa
1               5                   10                  15

Arg Cys Tyr Ser
```

<210> SEQ ID NO 234
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: MOD_RES
<222> LOCATION: 2, 8, 16, 20, 22
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: 23
<223> OTHER INFORMATION: Thioether linked to PMODMD

<400> SEQUENCE: 234

Arg Ala Arg Arg Xaa Arg Arg Ala Arg Ile Leu Phe Gln Tyr Arg Ala
1               5                   10                  15

Arg Xaa Arg Ala Arg Ala Cys
            20

<210> SEQ ID NO 235
<211> LENGTH: 23
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: MOD_RES
<222> LOCATION: 2, 8, 18, 22
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl
<220> FEATURE:
<221> NAME/KEY: SITE
<222> LOCATION: 23
<223> OTHER INFORMATION: Thioether linked to PMODMD

<400> SEQUENCE: 235

Arg Ala Arg Arg Xaa Arg Arg Ala Arg Ile Leu Phe Gln Tyr Arg Xaa
1               5                   10                  15

Arg Ala Arg Xaa Arg Ala Cys
            20

<210> SEQ ID NO 236
<211> LENGTH: 22
<212> TYPE: PRT
<213> ORGANISM: Artificial sequence
<220> FEATURE:
<223> OTHER INFORMATION: Synthetic sequence: Pip peptide conjugated to
      PMODMD cargo

```
-continued

<220> FEATURE:
<221> NAME/KEY: MOD_RES
<222> LOCATION: 2, 8, 21
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl
<220> FEATURE:
<221> NAME/KEY: SITE
<222> LOCATION: 22
<223> OTHER INFORMATION: Thioether linked to PMODMD

<400> SEQUENCE: 236

Arg Ala Arg Arg Xaa Arg Arg Ala Arg Ile Leu Phe Gln Tyr Arg Xaa
1               5                   10                  15

Arg Arg Xaa Arg Ala Cys
            20

<210> SEQ ID NO 237
<211> LENGTH: 22
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: MOD_RES
<222> LOCATION: 2, 8, 18, 21
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl
<220> FEATURE:
<221> NAME/KEY: SITE
<222> LOCATION: 22
<223> OTHER INFORMATION: Thioether linked to PMODMD

<400> SEQUENCE: 237

Arg Ala Arg Arg Xaa Arg Arg Ala Arg Ile Leu Phe Gln Tyr Arg Xaa
1               5                   10                  15

Arg Ala Arg Xaa Ala Cys
            20

<210> SEQ ID NO 238
<211> LENGTH: 22
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
```

```
-continued

<222> LOCATION: 5, 21
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl
<220> FEATURE:
<221> NAME/KEY: SITE
<222> LOCATION: 22
<223> OTHER INFORMATION: Thioether linked to PMODMD

<400> SEQUENCE: 238

Arg Xaa Arg Arg Ala Arg Arg Xaa Arg Ile Leu Phe Gln Tyr Arg Xaa
1               5                   10                  15

Arg Arg Xaa Arg Ala Cys
            20

<210> SEQ ID NO 239
<211> LENGTH: 22
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5, 18, 21
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl
<220> FEATURE:
<221> NAME/KEY: SITE
<222> LOCATION: 22
<223> OTHER INFORMATION: Thioether linked to PMODMD

<400> SEQUENCE: 239

Arg Xaa Arg Arg Ala Arg Arg Xaa Arg Ile Leu Phe Gln Tyr Arg Xaa
1               5                   10                  15

Arg Ala Arg Xaa Ala Cys
            20

<210> SEQ ID NO 240
<211> LENGTH: 25
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
```

```
<220> FEATURE:
<221> NAME/KEY: MOD_RES
<222> LOCATION: 5, 24
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (17)..(17)
<223> OTHER INFORMATION: Xaa is D-Arg
<220> FEATURE:
<221> NAME/KEY: SITE
<222> LOCATION: 25
<223> OTHER INFORMATION: Thioether linked to PMODMD

<400> SEQUENCE: 240

Arg Xaa Arg Arg Ala Arg Arg Xaa Arg Ile His Ile Leu Phe Gln Asn
1               5                   10                  15

Xaa Arg Met Lys Trp His Lys Ala Cys
            20                  25

<210> SEQ ID NO 241
<211> LENGTH: 15
<212> TYPE: PRT
<213> ORGANISM: Artificial sequence
<220> FEATURE:
<223> OTHER INFORMATION: Synthetic sequence: Pip peptide conjugated to
      PMODMD cargo
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5, 11, 14
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: 15
<223> OTHER INFORMATION: Thioether linked to PMODMD

<400> SEQUENCE: 241

Arg Xaa Arg Arg Ala Arg Arg Xaa Arg Ala Arg Xaa Ala Cys
1               5                   10                  15

<210> SEQ ID NO 242
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
```

<222> LOCATION: (15)..(15)
<223> OTHER INFORMATION: Xaa is D-Arg

<400> SEQUENCE: 242

Arg Xaa Arg Arg Ala Arg Arg Xaa Arg Ile Leu Phe Gln Tyr Xaa His
1               5                   10                  15

Met Lys Trp His Lys
            20

<210> SEQ ID NO 243
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Lys

<400> SEQUENCE: 243

Arg Xaa Arg Arg Ala Arg Arg Xaa Arg Ile Leu Phe Gln Tyr Xaa Arg
1               5                   10                  15

Met Lys Trp His Lys
            20

<210> SEQ ID NO 244
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Arg

<400> SEQUENCE: 244

Arg Xaa Arg Arg Ala Arg Arg Xaa Arg Ile Leu Phe Gln Tyr Xaa Arg
1               5                   10                  15

Trp Lys Trp His Lys
            20

<210> SEQ ID NO 245
<211> LENGTH: 21
<212> TYPE: PRT
<213> ORGANISM: Artificial sequence

```
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Arg

<400> SEQUENCE: 245

Arg Xaa Arg Arg Ala Arg Arg Xaa Arg Ile Leu Phe Gln Tyr Xaa Arg
1               5                   10                  15

Met Lys Trp His Lys
            20

<210> SEQ ID NO 246
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 246

Arg Xaa Arg Arg Ala Arg Arg Xaa Arg Ile Leu Phe Gln Tyr Arg Xaa
1               5                   10                  15

Arg Ala Arg Xaa Arg
            20

<210> SEQ ID NO 247
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
```

```
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl

<400> SEQUENCE: 247

Arg Xaa Arg Arg Ala Arg Arg Xaa Arg Ile Leu Phe Gln Tyr Arg Xaa
 1               5                  10                  15

Arg Xaa Arg Xaa Arg
            20

<210> SEQ ID NO 248
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl

<400> SEQUENCE: 248

Arg Xaa Arg Arg Ala Arg Arg Xaa Arg Ile Leu Phe Gln Tyr Arg Xaa
 1               5                  10                  15

Arg Arg Xaa Arg
            20

<210> SEQ ID NO 249
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
```

```
<222> LOCATION: (8)..(8)
<223> OTHER INFORMATION: Xaa is aminohexyl
<220> FEATURE:
<221> NAME/KEY: MOD_RES
<222> LOCATION: 16, 20
<223> OTHER INFORMATION: bAla
<220> FEATURE:
<221> NAME/KEY: SITE
<222> LOCATION: (18)..(18)
<223> OTHER INFORMATION: Xaa is aminohexyl

<400> SEQUENCE: 249

Arg Xaa Arg Arg Ala Arg Arg Xaa Arg Ile Leu Phe Gln Tyr Arg Ala
1               5                   10                  15

Arg Xaa Arg Ala Arg
            20

<210> SEQ ID NO 250
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 250

Arg Xaa Arg Arg Ala Arg Arg Xaa Arg Ile Leu Phe Gln Tyr Arg Xaa
1               5                   10                  15

Arg Ala Arg Xaa
            20

<210> SEQ ID NO 251
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
```

```
<222> LOCATION: (15)..(15)
<223> OTHER INFORMATION: Xaa is D-Arg

<400> SEQUENCE: 251

Arg Xaa Arg Arg Ala Arg Arg Xaa Arg Ile Leu Ile Gln Tyr Xaa His
1               5                   10                  15

Met Lys Trp His Lys
            20

<210> SEQ ID NO 252
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Lys

<400> SEQUENCE: 252

Arg Xaa Arg Arg Ala Arg Xaa Arg Ile Leu Ile Gln Tyr Xaa Arg
1               5                   10                  15

Met Lys Trp His Lys
            20

<210> SEQ ID NO 253
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Arg

<400> SEQUENCE: 253

Arg Xaa Arg Arg Ala Arg Arg Xaa Arg Ile Leu Ile Gln Tyr Xaa Arg
1               5                   10                  15

Trp Lys Trp His Lys
            20

<210> SEQ ID NO 254
<211> LENGTH: 21
<212> TYPE: PRT
<213> ORGANISM: Artificial sequence
```

```
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (15)..(15)
<223> OTHER INFORMATION: Xaa is D-Arg

<400> SEQUENCE: 254

Arg Xaa Arg Arg Ala Arg Arg Xaa Arg Ile Leu Ile Gln Tyr Xaa Arg
1               5                   10                  15

Met Lys Trp His Lys
            20

<210> SEQ ID NO 255
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 255

Arg Xaa Arg Arg Ala Arg Arg Xaa Arg Ile Leu Ile Gln Tyr Arg Xaa
1               5                   10                  15

Arg Ala Arg Xaa Arg
            20

<210> SEQ ID NO 256
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
```

```
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl

<400> SEQUENCE: 256

Arg Xaa Arg Arg Ala Arg Arg Xaa Arg Ile Leu Ile Gln Tyr Arg Xaa
1               5                   10                  15

Arg Xaa Arg Xaa Arg
            20

<210> SEQ ID NO 257
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl

<400> SEQUENCE: 257

Arg Xaa Arg Arg Ala Arg Arg Xaa Arg Ile Leu Ile Gln Tyr Arg Xaa
1               5                   10                  15

Arg Arg Xaa Arg
            20

<210> SEQ ID NO 258
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
```

```
<222> LOCATION: (8)..(8)
<223> OTHER INFORMATION: Xaa is aminohexyl
<220> FEATURE:
<221> NAME/KEY: MOD_RES
<222> LOCATION: 16, 20
<223> OTHER INFORMATION: bAla
<220> FEATURE:
<221> NAME/KEY: SITE
<222> LOCATION: (18)..(18)
<223> OTHER INFORMATION: Xaa is aminohexyl

<400> SEQUENCE: 258

Arg Xaa Arg Arg Ala Arg Arg Xaa Arg Ile Leu Ile Gln Tyr Arg Ala
1               5                   10                  15

Arg Xaa Arg Ala Arg
            20

<210> SEQ ID NO 259
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: MOD_RES
<222> LOCATION: 5
<223> OTHER INFORMATION: bAla
<220> FEATURE:
<221> NAME/KEY: SITE
<222> LOCATION: (8)..(8)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 259

Arg Xaa Arg Arg Ala Arg Arg Xaa Arg Ile Leu Ile Gln Tyr Arg Xaa
1               5                   10                  15

Arg Ala Arg Xaa
            20

<210> SEQ ID NO 260
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
```

```
<222> LOCATION: (15)..(15)
<223> OTHER INFORMATION: Xaa is D-Arg

<400> SEQUENCE: 260

Arg Ala Arg Arg Xaa Arg Arg Ala Arg Ile Leu Phe Gln Tyr Xaa His
1               5                   10                  15

Met Lys Trp His Lys
            20

<210> SEQ ID NO 261
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Lys

<400> SEQUENCE: 261

Arg Ala Arg Arg Xaa Arg Arg Ala Arg Ile Leu Phe Gln Tyr Xaa Arg
1               5                   10                  15

Met Lys Trp His Lys
            20

<210> SEQ ID NO 262
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Arg

<400> SEQUENCE: 262

Arg Ala Arg Arg Xaa Arg Arg Ala Arg Ile Leu Phe Gln Tyr Xaa Arg
1               5                   10                  15

Trp Lys Trp His Lys
            20

<210> SEQ ID NO 263
<211> LENGTH: 21
<212> TYPE: PRT
<213> ORGANISM: Artificial sequence
```

```
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Arg

<400> SEQUENCE: 263

Arg Ala Arg Arg Xaa Arg Arg Ala Arg Ile Leu Phe Gln Tyr Xaa Arg
1               5                   10                  15

Met Lys Trp His Lys
            20

<210> SEQ ID NO 264
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 264

Arg Ala Arg Arg Xaa Arg Arg Ala Arg Ile Leu Phe Gln Tyr Arg Xaa
1               5                   10                  15

Arg Ala Arg Xaa Arg
            20

<210> SEQ ID NO 265
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
```

```
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl

<400> SEQUENCE: 265

Arg Ala Arg Arg Xaa Arg Arg Ala Arg Ile Leu Phe Gln Tyr Arg Xaa
1               5                   10                  15

Arg Xaa Arg Xaa Arg
            20

<210> SEQ ID NO 266
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl

<400> SEQUENCE: 266

Arg Ala Arg Arg Xaa Arg Arg Ala Arg Ile Leu Phe Gln Tyr Arg Xaa
1               5                   10                  15

Arg Arg Xaa Arg
            20

<210> SEQ ID NO 267
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
```

```
<222> LOCATION: 8
<223> OTHER INFORMATION: bAla
<220> FEATURE:
<221> NAME/KEY: MOD_RES
<222> LOCATION: 16, 20
<223> OTHER INFORMATION: bAla
<220> FEATURE:
<221> NAME/KEY: SITE
<222> LOCATION: (18)..(18)
<223> OTHER INFORMATION: Xaa is aminohexyl

<400> SEQUENCE: 267

Arg Ala Arg Arg Xaa Arg Arg Ala Arg Ile Leu Phe Gln Tyr Arg Ala
1               5                   10                  15

Arg Xaa Arg Ala Arg
            20

<210> SEQ ID NO 268
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 268

Arg Ala Arg Arg Xaa Arg Arg Ala Arg Ile Leu Phe Gln Tyr Arg Xaa
1               5                   10                  15

Arg Ala Arg Xaa
            20

<210> SEQ ID NO 269
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
```

```
<222> LOCATION: (15)..(15)
<223> OTHER INFORMATION: Xaa is D-Arg

<400> SEQUENCE: 269

Arg Ala Arg Arg Xaa Arg Arg Ala Arg Ile Leu Ile Gln Tyr Xaa His
1               5                   10                  15

Met Lys Trp His Lys
            20

<210> SEQ ID NO 270
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Lys

<400> SEQUENCE: 270

Arg Ala Arg Arg Xaa Arg Arg Ala Arg Ile Leu Ile Gln Tyr Xaa Arg
1               5                   10                  15

Met Lys Trp His Lys
            20

<210> SEQ ID NO 271
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Arg

<400> SEQUENCE: 271

Arg Ala Arg Arg Xaa Arg Arg Ala Arg Ile Leu Ile Gln Tyr Xaa Arg
1               5                   10                  15

Trp Lys Trp His Lys
            20

<210> SEQ ID NO 272
<211> LENGTH: 21
<212> TYPE: PRT
<213> ORGANISM: Artificial sequence
```

```
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (15)..(15)
<223> OTHER INFORMATION: Xaa is D-Arg

<400> SEQUENCE: 272

Arg Ala Arg Arg Xaa Arg Arg Ala Arg Ile Leu Ile Gln Tyr Xaa Arg
1               5                   10                  15

Met Lys Trp His Lys
            20

<210> SEQ ID NO 273
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 273

Arg Ala Arg Arg Xaa Arg Arg Ala Arg Ile Leu Ile Gln Tyr Arg Xaa
1               5                   10                  15

Arg Ala Arg Xaa Arg
            20

<210> SEQ ID NO 274
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
```

-continued

```
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (18)..(18)
<223> OTHER INFORMATION: Xaa is aminohexyl
<220> FEATURE:
<221> NAME/KEY: SITE
<222> LOCATION: (20)..(20)
<223> OTHER INFORMATION: Xaa is aminohexyl

<400> SEQUENCE: 274

Arg Ala Arg Arg Xaa Arg Arg Ala Arg Ile Leu Ile Gln Tyr Arg Xaa
1               5                   10                  15
Arg Xaa Arg Xaa Arg
            20

<210> SEQ ID NO 275
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: SITE
<222> LOCATION: (19)..(19)
<223> OTHER INFORMATION: Xaa is aminohexyl

<400> SEQUENCE: 275

Arg Ala Arg Arg Xaa Arg Arg Ala Arg Ile Leu Ile Gln Tyr Arg Xaa
1               5                   10                  15
Arg Arg Xaa Arg
            20

<210> SEQ ID NO 276
<211> LENGTH: 21
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
```

```
<222> LOCATION: 8
<223> OTHER INFORMATION: bAla
<220> FEATURE:
<221> NAME/KEY: MOD_RES
<222> LOCATION: 16, 20
<223> OTHER INFORMATION: bAla
<220> FEATURE:
<221> NAME/KEY: SITE
<222> LOCATION: (18)..(18)
<223> OTHER INFORMATION: Xaa is aminohexyl

<400> SEQUENCE: 276

Arg Ala Arg Arg Xaa Arg Arg Ala Arg Ile Leu Ile Gln Tyr Arg Ala
1               5                   10                  15
Arg Xaa Arg Ala Arg
            20

<210> SEQ ID NO 277
<211> LENGTH: 20
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: MOD_RES
<222> LOCATION: 2
<223> OTHER INFORMATION: bAla
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 8
<223> OTHER INFORMATION: bAla
<220> FEATURE:
<221> NAME/KEY: SITE
<222> LOCATION: (16)..(16)
<223> OTHER INFORMATION: Xaa is aminohexyl
<220> FEATURE:
<221> NAME/KEY: MOD_RES
<222> LOCATION: 18
<223> OTHER INFORMATION: bAla
<220> FEATURE:
<221> NAME/KEY: SITE
<222> LOCATION: (20)..(20)
<223> OTHER INFORMATION: Xaa is aminohexyl

<400> SEQUENCE: 277

Arg Ala Arg Arg Xaa Arg Arg Ala Arg Ile Leu Ile Gln Tyr Arg Xaa
1               5                   10                  15
Arg Ala Arg Xaa
            20

<210> SEQ ID NO 278
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg

<400> SEQUENCE: 278
```

Arg Xaa Arg Arg Xaa Arg Ile Leu Phe Gln Tyr Xaa His Met Lys Trp
1               5                   10                  15

His Lys

<210> SEQ ID NO 279
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Lys

<400> SEQUENCE: 279

Arg Xaa Arg Arg Xaa Arg Ile Leu Phe Gln Tyr Xaa Arg Met Lys Trp
1               5                   10                  15

His Lys

<210> SEQ ID NO 280
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg

<400> SEQUENCE: 280

Arg Xaa Arg Arg Xaa Arg Ile Leu Phe Gln Tyr Xaa Arg Trp Lys Trp
1               5                   10                  15

His Lys

<210> SEQ ID NO 281
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg -continued

```
<400> SEQUENCE: 281

Arg Xaa Arg Arg Xaa Arg Ile Leu Phe Gln Tyr Xaa Arg Met Lys Trp
1               5                   10                  15

His Lys

<210> SEQ ID NO 282
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: MOD_RES
<222> LOCATION: 15
<223> OTHER INFORMATION: bAla
<220> FEATURE:
<221> NAME/KEY: SITE
<222> LOCATION: (17)..(17)
<223> OTHER INFORMATION: Xaa is aminohexyl

<400> SEQUENCE: 282

Arg Xaa Arg Arg Xaa Arg Ile Leu Phe Gln Tyr Arg Xaa Arg Ala Arg
1               5                   10                  15

Xaa Arg

<210> SEQ ID NO 283
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: (15)..(15)
<223> OTHER INFORMATION: Xaa is aminohexyl
<220> FEATURE:
<221> NAME/KEY: SITE
<222> LOCATION: (17)..(17)
<223> OTHER INFORMATION: Xaa is aminohexyl

<400> SEQUENCE: 283

Arg Xaa Arg Arg Xaa Arg Ile Leu Phe Gln Tyr Arg Xaa Arg Xaa Arg
1               5                   10                  15

Xaa Arg

<210> SEQ ID NO 284
<211> LENGTH: 17
```

```
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl

<400> SEQUENCE: 284

Arg Xaa Arg Arg Xaa Arg Ile Leu Phe Gln Tyr Arg Xaa Arg Arg Xaa
1               5                   10                  15

Arg

<210> SEQ ID NO 285
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
<222> LOCATION: 13, 17
<223> OTHER INFORMATION: bAla
<220> FEATURE:
<221> NAME/KEY: SITE
<222> LOCATION: (15)..(15)
<223> OTHER INFORMATION: Xaa is aminohexyl

<400> SEQUENCE: 285

Arg Xaa Arg Arg Xaa Arg Ile Leu Phe Gln Tyr Arg Ala Arg Xaa Arg
1               5                   10                  15

Ala Arg

<210> SEQ ID NO 286
<211> LENGTH: 17
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: MOD_RES
```

```
<222> LOCATION: 15
<223> OTHER INFORMATION: bAla
<220> FEATURE:
<221> NAME/KEY: SITE
<222> LOCATION: (17)..(17)
<223> OTHER INFORMATION: Xaa is aminohexyl

<400> SEQUENCE: 286

Arg Xaa Arg Arg Xaa Arg Ile Leu Phe Gln Tyr Arg Xaa Arg Ala Arg
1               5                   10                  15

Xaa

<210> SEQ ID NO 287
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg

<400> SEQUENCE: 287

Arg Xaa Arg Arg Xaa Arg Ile Leu Ile Gln Tyr Xaa His Met Lys Trp
1               5                   10                  15

His Lys

<210> SEQ ID NO 288
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Lys

<400> SEQUENCE: 288

Arg Xaa Arg Arg Xaa Arg Ile Leu Ile Gln Tyr Xaa Arg Met Lys Trp
1               5                   10                  15

His Lys

<210> SEQ ID NO 289
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
```

```
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg

<400> SEQUENCE: 289

Arg Xaa Arg Arg Xaa Arg Ile Leu Ile Gln Tyr Xaa Arg Trp Lys Trp
1               5                   10                  15

His Lys

<210> SEQ ID NO 290
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (12)
<223> OTHER INFORMATION: Xaa is D-Arg

<400> SEQUENCE: 290

Arg Xaa Arg Arg Xaa Arg Ile Leu Ile Gln Tyr Xaa Arg Met Lys Trp
1               5                   10                  15

His Lys

<210> SEQ ID NO 291
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: MOD_RES
<222> LOCATION: 15
<223> OTHER INFORMATION: bAla
<220> FEATURE:
<221> NAME/KEY: SITE
<222> LOCATION: (17)..(17)
<223> OTHER INFORMATION: Xaa is aminohexyl

<400> SEQUENCE: 291

Arg Xaa Arg Arg Xaa Arg Ile Leu Ile Gln Tyr Arg Xaa Arg Ala Arg
1               5                   10                  15

Xaa Arg

<210> SEQ ID NO 292
<211> LENGTH: 18
```

```
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: (15)..(15)
<223> OTHER INFORMATION: Xaa is aminohexyl
<220> FEATURE:
<221> NAME/KEY: SITE
<222> LOCATION: (17)..(17)
<223> OTHER INFORMATION: Xaa is aminohexyl

<400> SEQUENCE: 292

Arg Xaa Arg Arg Xaa Arg Ile Leu Ile Gln Tyr Arg Xaa Arg Xaa Arg
1               5                   10                  15

Xaa Arg

<210> SEQ ID NO 293
<211> LENGTH: 17
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: SITE
<222> LOCATION: (16)..(16)
<223> OTHER INFORMATION: Xaa is aminohexyl

<400> SEQUENCE: 293

Arg Xaa Arg Arg Xaa Arg Ile Leu Ile Gln Tyr Arg Xaa Arg Arg Xaa
1               5                   10                  15

Arg

<210> SEQ ID NO 294
<211> LENGTH: 18
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: MOD_RES
```

```
<222> LOCATION: 13, 17
<223> OTHER INFORMATION: bAla
<220> FEATURE:
<221> NAME/KEY: SITE
<222> LOCATION: (15)..(15)
<223> OTHER INFORMATION: Xaa is aminohexyl

<400> SEQUENCE: 294

Arg Xaa Arg Arg Xaa Arg Ile Leu Ile Gln Tyr Arg Ala Arg Xaa Arg
1               5                   10                  15

Ala Arg

<210> SEQ ID NO 295
<211> LENGTH: 17
<212> TYPE: PRT
<213> ORGANISM: Artificial sequence
<220> FEATURE:
<223> OTHER INFORMATION: Synthetic sequence: Domain 1-3 peptide sequence
<220> FEATURE:
<221> NAME/KEY: SITE
<222> LOCATION: (2)..(2)
<223> OTHER INFORMATION: Xaa is aminohexyl
<220> FEATURE:
<221> NAME/KEY: SITE
<222> LOCATION: (5)..(5)
<223> OTHER INFORMATION: Xaa is aminohexyl
<220> FEATURE:
<221> NAME/KEY: SITE
<222> LOCATION: (13)..(13)
<223> OTHER INFORMATION: Xaa is aminohexyl
<220> FEATURE:
<221> NAME/KEY: MOD_RES
<222> LOCATION: 15
<223> OTHER INFORMATION: bAla
<220> FEATURE:
<221> NAME/KEY: SITE
<222> LOCATION: (17)..(17)
<223> OTHER INFORMATION: Xaa is aminohexyl

<400> SEQUENCE: 295

Arg Xaa Arg Arg Xaa Arg Ile Leu Ile Gln Tyr Arg Xaa Arg Ala Arg
1               5                   10                  15

Xaa

<210> SEQ ID NO 296
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 296

Ile Leu Ile Gln Tyr
1               5

<210> SEQ ID NO 297
<211> LENGTH: 7
<212> TYPE: PRT
<213> ORGANISM: Artificial sequence
<220> FEATURE:
<223> OTHER INFORMATION: Synthetic sequence: Generic domain 2 sequence
<220> FEATURE:
<221> NAME/KEY: VARIANT
<222> LOCATION: (1)..(1)
<223> OTHER INFORMATION: Xaa may be present or absent. If present, Xaa
      is Ile.
<220> FEATURE:
<221> NAME/KEY: VARIANT
<222> LOCATION: (2)..(2)
<223> OTHER INFORMATION: Xaa may be present or absent. If present, Xaa
      is Lys, D-Lys, His, or Arg
<220> FEATURE:
```

```
<221> NAME/KEY: VARIANT
<222> LOCATION: (7)..(7)
<223> OTHER INFORMATION: Xaa is Asn or Tyr

<400> SEQUENCE: 297

Xaa Xaa Ile Leu Ile Gln Xaa
1               5

<210> SEQ ID NO 298
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (1)
<223> OTHER INFORMATION: Xaa is Arg, D-Arg, Lys or D-Lys
<220> FEATURE:
<221> NAME/KEY: VARIANT
<222> LOCATION: (2)
<223> OTHER INFORMATION: Xaa is Arg, His, or Lys

<400> SEQUENCE: 298

Xaa Xaa Met Lys Trp His Lys
1               5

<210> SEQ ID NO 299
<211> LENGTH: 7
<212> TYPE: PRT
<213> ORGANISM: Artificial sequence
<220> FEATURE:
<223> OTHER INFORMATION: Synthetic sequence: Domain 3 sequence
<220> FEATURE:
<221> NAME/KEY: VARIANT
<222> LOCATION: (1)
<223> OTHER INFORMATION: Xaa is Arg, D-Arg, Lys or D-Lys
<220> FEATURE:
<221> NAME/KEY: VARIANT
<222> LOCATION: (2)
<223> OTHER INFORMATION: Xaa is Arg, His, or Lys

<400> SEQUENCE: 299

Xaa Xaa Trp Lys Trp His Lys
1               5

<210> SEQ ID NO 300
<211> LENGTH: 17
<212> TYPE: PRT
<213> ORGANISM: Artificial sequence
<220> FEATURE:
<223> OTHER INFORMATION: Synthetic sequence: THR-87, a 17-mer cyclic
      peptide
<220> FEATURE:
<221> NAME/KEY: SITE
<222> LOCATION: (4)..(14)
<223> OTHER INFORMATION: D-Val D-Ala D-Leu D-Lys D-Leu D-Cys D-Leu D-Lys
      D-Leu D-Ala D-Leu

<400> SEQUENCE: 300

Pro Arg Pro Xaa Xaa Xaa Xaa Xaa Xaa Xaa Xaa Xaa Xaa Xaa Pro Arg
1               5                   10                  15

Gly

<210> SEQ ID NO 301
<211> LENGTH: 8
<212> TYPE: PRT
<213> ORGANISM: Artificial sequence
<220> FEATURE:
<223> OTHER INFORMATION: Synthetic sequence: Domain 1 sequence
```

```
<400> SEQUENCE: 301

Arg Arg Arg Arg Arg Arg Arg Arg
1               5

<210> SEQ ID NO 302
<211> LENGTH: 7
<212> TYPE: PRT
<213> ORGANISM: Artificial sequence
<220> FEATURE:
<223> OTHER INFORMATION: Synthetic sequence: Domain 3 sequence

<400> SEQUENCE: 302

Arg Arg Met Lys Trp Lys Lys
1               5

<210> SEQ ID NO 303
<211> LENGTH: 7
<212> TYPE: PRT
<213> ORGANISM: SV40

<400> SEQUENCE: 303

Pro Lys Lys Lys Arg Lys Val
1               5

<210> SEQ ID NO 304
<211> LENGTH: 5
<212> TYPE: PRT
<213> ORGANISM: Artificial sequence
<220> FEATURE:
<223> OTHER INFORMATION: Synthetic sequence: Domain 2 sequence

<400> SEQUENCE: 304

Ile Leu Ile Gln Asn
1               5
```

The invention claimed is:

1. A peptide, having a primary sequence structure comprised of at least three domains, having the arrangement:

N-terminus [Domain 1]-[Domain 2]-[Domain 3] C-terminus in which:

(i) Domain 1 comprises a sequence chosen from:

| | |
|---|---|
| RXRRBRRXR | [SEQ ID NO: 81] |
| RBRRXRRBR, or | [SEQ ID NO: 82] |
| RXRRXR | [SEQ ID NO: 74] |

(ii) Domain 2 comprises a sequence chosen from:

| | |
|---|---|
| ILFQ, or | [SEQ ID NO: 86] |
| ILIQ | [SEQ ID NO: 202] |

(iii) Domain 3 comprises a sequence chosen from:

| | |
|---|---|
| RXRBRXR | [SEQ ID NO: 159] |
| RBRXRBR | [SEQ ID NO: 162] |
| RXRRXR | [SEQ ID NO: 161] |
| RXRXRXR | [SEQ ID NO: 160] |
| RXRBRX | [SEQ ID NO: 163] |
| MKWHK, or | [SEQ ID NO: 203] |
| WKWHK | [SEQ ID NO: 204] | wherein X=aminohexanoyl, B=betaAlanine.

2. The peptide of claim 1, wherein Domain 2 comprises a sequence chosen from ILFQY [SEQ ID NO:88], or ILIQY [SEQ ID NO:296].

3. The peptide of claim 1, wherein Domain 2 comprises a sequence chosen from:

| | |
|---|---|
| $Z_2Z_3$ILFQ$Z_4$, or | [SEQ ID NO: 89] |
| $Z_2Z_3$ILIQ$Z_4$ | [SEQ ID NO: 297] | wherein $Z_2$=I or no amino acid, $Z_3$=K, dK, H, R or no amino acid, $Z_4$=N or Y.

4. The peptide of claim 1, wherein Domain 3 comprises a sequence chosen from:

| | |
|---|---|
| $Z_7Z_8$MKWHK, or | [SEQ ID NO: 298] |
| $Z_7Z_8$WKWHK | [SEQ ID NO: 299] | where $Z_7$=R, dR, K or dK (wherein d=D-aminoacid)
$Z_8$=R, H or K.

5. The peptide of claim 1, wherein Domain 3 comprises a sequence chosen from:

| | |
|---|---|
| dRRMKWHK | [SEQ ID NO: 111] |
| dRHMKWHK | [SEQ ID NO: 155] |
| dRRWKWHK | [SEQ ID NO: 157] |
| dKRMKWHK, or | [SEQ ID NO: 156] |
| dKHWKWHK. | [SEQ ID NO: 158] |

6. The peptide of claim 1, wherein Domain 1 comprises a sequence chosen from:

| | |
|---|---|
| $(RXR)_n$ where n = 2, 3 or 4, or | [SEQ ID NOs: 74-76] |
| RXRRXRIdR. | [SEQ ID NO: 80] |

7. The peptide of claim 1, wherein the peptide has a maximum length of 30 residues, including natural amino acids, X and B residues.

8. The peptide of claim 1, wherein Domain 1 has a length of from 6 to 11 residues, Domain 2 has a length of from 4 to 9 residues, and Domain 3 has a length of from 4 to 15 residues, wherein the lengths include natural amino acids, X and B residues.

9. The peptide of claim 1, comprising, or consisting of, a sequence chosen from one of SEQ ID NOs:242-295 (FIG. 25) or a sequence having at least 90% sequence identity to one of SEQ ID NOs:242-295 (FIG. 25).

10. The peptide of claim 1, comprising, or consisting of, the sequence of Domains 1 to 3 or Domains 1 to 4 of one of Pip-5e, Pip-5j or Pip-5l (SEQ ID NOs:230, 234 or 236) or a sequence having at least 90% sequence identity to the sequence of Domains 1 to 3 or Domains 1 to 4 of one of Pip-5e, Pip-5j or Pip-5l (SEQ ID NOs:230, 234 or 236).

11. The peptide of claim 1, comprising, or consisting of, a sequence chosen from one of:

| | |
|---|---|
| $Z_1Z_2Z_3ILFQZ_4Z_5RMKWHK$ | [SEQ ID NO: 113] |
| $Z_1Z_2Z_3ILFQZ_4Z_5HMKWHK$ | [SEQ ID NO: 183] |
| $Z_1Z_2Z_3ILFQZ_4Z_5RWKWHK$ | [SEQ ID NO: 184] |
| $Z_1Z_2Z_3ILFQZ_4Z_5HWKWHK$ | [SEQ ID NO: 185] |
| $Z_1Z_2Z_3ILFQZ_4RXRBRXR$ | [SEQ ID NO: 186] |
| $Z_1Z_2Z_3ILFQZ_4RXRXRXR$ | [SEQ ID NO: 187] |
| $Z_1Z_2Z_3ILFQZ_4RXRRXR$ | [SEQ ID NO: 188] |
| $Z_1Z_2Z_3ILFQZ_4RBRXRBR$ | [SEQ ID NO: 189] |
| $Z_1Z_2Z_3ILFQZ_4RXRBRXR$ | [SEQ ID NO: 190] |
| $Z_1Z_2Z_3ILFQZ_4RXRBRX$ | [SEQ ID NO: 191] |
| $Z_1Z_2Z_3ILIQZ_4Z_5RMKWHK$ | [SEQ ID NO: 192] |
| $Z_1Z_2Z_3ILIQZ_4Z_5HMKWHK$ | [SEQ ID NO: 193] |
| $Z_1Z_2Z_3ILIQZ_4Z_5RWKWHK$ | [SEQ ID NO: 194] |
| $Z_1Z_2Z_3ILIQZ_4Z_5HWKWHK$ | [SEQ ID NO: 195] |
| $Z_1Z_2Z_3ILIQZ_4RXRBRXR$ | [SEQ ID NO: 196] |
| $Z_1Z_2Z_3ILIQZ_4RXRXRXR$ | [SEQ ID NO: 197] |
| $Z_1Z_2Z_3ILIQZ_4RXRRXR$ | [SEQ ID NO: 198] |
| $Z_1Z_2Z_3ILIQZ_4RBRXRBR$ | [SEQ ID NO: 199] |
| $Z_1Z_2Z_3ILIQZ_4RXRBRXR$ | [SEQ ID NO: 200] |
| $Z_1Z_2Z_3ILIQZ_4RXRBRX$ | [SEQ ID NO: 201] | wherein:
$Z_1$=$(RXR)_n$ where n=2, 3, or 4; $(RBR)_n$ where n=2, 3, or 4; $(R)_m$ where m=5, 6, 7 or 8; RXRRXRIdR [SEQ ID NO:80]; RXRRBRRXR [SEQ ID NO:81]; or RBRRXRRBR [SEQ ID NO:82];
$Z_2$=I or no amino acid
$Z_3$=K, dK, H, R or no amino acid
$Z_4$=N, Y
$Z_5$=R or dR, K or dK
wherein d=D-aminoacid.

12. The peptide of claim 1, comprising, or consisting of, a sequence chosen from one of SEQ ID NOs:34-73 (FIG. 16), or a sequence having at least 90% sequence identity to one of SEQ ID NOs:34-73 (FIG. 16).

13. The peptide of claim 1, wherein the peptide further comprises a linker sequence at the C-terminus.

14. The peptide of claim 13, wherein the linker sequence is chosen from BCys, XCys, Cys, GGCys, BBCys, BXCys, XBCys, BX, or XB.

15. The peptide of claim 1, wherein the peptide is chemically conjugated to a cargo molecule.

16. The peptide of claim 15, wherein the conjugation is at the C-terminus of the peptide.

17. The peptide of claim 1, wherein the peptide is chemically conjugated to a cargo molecule, wherein the cargo molecule is chosen from a nucleic acid, peptide nucleic acid (PNA), phosphorodiamidate morpholino oligonucleotide (PMO), locked nucleic acid (LNA), antisense oligonucleotide, short interfering RNA (siRNA), peptide, cyclic peptide, protein, or drug.

18. The peptide of claim 15, wherein the cargo molecule has a molecular weight less than 5,000Da.

19. The peptide of claim 1, wherein the peptide is chemically conjugated to a cargo molecule, wherein the cargo molecule is PNADMD [SEQ ID NO:115] or PMODMD [SEQ ID NO:206] or a molecule having at least 90% sequence identity to one of PNADMD [SEQ ID NO:115] or PMODMD [SEQ ID NO:206].

20. A pharmaceutical composition or medicament comprising a peptide according to claim 1.

21. The pharmaceutical composition or medicament of claim 20 further comprising a pharmaceutically acceptable diluent, adjuvant or carrier.

\* \* \* \* \*

UNITED STATES PATENT AND TRADEMARK OFFICE
CERTIFICATE OF CORRECTION

PATENT NO. : 8,575,305 B2  Page 1 of 1
APPLICATION NO. : 12/996307
DATED : November 5, 2013
INVENTOR(S) : Gait et al.

It is certified that error appears in the above-identified patent and that said Letters Patent is hereby corrected as shown below:

Title Page, Item (75) Inventor is corrected to read:

--Michael John Gait, (Cambridge, GB); Andrey Alexandrovich Arzumanov, (Fulbourn, GB); Gabriela Dimitrova, Ivanova (Cambridge, GB); Haifang Yin, (Tianjin, CN); Matthew J.A. Wood, (Oxford, GB)--.

Signed and Sealed this
Third Day of March, 2015

Michelle K. Lee
*Deputy Director of the United States Patent and Trademark Office*